United States Patent
Claremon et al.

(10) Patent No.: US 8,399,504 B2
(45) Date of Patent: Mar. 19, 2013

(54) CARBAMATE AND UREA INHIBITORS OF 11BETA-HYDROXYSTEROID DEHYDROGENASE 1

(75) Inventors: David A. Claremon, Maple Glen, PA (US); Linghang Zhuang, Chalfont, PA (US); Yuanjie Ye, Ambler, PA (US); Suresh B. Singh, Kendall Park, NJ (US); Colin M. Tice, Ambler, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 0 days.

(21) Appl. No.: 12/988,374

(22) PCT Filed: Apr. 21, 2009

(86) PCT No.: PCT/US2009/002478
§ 371 (c)(1),
(2), (4) Date: Dec. 29, 2010

(87) PCT Pub. No.: WO2009/131669
PCT Pub. Date: Oct. 29, 2009

(65) Prior Publication Data
US 2011/0112062 A1    May 12, 2011

Related U.S. Application Data

(60) Provisional application No. 61/125,072, filed on Apr. 22, 2008.

(51) Int. Cl.
*A61K 31/40* (2006.01)

(52) U.S. Cl. ........ 514/423; 544/238; 544/242; 544/283; 544/353; 546/112; 546/152; 546/276.4; 548/136; 548/146; 548/152; 548/530

(58) Field of Classification Search .................. 514/423; 544/238, 242, 283, 353; 546/112, 152, 276.4; 548/136, 146, 152, 530
See application file for complete search history.

(56) References Cited

U.S. PATENT DOCUMENTS

| | | |
|---|---|---|
| 2004/0102450 A1 | 5/2004 | Ewing et al. |
| 2006/0004049 A1 | 1/2006 | Yao et al. |
| 2006/0148871 A1 | 7/2006 | Rohde et al. |
| 2007/0066584 A1 | 3/2007 | Yao et al. |
| 2007/0208001 A1 | 9/2007 | Zhuo et al. |

FOREIGN PATENT DOCUMENTS

| | | |
|---|---|---|
| EP | 1051176 | 11/2000 |
| EP | 1801098 | 6/2007 |
| JP | 2004315511 | 11/2004 |
| WO | 9937304 | 7/1999 |
| WO | WO00/09107 | 2/2000 |
| WO | 0107436 | 2/2001 |
| WO | 03088908 | 10/2003 |
| WO | 2004033427 | 4/2004 |
| WO | 2004056744 | 7/2004 |
| WO | 2005046685 | 5/2005 |
| WO | 2005047250 | 5/2005 |
| WO | 2006002349 | 1/2006 |
| WO | 2006012226 | 2/2006 |
| WO | 2006048750 | 5/2006 |
| WO | WO2009/020140 | 2/2009 |

OTHER PUBLICATIONS

International Search Report of PCT/US2009/002478, dated: Feb. 19, 2010.
Written Opinion of PCT/US2009/002478, dated: Feb. 19, 2010.
Finchman, Christopher I, et al., The Use of a Proline Ring as a Conformation 1 Restraint in CCK-B Receptor "Dipeptoids"; Bioorganic & Medicinal Chemistry Letters, 2(5):403-406, 1992.
Donohoe, Timothy J., et al., The partial reduction of heterocycles: an alternative to the Birch reduction, Tetrahedron Letters, 41:1331-1334, 2000.
Donohoe, Timothy J., et al., Stereoselectivity in the double reductive alkylation of pyrroles: synthesis of cis-3,4-disubstituted pyrrolidines, Chem. commun. pp. 141-142, 1999.

*Primary Examiner* — Douglas M Willis
(74) *Attorney, Agent, or Firm* — McCarter & English, LLP; Steven G. Davis; Michael J. DeGrazia

(57) ABSTRACT

This invention relates to novel compounds of the Formula (I)

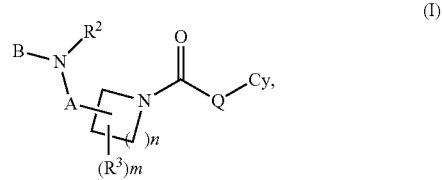

(I)

pharmaceutically acceptable salts thereof, and pharmaceutical compositions thereof, which are useful for the therapeutic treatment of diseases associated with the modulation or inhibition of 11β-HSD1 in mammals. The invention further relates to pharmaceutical compositions of the novel compounds of the Formula (I) and methods for their use in the reduction or control of the production of cortisol in a cell or the inhibition of the conversion of cortisone to cortisol in a cell.

24 Claims, No Drawings

CARBAMATE AND UREA INHIBITORS OF 11BETA-HYDROXYSTEROID DEHYDROGENASE 1

RELATED APPLICATIONS

This application is the U.S. National Stage of PCT International Application Number PCT/US2009/002478, filed Apr. 21, 2009, which claims the benefit of U.S. Provisional Application No. 61/125,072, filed Apr. 22, 2008, the entire teachings of which are incorporated herein by reference.

FIELD OF THE INVENTION

The present invention relates to inhibitors of 11β-hydroxysteroid dehydrogenase type 1 (11β-HSD1), pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-

14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Ophthalmol. Vis. Sci. 41: 1629-1683; Rauz et al. (2001) Invest. Ophthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metab. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound heating, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043, 951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula I or pharmaceutically acceptable salts thereof are effective inhibitors of 11β-HSD1. Formula I and its constituent members are defined herein as follows:

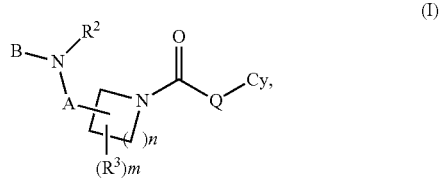

wherein
- Cy is $(C_7-C_{12})$bicycloalkyl or $(C_9-C_{12})$tricycloalkyl, in which 1-2 carbon atoms are optionally replaced with heteroatoms independently selected from N and O, and which is optionally substituted with 1-3 groups independently selected from halogen, nitro, $(CH_2)_xCN$, $(C_1-C_3)$alkyl, halo$(C_1-C_3)$alkyl, hydroxy$(C_1-C_3)$alkyl, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$;
- B is (a) $-C(O)OR^1$; or (b) aryl or heteroaryl, each optionally substituted with 1-4 groups represented by $R^6$;
- $R^1$ is $(C_1-C_8)$alkyl, $(C_2-C_8)$alkenyl, $(C_2-C_8)$alkynyl, $(C_3-C_8)$cycloalkyl, heterocyclyl, $(C_3-C_8)$cycloalkyl$(C_1-C_3)$alkyl, heterocyclyl$(C_1-C_3)$alkyl, aryl, aryl$(C_1-C_3)$alkyl, heteroaryl, or heteroaryl$(C_1-C_3)$alkyl each optionally substituted by 1-4 groups independently selected from halogen, nitro, $(CH_2)_xCN$, $(C_1-C_3)$alkyl, halo$(C_1-C_3)$alkyl, hydroxy$(C_1-C_3)$alkyl, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, $(C_3-C_8)$cycloalkyl$(C_1-C_3)$alkyl, heterocyclyl$(C_1-C_3)$alkyl, alkyl portion of aryl$(C_1-C_3)$alkyl, heteroaryl and heteroaryl$(C_1-C_3)$alkyl are further optionally substituted with oxo;
- $R^2$ and $R^3$ are independently (a) hydrogen; or (b) $(C_1-C_8)$alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo; or
- $R^2$ and $R^3$ taken together form $(C_1-C_4)$alkylene optionally substituted by up to 2 $(C_1-C_3)$alkyl groups;
- each $R^4$ is independently (a) hydrogen; or (b) $(C_1-C_{10})$alkyl, $(C_3-C_8)$cycloalkyl, aryl or aryl$(C_1-C_3)$alkyl, each optionally substituted with halogen, $(C_1-C_3)$alkoxy, $(C_1-C_3)$alkyl, halo$(C_1-C_3)$alkyl, halo$(C_1-C_3)$alkoxy, cyano, or nitro;
- $R^5$ is hydrogen or $(C_1-C_6)$alkyl;
- each $R^6$ is independently selected from halogen, nitro, $(CH_2)_xCN$, $(C_1-C_3)$alkyl, halo$(C_1-C_3)$alkyl, hydroxy$(C_1-C_3)$alkyl, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein when B is heteroaryl, $R^6$ can also be oxo;
- each $R^7$ is independently selected from halogen, nitro, cyano, $(C_1-C_3)$alkyl, halo$(C_1-C_3)$alkyl, $(C_1-C_3)$alkoxy, halo$(C_1-C_3)$alkoxy, $N(R^4)_2$ and $CON(R^4)_2$, provided that $R^7$ also includes oxo when $HetAr_1$, $HetCy_1$ and $Cy_1$ are substituted with $R^7$;
- x is 0, 1, 2 or 3;
- A is a bond or $CH_2$;
- m is 0, 1, 2, 3 or 4;
- n is 1, 2, 3 or 4; and
- Q is O or $NR^5$;
- or a pharmaceutically acceptable salt thereof.

Alternatively, each $R^4$ is independently (a) hydrogen; or (b) $(C_1-C_{10})$alkyl, aryl or aryl$(C_1-C_3)$alkyl, each optionally substituted with halogen, $(C_1-C_3)$alkoxy, $(C_1-C_3)$alkyl, halo$(C_1-C_3)$alkyl, halo$(C_1-C_3)$alkoxy, cyano, or nitro; and the remainder of the variables are as defined above for Formula I in the preceeding paragraphs.

Another embodiment is a pharmaceutical composition comprising: i) the compound of Formula I or a pharmaceutically acceptable salt thereof; and ii) a pharmaceutically acceptable carrier or diluent.

Another embodiment is a method of treating a subject with a disease associated with the activity or expression of 11β-HSD1, comprising the step of administering to the subject an effective amount of a compound of Formula I or a pharmaceutically acceptable salt thereof.

Another embodiment of the invention is a compound of Formula I or a pharmaceutically acceptable salt thereof for use in treating a subject with a disease associated with the activity or expression of 11β-HSD1.

Another embodiment of the invention is the use of a compound of Formula I or a pharmaceutically acceptable salt thereof for the manufacture of a medicament for treating a subject with a disease associated with the activity or expression of 11β-HSD1.

Another embodiment of the invention is a method of inhibiting 11β-HSD1 activity comprising the step of administering to a mammal in need of such treatment an effective amount of a compound of Formula I or a pharmaceutically acceptable salt thereof.

Another embodiment of the invention is the use of a compound of Formula I or a pharmaceutically acceptable salt thereof for the manufacture of a medicament for inhibiting 11β-HSD1 activity in a mammal in need of such treatment.

Another embodiment of the invention is a compound of Formula I or a pharmaceutically acceptable salt thereof for use in inhibiting 11β-HSD1 activity in a mammal in need of such treatment.

DETAILED DESCRIPTION OF THE INVENTION

Values and specific values for the variables in the above-described Structural Formula I have the following values:

Cy is $(C_7-C_{12})$bicycloalkyl or $(C_9-C_{12})$tricycloalkyl, in which 1-2 carbon atoms are optionally replaced with heteroatoms independently selected from N and O, and which is optionally substituted with 1-3 groups independently selected from halogen, nitro, $(CH_2)_xCN$, $(C_1-C_3)$alkyl, halo$(C_1-C_3)$alkyl, hydroxy$(C_1-C_3)$alkyl, $(CH_2)_x$ $OR^4$, halo$(C_1-C_3)$alkoxy, $(CH_2)_xN(R^4)_2$, $(CH_2)_xC$ $(=NOH)NH_2$, $(CH_2)_xNR^4CON(R^4)_2$, $(CH_2)_xCON$ $(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_x$ $NR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$;

In a specific embodiment, Cy is $(C_7-C_{12})$bicycloalkyl or $(C_9-C_{12})$tricycloalkyl which is optionally substituted with 1-3 groups independently selected from halogen, cyano, $(C_1-C_3)$alkyl, halo$(C_1-C_3)$alkyl, hydroxy$(C_1-C_3)$ alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)$ $N(R^4)_2$;

In a specific embodiment, Cy is adamantyl, optionally substituted with 1-3 groups independently selected from halogen, cyano, hydroxy, hydroxy$(C_1-C_3)$alkyl, $N(R^4)_2$, $CO_2R^4$; $CON(R^4)_2$, $CH_2CON(R^4)_2$, $SO_2N(R^4)_2$, $SO_2R^4$, $NR^4COR^4$ and $OC(=O)N(R^4)_2$, wherein each $R^4$ is independently hydrogen or $(C_1-C_3)$ alkyl.

In another specific example, Cy is bicyclooctanyl or bicyclononanyl, in which 1-2 carbon atoms are optionally replaced with heteroatoms independently selected from N and O, and which is optionally substituted with 1-3 groups independently selected from halogen, cyano, hydroxy, hydroxy$(C_1-C_3)$alkyl, $N(R^4)_2$, $CO_2R^4$; $CON(R^4)_2$, $CH_2CON(R^4)_2$, $SO_2N(R^4)_2$, $SO_2R^4$, $NR^4COR^4$ and $OC(=O)N(R^4)_2$, wherein each $R^4$ is independently hydrogen or $(C_1-C_3)$ alkyl.

B is (a) —$C(O)OR^1$; or (b) aryl or heteroaryl, each optionally substituted with 1-4 groups represented by $R^6$.

In a specific embodiment, B is heteroaryl, optionally substituted with 1-4 groups represented by $R^6$; wherein each $R^6$ is independently selected from halogen, $(CH_2)_xCN$, $(C_1-C_3)$alkyl, halo$(C_1-C_3)$alkyl, hydroxy$(C_1-C_3)$alkyl, oxo, $(CH_2)_xOR^4$, halo$(C_1-C_3)$alkoxy, $(CH_2)_xN(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xNR^4CON(R^4)_2$ and $(CH_2)_x$ $OC(=O)N(R^4)_2$.

In another specific embodiment, B is pyridine, pyridazine, pyrimidine, pyrazine, quinoline, quinoxaline, benzothiazole or thiadiazole, wherein each pyridine, pyridazine, pyrimidine, pyrazine, quinoline, quinoxaline, benzothiazole or thiadiazole is optionally substituted with 1-3 groups selected from halogen, alkyl, haloalkyl and cyano.

In another specific embodiment, B is pyridine, pyridazine, pyrimidine, pyrazine, quinoline, quinoxaline, naphthyridine, benzothiazole, thiadiazole or thiazole, wherein each pyridine, pyridazine, pyrimidine, pyrazine, quinoline, quinoxaline, naphthyridine, benzothiazole, thiadiazole or thiazole is optionally substituted with 1-4 groups represented by $R^6$; wherein each $R^6$ is independently selected from halogen, nitro, $(CH_2)_xCN$, $(C_1-C_3)$alkyl, halo$(C_1-C_3)$alkyl, hydroxy$(C_1-C_3)$alkyl, oxo, $(CH_2)_x$ $OR^4$, halo$(C_1-C_3)$alkoxy, $(CH_2)_xN(R^4)_2$, $(CH_2)_xCON$ $(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_x$ $NR^4SO_2R^4$, $(CH_2)_xNR^4CON(R^4)_2$ and $(CH_2)_xOC(=O)$ $N(R^4)_2$. Alternatively, each $R^6$ is independently selected from halogen, haloalkyl or cyano.

In a specific embodiment, B is aryl, optionally substituted with 1-4 groups represented by $R^6$; wherein each $R^6$ is independently selected from halogen, $(CH_2)_xCN$, $(C_1-C_3)$alkyl, halo$(C_1-C_3)$alkyl, hydroxy$(C_1-C_3)$alkyl, $(CH_2)_xOR^4$, halo$(C_1-C_3)$alkoxy, $(CH_2)_xN(R^4)_2$, $(CH_2)_x$ $CON(R^4)_2$, $(CH_2)_xCO_2R^4$, $(CH_2)_xSO_2N(R^4)_2$, $(CH_2)_x$ $SO_2R^4$, $(CH_2)_xNR^4COR^4$, $(CH_2)_xNR^4CO_2R^4$, $(CH_2)_x$ $NR^4SO_2R^4$, $(CH_2)_xNR^4CON(R^4)_2$ and $(CH_2)_xOC(=O)$ $N(R^4)_2$.

$R^1$ is $(C_1-C_8)$alkyl, $(C_2-C_8)$alkenyl, $(C_2-C_8)$alkynyl, $(C_3-C_8)$cycloalkyl, heterocyclyl, $(C_3-C_8)$cycloalkyl$(C_1-C_3)$ alkyl, heterocyclyl$(C_1-C_3)$alkyl, aryl, aryl$(C_1-C_3)$alkyl or heteroaryl$(C_1-C_3)$alkyl each optionally substituted by 1-4 groups independently selected from halogen, nitro, $(CH_2)_xCN$, $(C_1-C_3)$alkyl, halo$(C_1-C_3)$alkyl, hydroxy $(C_1-C_3)$alkyl, $(CH_2)_xOR^4$, halo$(C_1-C_3)$alkoxy, $(CH_2)_xN$ $(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_6)$alkynyl, $(C_3-C_8)$ cycloalkyl, heterocyclyl, $(C_3-C_8)$cycloalkyl$(C_1-C_3)$ alkyl, heterocyclyl$(C_1-C_3)$alkyl, alkyl portion of aryl $(C_1-C_3)$alkyl, heteroaryl and heteroaryl$(C_1-C_3)$alkyl are further optionally substituted with oxo.

In a specific embodiment, $R^1$ is $(C_1-C_8)$alkyl, $(C_3-C_8)$cycloalkyl, $(C_3-C_8)$cycloalkyl$(C_1-C_3)$alkyl, aryl or aryl $(C_1-C_3)$alkyl, each optionally substituted by 1-4 groups independently selected from halogen, cyano, $(C_1-C_3)$ alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON$ $(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$, wherein the $(C_1-C_8)$alkyl, $(C_3-C_8)$cycloalkyl, $(C_3-C_8)$ cycloalkyl$(C_1-C_3)$alkyl and the alkyl portion of aryl$(C_1-C_3)$alkyl are further optionally substituted with oxo.

In a specific embodiment, $R^1$ is $(C_1-C_8)$alkyl or benzyl, each optionally substituted halogen, nitro, cyano, $(C_1-C_3)$alkyl, halo$(C_1-C_3)$alkyl, $(C_1-C_3)$alkoxy, halo$(C_1-C_3)$ alkoxy, $N(R^4)_2$ or $CON(R^4)_2$.

In another specific embodiment, $R^1$ is cyclopropylmethyl, chloropyridinylmethyl or cyclopentylmethyl.

$R^2$ and $R^3$ are independently (a) hydrogen; or (b) $(C_1-C_8)$ alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl $(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo; or $R^2$ and $R^3$ taken together form $(C_1-C_4)$alkylene optionally substituted by up to 2 $(C_1-C_3)$alkyl groups.

In a specific embodiment, $R^2$ and $R^3$ are independently (a) hydrogen; or (b) $(C_1-C_8)$alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo.

In a specific embodiment, $R^2$ is (a) hydrogen; or (b) $(C_1-C_8)$alkyl, $(C_2-C_8)$alkenyl, aryl, aryl$(C_1-C_3)$alkyl, heteroaryl or heteroaryl$(C_1-C_3)$alkyl, each optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$, wherein the $(C_1-C_8)$alkyl, $(C_2-C_8)$alkenyl, the alkyl portion of aryl$(C_1-C_3)$alkyl, heteroaryl or heteroaryl$(C_1-C_3)$alkyl are further optionally substituted with oxo.

In a specific embodiment, $R^2$ is (a) hydrogen; or (b) benzyl, $(C_1-C_3)$alkyl, allyl or hydroxy$(C_1-C_3)$alkyl, each optionally substituted with halogen, nitro, cyano, $(C_1-C_3)$alkyl, halo$(C_1-C_3)$alkyl, $(C_1-C_3)$alkoxy, halo$(C_1-C_3)$alkoxy, $N(R^4)_2$ or $CON(R^4)_2$.

In another specific embodiment, $R^2$ is morpholinylethyl, tertramethylpiperidinylmethyl, pyridinylmethyl or fluoropyridinylmethyl.

In a specific embodiment, $R^3$ is (a) hydrogen; or (b) $(C_1-C_8)$alkyl, aryl, aryl$(C_1-C_3)$alkyl or $CO_2R^4$, each optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$, wherein the $(C_1-C_8)$alkyl and the alkyl portion of aryl$(C_1-C_3)$alkyl are further optionally substituted with oxo.

In a specific embodiment, $R^3$ is (a) hydrogen; or (b) $CO_2R^4$, phenyl, $(C_1-C_3)$alkyl or benzyl, each optionally substituted with halogen, nitro, cyano, $(C_1-C_3)$alkyl, halo$(C_1-C_3)$alkyl, $(C_1-C_3)$alkoxy, halo$(C_1-C_3)$alkoxy, $N(R^4)_2$ or $CON(R^4)_2$.

In another specific embodiment, $R^3$ is pyridinylmethyl or cyclopropylmethyl.

In one embodiment, $R^2$ and $R^3$ taken together form $(C_1-C_4)$alkylene optionally substituted by up to 2 $(C_1-C_3)$alkyl groups. In a specific embodiment, A is a bond and $R^2$ and $R^3$ taken together form propylene, optionally substituted with 1 or 2 $(C_1-C_3)$alkyl. In a specific embodiment, A is a bond and $R^2$ and $R^3$ taken together form ethylene, optionally substituted with 1 or 2 $(C_1-C_3)$alkyl. In another specific embodiment, A is a bond and $R^2$ and $R^3$ taken together form methylene, optionally substituted with 1 or 2 $(C_1-C_3)$alkyl.

Each $R^4$ is independently (a) hydrogen; or (b) $(C_1-C_{10})$alkyl, aryl or aryl$(C_1-C_3)$alkyl, each optionally substituted with halogen, $(C_1-C_3)$alkoxy, $(C_1-C_3)$alkyl, halo$(C_1-C_3)$alkyl, halo$(C_1-C_3)$alkoxy, cyano or nitro. In a specific embodiment, $R^4$ is independently hydrogen or $(C_1-C_3)$alkyl.

Alternatively, each $R^4$ is independently (a) hydrogen; or (b) $(C_1-C_{10})$alkyl, $(C_3-C_8)$cycloalkyl, aryl or aryl$(C_1-C_3)$alkyl, each optionally substituted with halogen, $(C_1-C_3)$alkoxy, $(C_1-C_3)$alkyl, halo$(C_1-C_3)$alkyl, halo$(C_1-C_3)$alkoxy, cyano or nitro. In a specific embodiment, $R^4$ is independently hydrogen or $(C_1-C_3)$alkyl. In a specific embodiment, $R^4$ is independently hydrogen, $(C_1-C_3)$alkyl or $(C_3-C_8)$cycloalkyl.

$R^5$ is hydrogen or $(C_1-C_8)$alkyl. In a specific embodiment, $R^5$ is hydrogen.

Each $R^6$ is independently selected from halogen, nitro, $(CH_2)_xCN$, $(C_1-C_3)$alkyl, halo$(C_1-C_3)$alkyl, hydroxy$(C_1-C_3)$alkyl, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein when B is heteroaryl, $R^6$ can also be oxo;

In a specific embodiment, B is heteroaryl and each $R^6$ is independently selected from halogen, nitro, $(CH_2)_xCN$, $(C_1-C_3)$alkyl, halo$(C_1-C_3)$alkyl, hydroxy$(C_1-C_3)$alkyl, oxo, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by HetCy$_1$ and optionally substituted cycloalkyl represented by Cy$_1$, wherein Ar$_1$, HetAr$_1$, HetCy$_1$ and Cy$_1$ are optionally substituted with one to three groups represented by R$^7$ In a specific embodiment, B is aryl and each R$^6$ is independently selected from halogen, nitro, (CH$_2$)$_x$CN, (C$_1$-C$_3$) alkyl, halo(C$_1$-C$_3$)alkyl, hydroxy(C$_1$-C$_3$)alkyl, (CH$_2$)$_x$ OR$^4$, halo(C$_1$-C$_3$)alkoxy, (CH$_2$)$_x$N(R$^4$)$_2$, (CH$_2$)$_x$C(=NOH)NH$_2$, (CH$_2$)$_x$NR$^4$CON(R$^4$)$_2$, (CH$_2$)$_x$CON(R$^4$)$_2$, (CH$_2$)$_x$CO$_2$R$^4$, (CH$_2$)$_x$SO$_2$N(R$^4$)$_2$, (CH$_2$)$_x$SO$_2$R$^4$, (CH$_2$)$_x$NR$^4$COR$^4$, (CH$_2$)$_x$NR$^4$CO$_2$R$^4$, (CH$_2$)$_x$NR$^4$SO$_2$R$^4$, (CH$_2$)$_x$OC(=O)N(R$^4$)$_2$, optionally substituted aryl represented by Ar$_1$, optionally substituted heteroaryl represented by HetAr$_1$, optionally substituted heterocyclyl represented by HetCy$_1$ and optionally substituted cycloalkyl represented by Cy$_1$, wherein Ar$_1$, HetAr$_1$, HetCy$_1$ and Cy$_1$ are optionally substituted with one to three groups represented by R$^7$.

In a specific embodiment, each R$^6$ is independently selected from halogen, cyano, (C$_1$-C$_3$)alkyl, halo(C$_1$-C$_3$)alkyl, hydroxy(C$_1$-C$_3$)alkyl, OR$^4$, N(R$^4$)$_2$, CO$_2$R$^4$, CH$_2$CO$_2$R$^4$; CON(R$^4$)$_2$, CH$_2$CON(R$^4$)$_2$, SO$_2$N(R$^4$)$_2$, SO$_2$R$^4$, NR$^4$COR$^4$, NR$^4$CO$_2$R$^4$, NR$^4$SO$_2$R$^4$, NR$^4$CON(R$^4$)$_2$ and OC(=O)N(R$^4$)$_2$.

In another specific embodiment, each R$^6$ is independently selected from halogen, nitro, CN, (C$_1$-C$_3$)alkyl, halo(C$_1$-C$_3$)alkyl, CON(R$^4$)$_2$ and CO$_2$R$^4$; and each R$^4$ is independently selected from hydrogen, (C$_1$-C$_4$)alkyl and (C$_3$-C$_6$)cycloalkyl.

Each R$^7$ is independently selected from halogen, nitro, cyano, (C$_1$-C$_3$)alkyl, halo(C$_1$-C$_3$)alkyl, (C$_1$-C$_3$)alkoxy, halo(C$_1$-C$_3$)alkoxy, N(R$^4$)$_2$ and CON(R$^4$)$_2$, provided that R$^7$ also includes oxo when HetAr$_1$, HetCy$_1$ and Cy$_1$ are substituted with R$^7$.

x is 0, 1, 2 or 3. In a specific embodiment, x is 0 or 1. In a specific embodiment x is 1. In specific embodiment, x is 0.

A is a bond or CH$_2$. In a specific embodiment, A is a bond. In another specific embodiment, A is CH$_2$.

m is 0, 1, 2, 3 or 4. In a specific embodiment, m is 0. In a specific embodiment, m is 1. In a specific embodiment, m is 2. In a specific embodiment, m is 3. In a specific embodiment, m is 4.

n is 1, 2, 3 or 4. In a specific embodiment, n is 1. In a specific embodiment, n is 2. In a specific embodiment, n is 3. In a specific embodiment, n is 4.

p is 0, 1, 2 or 3. In a specific embodiment, p is 0 or 1.

Q is O or NR$^5$. In a specific embodiment, Q is O. In a specific embodiment, Q is NR$^5$. In a specific embodiment, Q is NR$^5$ and R$^5$ is hydrogen.

In a specific embodiment, i) R$^1$OC(O)NR$^2$A or R$^1$OC(O)NR$^2$ and ii) R$_3$ are not attached to the same carbon atom. In a specific embodiment, i) NR$^2$A or NR$^2$ and ii) R$_3$ are not attached to the same carbon atom. In a specific embodiment, i) R$^1$OC(O)NR$^2$A or R$^1$OC(O)NR$^2$ and ii) R$_3$ are not attached to the same carbon atom, whereby R$^2$ and R$^3$ together form (C$_1$-C$_4$)alkylene, optionally substituted with 1 or 2 (C$_1$-C$_3$)alkyl. In a specific embodiment, i) NR$^2$A or NR$^2$ and ii) R$_3$ are not attached to the same carbon atom, whereby R$^2$ and R$^3$ together form (C$_1$-C$_4$)alkylene, optionally substituted with 1 or 2 (C$_1$-C$_3$)alkyl. In a specific embodiment, i) R$^1$OC(O)NR$^2$A or R$^1$OC(O)NR$^2$ and ii) R$_3$ are not attached to the same carbon atom, whereby R$^2$ and R$^3$ together form methylene, optionally substituted with 1 or 2 (C$_1$-C$_3$)alkyl. In a specific embodiment, i) NR$^2$A or NR$^2$ and ii) R$_3$ are not attached to the same carbon atom, whereby R$^2$ and R$^3$ together form methylene, optionally substituted with 1 or 2 (C$_1$-C$_3$)alkyl. In a specific embodiment, i) R$^1$OC(O)NR$^2$A or R$^1$OC(O)NR$^2$ and ii) R$_3$ are not attached to the same carbon atom, whereby R$^2$ and R$^3$ together form ethylene, optionally substituted with 1 or 2 (C$_1$-C$_3$)alkyl. In a specific embodiment, i) NR$^2$A or NR$^2$ and ii) R$_3$ are not attached to the same carbon atom, whereby R$^2$ and R$^3$ together form ethylene, optionally substituted with 1 or 2 (C$_1$-C$_3$)alkyl. In a specific embodiment, i) R$^1$OC(O)NR$^2$A or R$^1$OC(O)NR$^2$ and ii) R$_3$ are not attached to the same carbon atom, whereby R$^2$ and R$^3$ together form propylene, optionally substituted with 1 or 2 (C$_1$-C$_3$)alkyl. In a specific embodiment, i) NR$^2$A or NR$^2$ and ii) R$_3$ are not attached to the same carbon atom, whereby R$^2$ and R$^3$ together form propylene, optionally substituted with 1 or 2 (C$_1$-C$_3$)alkyl.

In a specific embodiment, i) R$^1$OC(O)NR$^2$A or R$^1$OC(O)NR$^2$ and ii) R$_3$ are attached to the same carbon atom and R$^2$ and R$^3$ together form (C$_1$-C$_4$)alkylene, optionally substituted with 1 or 2 (C$_1$-C$_3$)alkyl. In a specific embodiment, i) NR$^2$A or NR$^2$ and ii) R$_3$ are attached to the same carbon atom and R$^2$ and R$^3$ together form (C$_1$-C$_4$)alkylene, optionally substituted with 1 or 2 (C$_1$-C$_3$)alkyl. In a specific embodiment, i) R$^1$OC(O)NR$^2$A or R$^1$OC(O)NR$^2$ and ii) R$_3$ are attached to the same carbon atom and R$^2$ and R$^3$ together form methylene, optionally substituted with 1 or 2 (C$_1$-C$_3$)alkyl. In a specific embodiment, i) NR$^2$A or NR$^2$ and ii) R$_3$ are attached to the same carbon atom and R$^2$ and R$^3$ together form methylene, optionally substituted with 1 or 2 (C$_1$-C$_3$)alkyl. In a specific embodiment, i) R$^1$OC(O)NR$^2$A or R$^1$OC(O)NR$^2$ and ii) R$_3$ are attached to the same carbon atom and R$^2$ and R$^3$ together form ethylene, optionally substituted with 1 or 2 (C$_1$-C$_3$)alkyl. In a specific embodiment, i) NR$^2$A or NR$^2$ and ii) R$_3$ are attached to the same carbon atom and R$^2$ and R$^3$ together form ethylene, optionally substituted with 1 or 2 (C$_1$-C$_3$)alkyl. In a specific embodiment, i) R$^1$OC(O)NR$^2$A or R$^1$OC(O)NR$^2$ and ii) R$_3$ are attached to the same carbon atom and R$^2$ and R$^3$ together form propylene, optionally substituted with 1 or 2 (C$_1$-C$_3$)alkyl. In a specific embodiment, i) NR$^2$A or NR$^2$ and ii) R$_3$ are attached to the same carbon atom and R$^2$ and R$^3$ together form propylene, optionally substituted with 1 or 2 (C$_1$-C$_3$)alkyl.

Another embodiment is a compound of Formula II:

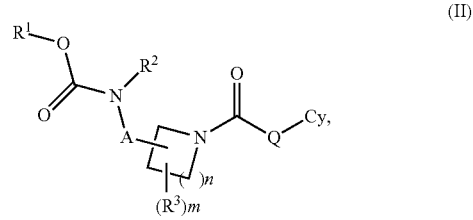

(II)

or a pharmaceutically acceptable salt thereof; wherein values and specific values for R$^1$, R$^2$, R$^3$ A, Cy, n, m and Q are as defined for Formula I above. In a specific embodiment, Q is O, and Cy is adamantyl, optionally substituted with CO$_2$Me, —CO$_2$H, CH$_2$OH, CONH$_2$, CN, NHCOMe or C(CH$_3$)$_2$OH. In a specific embodiment, Q is NR$^5$, and Cy is adamantyl, optionally substituted with CO$_2$Me, CO$_2$H, —CH$_2$OH, CONH$_2$, CN, NHCOMe or C(CH$_3$)$_2$OH. In a specific embodiment, Q is O, and Cy is adamantyl, optionally substituted with $CONH_2$. In a specific embodiment, Q is $NR^5$, and Cy is adamantyl, optionally substituted with $CONH_2$.

Another embodiment is a compound of Formula III:

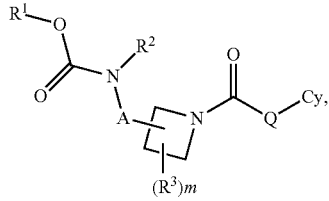

(III)

$R^2$ and $R^3$ are independently (a) hydrogen; or (b) ($C_1$-$C_8$) alkyl, ($C_2$-$C_8$)alkenyl, ($C_2$-$C_8$)alkynyl, ($C_3$-$C_8$)cycloalkyl, heterocyclyl, aryl, heteroaryl, ($C_3$-$C_8$)cycloalkyl($C_1$-$C_3$)alkyl, heterocyclyl($C_1$-$C_3$)alkyl, aryl ($C_1$-$C_3$)alkyl, heteroaryl($C_1$-$C_3$)alkyl or $(CH_2)_xCO_2R^4$, each optionally substituted by 1-4 groups independently selected from halogen, nitro, $(CH_2)_xCN$, ($C_1$-$C_3$)alkyl, halo($C_1$-$C_3$)alkyl, halo($C_1$-$C_3$)alkoxy, hydroxy($C_1$-$C_3$) alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the ($C_1$-$C_8$) alkyl, ($C_2$-$C_8$)alkenyl, ($C_2$-$C_8$)alkynyl, ($C_3$-$C_8$)cycloalkyl, heterocyclyl, heteroaryl, ($C_3$-$C_8$)cycloalkyl ($C_1$-$C_3$)alkyl, heterocyclyl($C_1$-$C_3$)alkyl, alkyl portion of aryl($C_1$-$C_3$)alkyl and heteroaryl($C_1$-$C_3$)alkyl are further optionally substituted with oxo;

or a pharmaceutically acceptable salt thereof, wherein values and specific values for the remainder of the variables in Formula III are as defined for Formula I above.

Another embodiment is a compound of Formula IIIa:

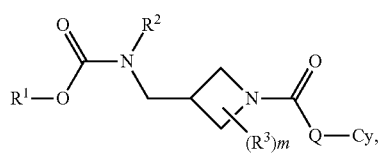

(IIIa)

or a pharmaceutically acceptable salt thereof, wherein values and specific values for the remainder of the variables in Formula IIIa are as defined for Formula I or III above.

Another embodiment is a compound of Formula IIIb:

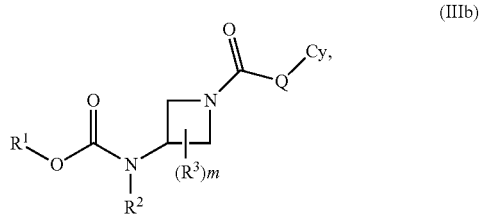

(IIIb)

or a pharmaceutically acceptable salt thereof, wherein values and specific values for the remainder of the variables in Formula IIIb are as defined for Formula I or III above. In a specific embodiment, Q is O. In another embodiment, Q is $NR^5$.

Another embodiment is a compound of Formula IV:

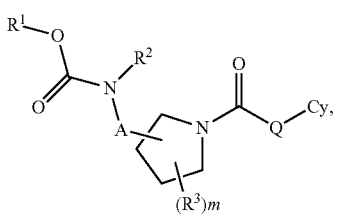

(IV)

wherein $R^2$ and $R^3$ are independently (a) hydrogen; or (b) ($C_1$-$C_8$) alkyl, ($C_2$-$C_8$)alkenyl, ($C_2$-$C_8$)alkynyl, ($C_3$-$C_8$)cycloalkyl, heterocyclyl, aryl, heteroaryl, ($C_3$-$C_8$)cycloalkyl($C_1$-$C_3$)alkyl, heterocyclyl($C_1$-$C_3$)alkyl, aryl ($C_1$-$C_3$)alkyl, heteroaryl($C_1$-$C_3$)alkyl or $(CH_2)_xCO_2R^4$, each optionally substituted by 1-4 groups independently selected from halogen, nitro, $(CH_2)_xCN$, ($C_1$-$C_3$)alkyl, halo($C_1$-$C_3$)alkyl, halo($C_1$-$C_3$)alkoxy, hydroxy($C_1$-$C_3$) alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the ($C_1$-$C_8$) alkyl, ($C_2$-$C_8$)alkenyl, ($C_2$-$C_8$)alkynyl, ($C_3$-$C_8$)cycloalkyl, heterocyclyl, heteroaryl, ($C_3$-$C_8$)cycloalkyl ($C_1$-$C_3$)alkyl, heterocyclyl($C_1$-$C_3$)alkyl, alkyl portion of aryl($C_1$-$C_3$)alkyl and heteroaryl($C_1$-$C_3$)alkyl are further optionally substituted with oxo;

or a pharmaceutically acceptable salt thereof, wherein values and specific values for the remainder of the variables in Formula IV are as defined for Formula I above.

Another embodiment is a compound of Formula IVa:

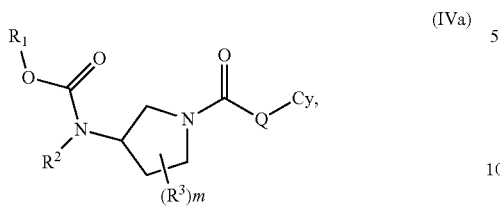

(IVa)

or a pharmaceutically acceptable salt thereof, wherein values and specific values for the remainder of the variables in Formula IVa are as defined for Formula I or IV above.

Another embodiment is a compound of Formula IVb:

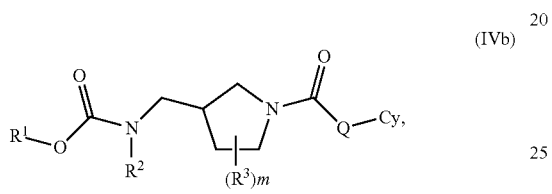

(IVb)

or a pharmaceutically acceptable salt thereof, wherein values and specific values for the remainder of the variables in Formula IVb are as defined for Formula I or IV above. In another embodiment, Q is O. In another embodiment, Q is $NR^5$.

Another embodiment is a compound of Formula IVc:

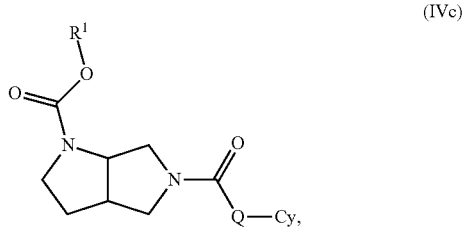

(IVc)

or a pharmaceutically acceptable salt thereof, wherein values and specific values for the remainder of the variables in Formula IVc are as defined for Formula I or II above.

Another embodiment is a compound of Formula IVd:

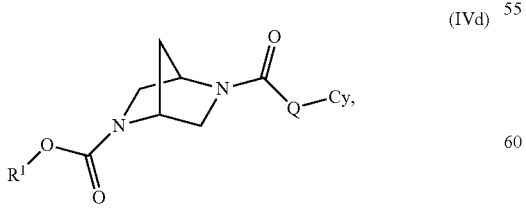

(IVd)

or a pharmaceutically acceptable salt thereof, wherein values and specific values for the remainder of the variables in Formula IVd are as defined for Formula I or II above.

Another embodiment is a compound of Formula IVe:

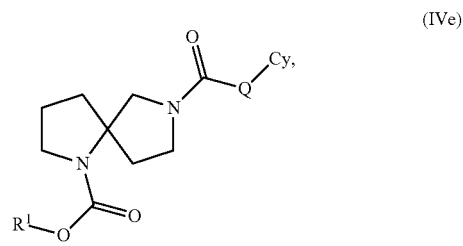

(IVe)

or a pharmaceutically acceptable salt thereof, wherein values and specific values for the remainder of the variables in Formula IVe are as defined for Formula I or II above.

Another embodiment is a compound is of Formula V:

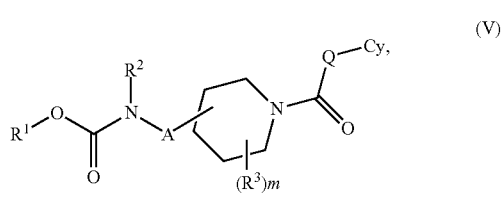

(V)

$R^2$ and $R^3$ are independently (a) hydrogen; or (b) ($C_1$-$C_8$) alkyl, ($C_2$-$C_8$)alkenyl, ($C_2$-$C_8$)alkynyl, ($C_3$-$C_8$)cycloalkyl, heterocyclyl, aryl, heteroaryl, ($C_3$-$C_8$)cycloalkyl($C_1$-$C_3$)alkyl, heterocyclyl($C_1$-$C_3$)alkyl, aryl ($C_1$-$C_3$)alkyl, heteroaryl($C_1$-$C_3$)alkyl or $(CH_2)_xCO_2R^4$, each optionally substituted by 1-4 groups independently selected from halogen, nitro, $(CH_2)_xCN$, ($C_1$-$C_3$)alkyl, halo($C_1$-$C_3$)alkyl, halo($C_1$-$C_3$)alkoxy, hydroxy($C_1$-$C_3$) alkyl, $(CH_2)_xOR^4$, $(CH_2)_xN(R^4)_2$, $(CH_2)_xC(=NOH)$ $NH_2$, $(CH_2)_xNR^4CON(R^4)_2$, $(CH_2)_xCON(R^4)_2$, $(CH_2)_x$ $CO_2R^4$, $(CH_2)_xSO_2N(R^4)_2$, $(CH_2)_xSO_2R^4$, $(CH_2)_x$ $NR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the ($C_1$-$C_8$) alkyl, ($C_2$-$C_8$)alkenyl, ($C_2$-$C_8$)alkynyl, ($C_3$-$C_8$)cycloalkyl, heterocyclyl, heteroaryl, ($C_3$-$C_8$)cycloalkyl ($C_1$-$C_3$)alkyl, heterocyclyl($C_1$-$C_3$)alkyl, alkyl portion of aryl($C_1$-$C_3$)alkyl and heteroaryl($C_1$-$C_3$)alkyl are further optionally substituted with oxo;

or a pharmaceutically acceptable salt thereof, wherein values and specific values for the remainder of the variables in Formula V are as defined for Formula I above.

Another embodiment is a compound of Formula Va:

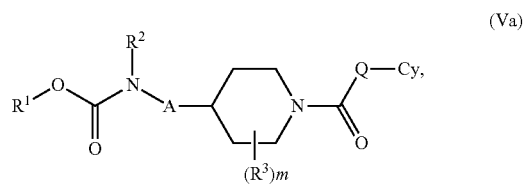

(Va)

or a pharmaceutically acceptable salt thereof, wherein values and specific values for the remainder of the variables in Formula Va are as defined for Formula I or V above.

Another embodiment is a compound of Formula Vb:

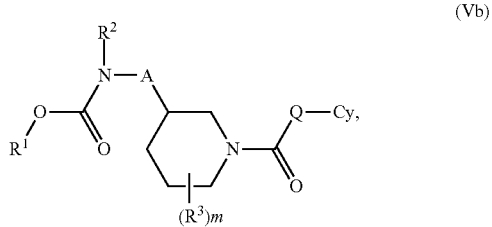

(Vb)

or a pharmaceutically acceptable salt thereof, wherein values and specific values for the remainder of the variables in Formula Vb are as defined for Formula I or V above.

Another embodiment is a compound of Formula VI:

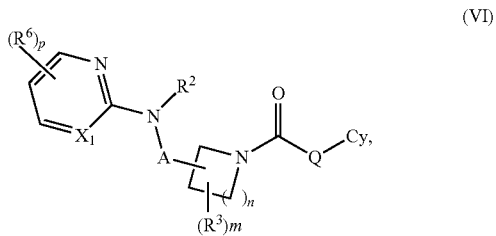

(VI)

wherein
$X_1$ is N or $CR^6$. In a specific embodiment, $X_1$ is N. In another specific embodiment, $X_1$ is $CR^6$.

Each $R^6$ is independently selected from halogen, nitro, $(CH_2)_xCN$, $(C_1-C_3)$alkyl, halo$(C_1-C_3)$alkyl, hydroxy$(C_1-C_3)$alkyl, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$; and
p is 0, 1, 2 or 3;
or a pharmaceutically acceptable salt thereof, and the values and specific values for the remainder of the variables in Formula VI are as defined for Formula I above.

Another embodiment is a compound of Formula VIa:

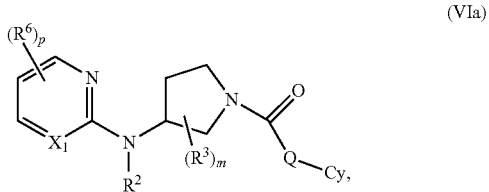

(VIa)

$X_1$ is N or $CR^6$. In a specific embodiment, $X_1$ is N. In another specific embodiment, $X_1$ is $CR^6$.

$R^2$ and $R^3$ are independently (a) hydrogen; or (b) $(C_1-C_8)$alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_6)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo;
or a pharmaceutically acceptable salt thereof, and the values and specific values for the remainder of the variables in Formula VIa are as defined for Formula I or VI above.

Another embodiment is a compound of Formula VIb:

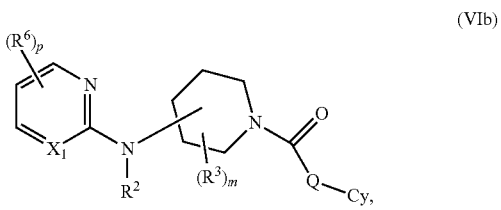

(VIb)

$X_1$ is N or $CR^6$. In a specific embodiment, $X_1$ is N. In another specific embodiment, $X_1$ is $CR^6$.

$R^2$ and $R^3$ are independently (a) hydrogen; or (b) $(C_1-C_8)$alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_6)$alkyl, $(C_2-C_8)$alkenyl, $(C_2-C_8)$alkynyl, $(C_3-C_6)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo;

or a pharmaceutically acceptable salt thereof, and the values and specific values for the remainder of the variables in Formula VIb are as defined for Formula I or VI above.

Another embodiment is a compound of Formula VII:

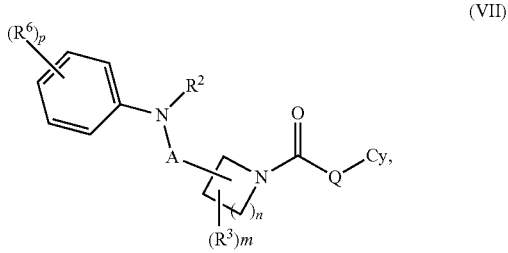

(VII)

wherein
each $R^6$ is independently selected from halogen, nitro, $(CH_2)_xCN$, $(C_1-C_3)$alkyl, halo$(C_1-C_3)$alkyl, hydroxy $(C_1-C_3)$alkyl, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$; and
p is 0, 1, 2 or 3;
or a pharmaceutically acceptable salt thereof, and the values and specific values for the remainder of the variables in Formula VII are as defined for Formula I above.

Another embodiment is a compound of Formula VIIa:

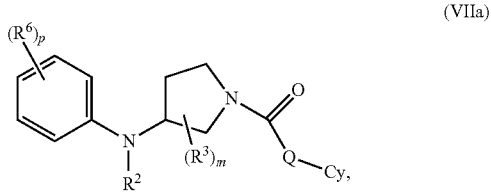

(VIIa)

$R^2$ and $R^3$ are independently (a) hydrogen; or (b) $(C_1-C_8)$ alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$ alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo;
or a pharmaceutically acceptable salt thereof, and the values and specific values for the remainder of the variables in Formula VIIIa are as defined for Formula I or VII above.

Another embodiment is a compound Formula VIIb:

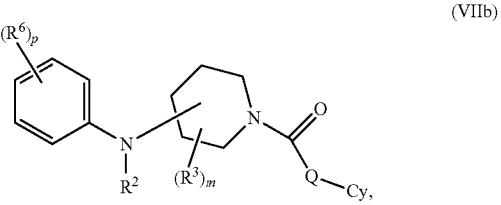

(VIIb)

$R^2$ and $R^3$ are independently (a) hydrogen; or (b) $(C_1-C_8)$ alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$ alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$ alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo;
or a pharmaceutically acceptable salt thereof, and the values and specific values for the remainder of the variables in Formula VIIIb are as defined for Formula I or VII above.

Another embodiment is a compound of Formula VIII:

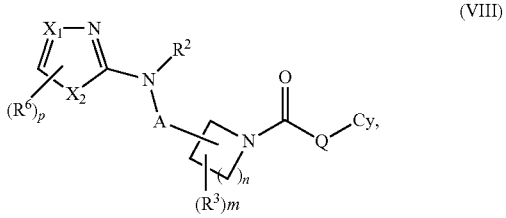

(VIII)

wherein
$X_1$ is N or $CR^6$ and $X_2$ is $NR^5$, S or O. In a specific embodiment, $X_1$ is $CR^6$ and $X_2$ is S. In another specific embodiment, $X_1$ is N and $X_2$ is S.
each $R^6$ is independently selected from halogen, nitro, $(CH_2)_xCN$, $(C_1-C_3)$alkyl, halo$(C_1-C_3)$alkyl, hydroxy $(C_1-C_3)$alkyl, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$; and p is 0 or 1;

or a pharmaceutically acceptable salt thereof, and the values and specific values for the remainder of the variables in Formula VIII are as defined for Formula I above.

Another embodiment is a compound of Formula VIIIa:

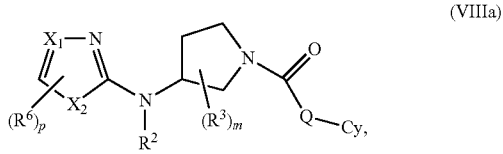

(VIIIa)

$X_1$ is N or $CR^6$ and $X_2$ is $NR^5$, S or O. In a specific embodiment, $X_1$ is $CR^6$ and $X_2$ is S. In another specific embodiment, $X_1$ is N and $X_2$ is S.

$R^2$ and $R^3$ are independently (a) hydrogen; or (b) $(C_1-C_8)$alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo;

or a pharmaceutically acceptable salt thereof, and the values and specific values for the remainder of the variables in Formula VIIIa are as defined for Formula I or VIII above.

Another embodiment is a compound of Formula VIIIb:

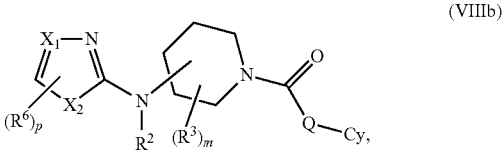

(VIIIb)

$X_1$ is N or $CR^6$ and $X_2$ is $NR^5$, S or O. In a specific embodiment, $X_1$ is $CR^6$ and $X_2$ is S. In another specific embodiment, $X_1$ is N and $X_2$ is S.

$R^2$ and $R^3$ are independently (a) hydrogen; or (b) $(C_1-C_8)$alkyl, $(C_2-C_8)$alkenyl, $(C_2-C_8)$alkynyl, $(C_3-C_6)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo;

or a pharmaceutically acceptable salt thereof, and the values and specific values for the remainder of the variables in Formula VIIIb are as defined for Formula I or VIII above.

Another embodiment is a compound of Formula IX:

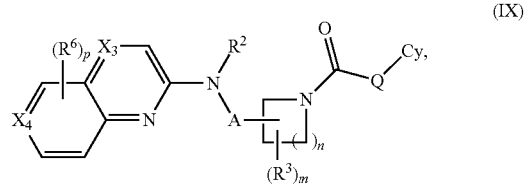

(IX)

wherein $X_3$ is N or $CR^6$;

$X_4$ is N or $CR^6$.

In a specific embodiment, $X_3$ is N. In another specific embodiment, $X_3$ is $CR^6$. In a specific embodiment, $X_4$ is N. In another specific embodiment, $X_4$ is $CR^6$. In a specific embodiment, $X_3$ is N and $X_4$ is $CR^6$. In another specific embodiment, $X_3$ is N and $X_4$ is N. In another specific embodiment, $X_3$ is $CR^6$ and $X_4$ is $CR^6$. In another specific embodiment, $X_3$ is $CR^6$ and $X_4$ is N.

Each $R^6$ is independently selected from halogen, nitro, $(CH_2)_xCN$, $(C_1-C_3)$alkyl, halo$(C_1-C_3)$alkyl, hydroxy$(C_1-C_3)$alkyl, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$; and p is 0, 1, 2 or 3;

or a pharmaceutically acceptable salt thereof, and the values and specific values for the remainder of the variables in Formula IX are as defined for Formula I above.

Another embodiment is a compound of Formula IXa:

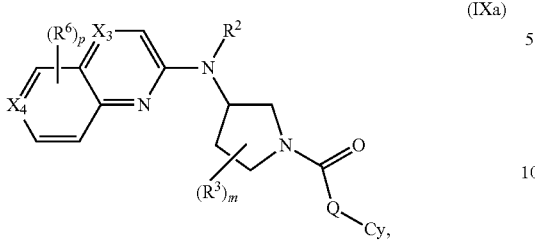

$X_3$ is N or $CR^6$;
$X_4$ is N or $CR^6$.

In a specific embodiment, $X_3$ is N. In another specific embodiment, $X_3$ is $CR^6$. In a specific embodiment, $X_4$ is N. In another specific embodiment, $X_4$ is $CR^6$. In a specific embodiment, $X_3$ is N and $X_4$ is $CR^6$. In another specific embodiment, $X_3$ is N and $X_4$ is N. In another specific embodiment, $X_3$ is $CR^6$ and $X_4$ is $CR^6$. In another specific embodiment, $X_3$ is $CR^6$ and $X_4$ is N.

$R^2$ and $R^3$ are independently (a) hydrogen; or (b) $(C_1-C_8)$alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo;

or a pharmaceutically acceptable salt thereof, and the values and specific values for the remainder of the variables in Formula IXa are as defined for Formula I or IX above.

Another embodiment is a compound of Formula X:

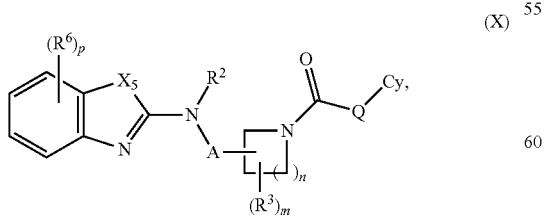

wherein
$X_5$ is S or O. In a specific embodiment, $X_5$ is S. In a specific embodiment, $X_5$ is O.

Each $R^6$ is independently selected from halogen, nitro, $(CH_2)_xCN$, $(C_1-C_3)$alkyl, halo$(C_1-C_3)$alkyl, hydroxy$(C_1-C_3)$alkyl, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$; and
p is 0, 1, 2 or 3;

or a pharmaceutically acceptable salt thereof, and the values and specific values for the remainder of the variables are as defined for Formula I above.

Another embodiment is a compound of Formula Xa:

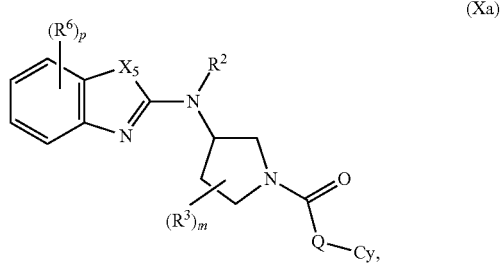

$X_5$ is S or O. In a specific embodiment, $X_5$ is S. In a specific embodiment, $X_5$ is O.

$R^2$ and $R^3$ are independently (a) hydrogen; or (b) $(C_1-C_8)$alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo;

or a pharmaceutically acceptable salt thereof, and the values and specific values for the remainder of the variables in Formula Xa are as defined for Formula I or X above.

Another embodiment is a compound of Formula I or any one of Formulas II, III, IIIa, IIIb, IV, IVa, IVb, IVc, IVd, IVe, V, Va, Vb, wherein:
A is $CH_2$ or a single bond;
B is $—C(O)OR^1$;
$R^1$ is $(C_1-C_4)$alkyl or benzyl;

$R^2$ is hydrogen, methyl, allyl, 2-hydroxyethyl, benzyl;
$R^3$ is hydrogen, methyl, phenyl, benzyl or —C(O)OEt;
or $R^2$ and $R^3$ taken together are methylene, ethylene or propylene;
Cy is 2-adamantyl, 1-(hydroxymethyl)-4-adamantyl, 1-(carboxy)-4-adamantyl, 1-(methoxycarbonyl)-4-adamantyl, 1-carbamoyl-4-adamantyl, 1-cyano-4-adamantyl, 1-(acetylamino)-4-adamantyl, 1-(2-hydroxy-2-propyl-4-adamantyl 1-(hydroxy-1-methyl-ethyl)-4-adamantyl or 1-(hydroxyethyl)-4-adamantyl;
Q is O or $NR^5$;
$R^5$ is H;
m is 0 or 1; and
n is 1, 2 or 3.

Another embodiment is a compound of Formula I or any one of Formulas VI, VIa, VIb, VII, VIIa, VIIb, VIII, VIIIa, VIIIb, IX, IXa, X and Xa, wherein:
A is $CH_2$ or a single bond;
B is phenyl, pyridinyl, pyrimidinyl, thiadiazolyl or thiazolyl;
$R^2$ is hydrogen, methyl, allyl, hydroxyethyl, benzyl;
$R^3$ is hydrogen, methyl, phenyl, benzyl or —C(O)OEt;
or $R^2$ and $R^3$ taken together are methylene, ethylene or propylene;
Cy is 2-adamantyl, 1-(hydroxymethyl)-4-adamantyl, 1-(methoxycarbonyl)-4-adamantyl, 1-carbamoyl-4-adamantyl, 1-cyano-4-adamantyl, 1-(acetylamino)-4-adamantyl, 1-(2-hydroxy-2-propyl)-4-adamantyl or 1-(hydroxyethyl)-4-adamantyl, or 3-carbamoyl-bicyclo[3.3.1]nonan-9-yl;
Q is O or $NR^5$;
$R^5$ is H;
$R^6$ is $CF_3$, methyl, cyano or fluorine;
m is 0 or 1; and
n is 1, 2 or 3.

Another embodiment is a compound of Formula I or any one of Formulas VI, VIa, VIb, VII, VIIa, VIIb, VIII, VIIIa, VIIIb, IX, IXa, X, and Xa, wherein:
Cy is $(C_7-C_{12})$bicycloalkyl or $(C_9-C_{12})$tricycloalkyl which is optionally substituted with 1-3 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and OC(=O)N$(R^4)_2$;
$R^2$ is (a) hydrogen; or (b) $(C_1-C_8)$alkyl, $(C_2-C_8)$alkenyl, aryl, aryl$(C_1-C_3)$alkyl, heteroaryl or heteroaryl$(C_1-C_3)$alkyl, each optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and OC(=O)N$(R^4)_2$, wherein the $(C_1-C_8)$alkyl, $(C_2-C_8)$alkenyl, alkyl portion of aryl$(C_1-C_3)$alkyl, heteroaryl or heteroaryl$(C_1-C_3)$alkyl are further optionally substituted with oxo;
$R^3$ is (a) hydrogen; or (b) $(C_1-C_8)$alkyl, aryl, aryl$(C_1-C_3)$alkyl or $CO_2R^4$, each optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and OC(=O)N$(R^4)_2$, wherein the $(C_1-C_8)$alkyl and alkyl portion of aryl$(C_1-C_3)$alkyl are further optionally substituted with oxo;
$R^4$ is independently hydrogen, $(C_1-C_4)$alkyl or $(C_3-C_6)$cycloalkyl; and each $R^6$ is independently selected from halogen, cyano, nitro, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and OC(=O)N$(R^4)_2$, and the remainder of the variables are as defined for Formula I, VI, VIa, VIb, VII, VIIa, VIIb, VIII, VIIIa, VIIIb, IX, IXa, X, and Xa.

Another embodiment is a method of treating a subject with a disease associated with the activity or expression of 11β-HSD1, comprising the step of administering to the subject an effective amount of a compound of Structural Formula I, II, III, IIIa, IIIb, IV, IVa, IVb, IVc, IVd, IVe, V, Va, Vb, VI, VIa, VIb, VII, VIIa, VIIb, VIII, VIIIa, VIIIb, IX, IXa, X, and Xa or a pharmaceutically acceptable salt thereof.

Another embodiment is a method of inhibiting 11β-HSD1 activity comprising the step of administering to a mammal in need of such treatment an effective amount of a compound of Structural Formula I, II, III, IIIa, IIIb, IV, IVa, IVb, IVc, IVd, IVe, V, Va, Vb, VI, VIa, VIb, VII, VIIa, VIIb, VIII, VIIIa, VIIIb, IX, IXa, X, and Xa or a pharmaceutically acceptable salt thereof.

Another embodiment is a pharmaceutical composition comprising i) the compound in any one of Structural Formulas I, II, III, IIIa, IIIb, IV, IVa, IVb, IVc, IVd, IVe, V, Va, Vb, VI, VIa, VIb, VII, VIIa, VIIb, VIII, VIIIa, VIIIb, IX, IXa, X, and Xa; or a pharmaceutically acceptable salt thereof; and ii) a pharmaceutically acceptable carrier or diluent enantiomer or diastereomer thereof.

DEFINITIONS

The term "alkyl", used alone or as part of a larger moiety such as "alkoxyalkyl" or "alkylamine" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, i-pentyl, n-hexyl, n-heptyl, n-octyl, n-nonyl, n-decyl and the like.

The term "cycloalkyl" means a monocyclic, bicyclic or tricyclic, saturated hydrocarbon ring having 3-10 carbon atoms and includes, for example, cyclopropyl, cyclobutyl, cyclopentyl, cyclohexyl, cycloheptyl, cyclooctyl, bicyclo[2.2.2]octyl, bicyclo[2.2.1]heptyl, spiro[4.4]nonane, adamantyl and the like. Unless otherwise described, exemplary substituents for a substituted cycloalkyl group include the substituents described for the cycloalkyl group represented by $R^6$.

"Aryl", used alone or as part of a larger moiety as in "arylalkyl", "arylalkoxy", or "aryloxyalkyl", means a 6-10 membered carbocyclic aromatic monocyclic or polycyclic ring system. Examples include phenyl and naphthyl. The term "aryl" also includes phenyl rings fused to non-aromatic carbocyclic ring or to a heterocyclyl group. The term "aryl" may be used interchangeably with the terms "aromatic group", "aryl ring" "aromatic ring", "aryl group" and "aromatic group". Unless otherwise described, exemplary substituents for a substituted aryl group include the substituents described for the heterocyclyl group represented by $R^6$.

"Hetero" refers to the replacement of at least one carbon atom member in a ring system with at least one heteroatom selected from N, S, and O. A hetero ring may have 1, 2, 3, or 4 carbon atom members replaced by a heteroatom.

"Heteroaryl", used alone or as part of a larger moiety as in "heteroarylalkyl" or "heteroarylalkoxy", means a 5-10 membered monovalent heteroaromatic monocyclic and polycylic ring radical containing 1 to 4 heteroatoms independently selected from N, O, and S. The term "heteroaryl" also includes monocyclic heteroaryl ring fused to non-aromatic carbocyclic ring or to a heterocyclyl group. Heteroaryl groups include furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, quinazolinyl, benzothienyl, benzofuranyl, 2,3-dihydrobenzofuranyl, benzodioxolyl, benzimidazolyl, indazolyl, benzisoxazolyl, benzoxazolyl, benzothiazolyl, cinnolinyl, phthalzinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,3,4-thiadiazolyl, 1,2,4-triazinyl, 1,3,5-triazinyl, tetrazolyl, and pteridinyl. The terms "heteroaryl", "heteroaromatic", "heteroaryl ring", "heteroaryl group" and "heteroaromatic group" are used interchangeably herein. "Heteroarylalkyl" means alkyl substituted with heteroaryl; and "heteroarylalkoxy" means alkoxy substituted with heteroaryl. Unless otherwise described, exemplary substituents for a substituted heterocyclyl group include the substituents described for the heteroaryl group represented by $R^6$.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide and isothiazolidine 1,1-dioxide. Unless otherwise described, exemplary substituents for a substituted heterocyclyl group include the substituents described for the heterocyclyl group represented by $R^6$.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

When a disclosed compound or its pharmaceutically acceptable salt is named or depicted by structure, it is to be understood that solvates or hydrates of the compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

The following abbreviations have the indicated meanings:

| Abbreviation | Meaning |
| --- | --- |
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| EDC•HCl | 1-[3-(dimethylamino)propyl]-3-ethylcarbodiimide hydrochloride |
| Equiv | equivalents |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazole-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |
| Satd | saturated |
| SOCl$_2$ | thionyl chloride |
| SPA | scintillation proximity assay |
| SPE | solid phase extraction |
| TBS | t-butyldimethylsilyl |
| TBSCl | t-butyldimethylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |
| TFAA | trifluoroacetic anhydride |
| Tlc | thin layer chromatography |
| TMS | trimethylsilyl |
| TMSCl | chlorotrimethylsilane or trimethylsilyl chloride |
| t$_R$ | retention time |
| TsOH | p-toluenesulfonic acid |

General Description of Synthesis

Compounds of Formula I can be prepared by several processes. In the discussion below $R^1$, $R^2$, $R^3$, $R^4$, $R^5$, $R^6$, A, B, Q, Cy, m and n have the meanings indicated above unless otherwise noted. In cases where the synthetic intermediates and final products of Formulas I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and generally not described explicitly. Generally reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In a first process, a compound of Formula I wherein Q is O, can be prepared by reaction of a cyclic amine of Formula 2 with an electrophile of Formula 3, wherein $Z^1$ is a leaving group such as halide, aryloxide, 1-imidazolyl and the like, in the presence of a soluble base such as i-Pr$_2$NEt or an insoluble base such as K$_2$CO$_3$ in an inert solvent such as THF, CH$_2$Cl$_2$ or MeCN at 0-100° C. for 1-24 h.

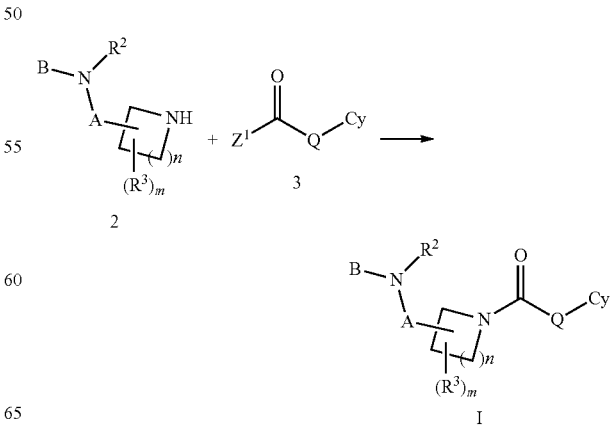

Certain cyclic amines of Formula 2 are commercially available, can be prepared by previously described routes or can be prepared as described below. tert-Butyl 1,7-diazaspiro[4.4]nonane-1-carboxylate was purchased from WuXi Pharmatech, Shanghai, China. tert-Butyl hexahydropyrrolo[3,4-b]pyrrole-1(2H)-carboxylate was purchased from J & W PharmLab LLC, Levittown, Pa., USA. tert-Butyl azetidin-3-ylmethylcarbamate was purchased from AB Chem Inc, Ville St-Laurent, Quebec, Canada. (R)-3-N-Boc-aminomethylpyrrolidine was purchased from AstaTech, Bristol, Pa., USA.

The preparation of tert-butyl 3-methylpyrrolidin-3-ylcarbamate has been described in Yoshida, T. et al *Chem. Pharm. Bull.* 1996, 44, 1376-1386 which is hereby incorporated by reference.

The preparation of tert-butyl 3-(trifluoromethyl)pyrrolidin-3-ylcarbamate has been described in Fukui, H. et al *Bioorg. Med. Chem. Lett.* 1998, 8, 2833-2838 which is hereby incorporated by reference.

The preparation of tert-butyl methyl(3-methylpyrrolidin-3-yl)carbamate has been described in Tsuzuki, Y. et al *J. Med. Chem.* 2004, 47, 2097-2019 which is hereby incorporated by reference.

The preparation of tert-butyl (3-methylazetidin-3-yl)methylcarbamate has been described in U.S. Pat. No. 5,576,320 Preparation IV which is hereby incorporated by reference.

The preparation of tert-butyl 1-benzyl-3-phenylpyrrolidin-3-ylcarbamate has been described in Hagen, S. E. et al *J. Med. Chem.* 1990, 33, 849-854 which is hereby incorporated by reference. tert-butyl 3-phenylpyrrolidin-3-ylcarbamate can be prepared by catalytic hydrogenation of tert-butyl 1-benzyl-3-phenylpyrrolidin-3-ylcarbamate.

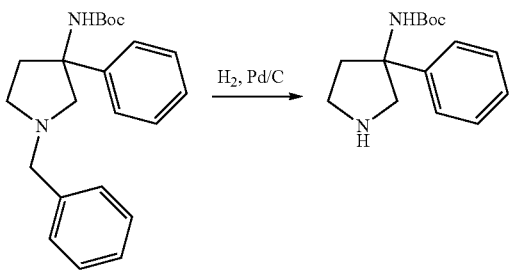 [SMILES: CC(C)(C)OC(=O)NC1(c2ccccc2)CCN(Cc2ccccc2)C1 ; CC(C)(C)OC(=O)NC1(c2ccccc2)CCNC1]

The preparation of 1,3-dibenzylpyrrolidine-3-carboxylic acid has been described in U.S. Pat. No. 7,094,780 Example A28. tert-butyl 3-benzylpyrrolidin-3-ylcarbamate can be prepared by Curtius rearrangement of 1,3-dibenzylpyrrolidine-3-carboxylic acid using, for example, diphenylphosphoryl azide followed by Boc protection of the resulting amine and catalytic hydrogenation to remove the N-benzyl group.

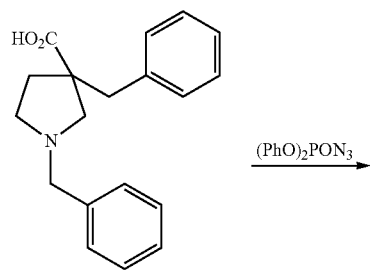

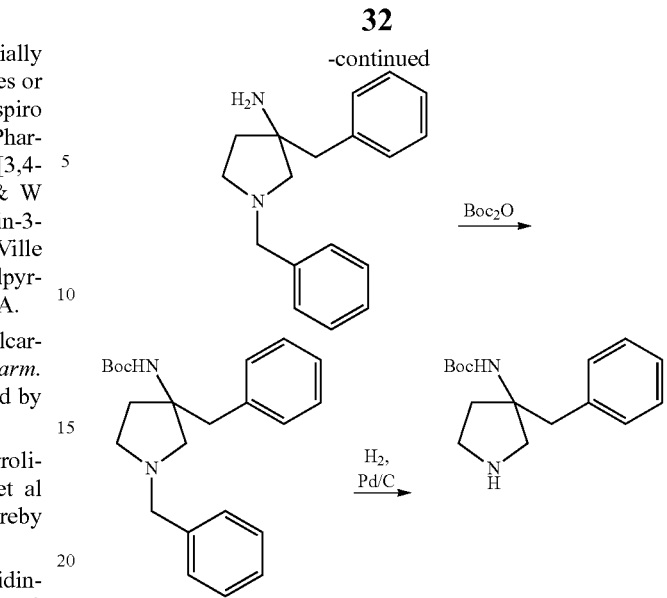

The preparation of (2S,3R)-benzyl 3-(tert-butoxycarbonylamino)-2-phenylpyrrolidine-1-carboxylate is described in US Published Patent Application 2005/0288358 Preparatory Example 10 which is hereby incorporated by reference. tert-Butyl (2S,3R)-2-phenylpyrrolidin-3-ylcarbamate can be prepared from (2S,3R)-benzyl 3-(tert-butoxycarbonylamino)-2-phenylpyrrolidine-1-carboxylate by removal of the Cbz protecting group by catalytic hydrogenation.

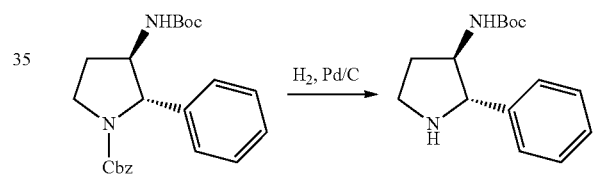

tert-Butyl (2S,3R)-2-o-tolylpyrrolidin-3-ylcarbamate can be prepared using the procedure described for Intermediate 67 in US Published Patent Application 2005/0043354, which is hereby incorporated by reference, using tert-butyl (2S,3R)-2-o-tolyl-1-tosylpyrrolidin-3-ylcarbamate (Intermediate 62) as starting material Amines of Formula 2, wherein B is an aryl or heteroaryl group, can be prepared from protected amines of Formula 4, wherein $Z^2$ is an amine protecting group such as Boc, Teoc, Cbz or the like, by reaction with a compound of Formula 5, wherein B is aryl or heteroaryl and $Z^3$ is halide, methanesulfonate or trifluoromethanesulfonate, followed by removal of protecting group $Z^2$.

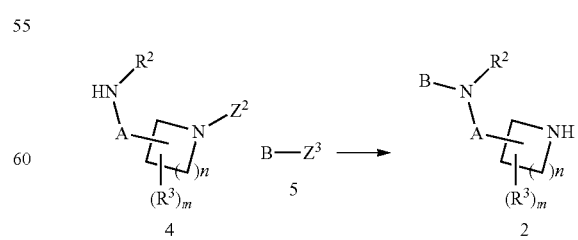

When B is aryl or heteroaryl bearing an electron withdrawing group such as cyano, trifluoromethyl or the like attached ortho or para to $Z^3$, $Z^3$ is preferably fluoro or chloro and the reaction can be run in the presence of a base such as i-Pr$_2$NEt at a temperature from 50-200° C. in a solvent such as n-PrOH. When B does not bear an electron withdrawing group, Z$^3$ is preferably bromine or iodine and the reaction is run in the presence of a palladium or copper catalyst and suitable additives. Alternatively Z$^3$ is B(OH)$_2$ and a copper catalyst is used.

Electrophiles of Formula 3, wherein Z$^1$ is Cl and Q is O are chloroformates and are prepared by reaction of alcohols of formula 6 with phosgene or triphosgene in an inert solvent such as toluene, CH$_2$Cl$_2$ or THF in the presence of a base such as pyridine at −20° C. to 80° C., preferably 0° C. to 25° C. for between 0.5 h and 24 h.

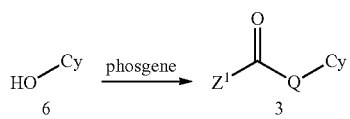

Electrophiles of Formula 3 wherein Z$^1$=aryloxide are carbonates and are prepared by reaction of alcohols of Formula 6 with aryl chloroformates of Formula 7 in an inert solvent such as toluene, CH$_2$Cl$_2$ or THF in the presence of a base such as triethylamine at 0° C. to 80° C., preferably 5° C. to 25° C. for between 1 h and 24 h.

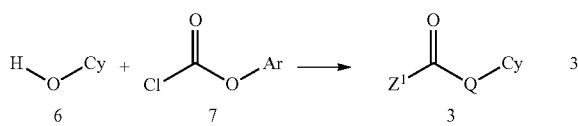

Similarly, treatment of alcohols of Formula 6 with carbonyl diimidazole affords compounds of Formula 3, wherein Z$^1$ is 1-imidazolyl. Additionally, treatment of alcohols of Formula 6 with disuccinimidyl carbonate affords compounds of Formula 3, wherein Z$^1$ is succinimidyl-1-oxy.

In a second process, a compound of Formula I, wherein Q is O, can be prepared by reaction of a compound of Formula 8, wherein Z$^4$ is a leaving group such as such as halide, aryloxide or azole, preferably chloride, with an alcohol of formula 6 in a solvent such as pyridine at 50-150° C.

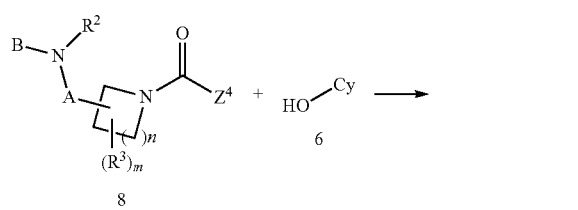

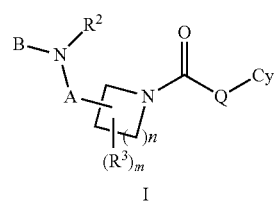

Alternatively, the alkoxide anion of alcohol 6 can be formed using a strong base such as NaH in an inert solvent such as THF and DMF and reacted with 8.

Intermediates of Formula 8, wherein Z$^4$ is chlorine, can be prepared by reaction of amines of Formula 2 with phosgene or triphosgene in the presence of a base such as pyridine at −40 to 40° C., preferably around 0° C., in an inert solvent such as CH$_2$Cl$_2$, THF or MeCN for between 30 min and 24 h.

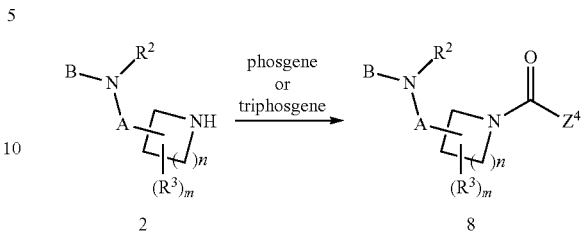

In a third process, a compound of Formula I, wherein Q is NR$^5$ and R$^5$ is hydrogen, can be prepared by reaction of an amine of Formula 2 with an isocyanate of Formula 9, in an inert solvent such as CH$_2$Cl$_2$, TH or MeCN at −10-25° C.

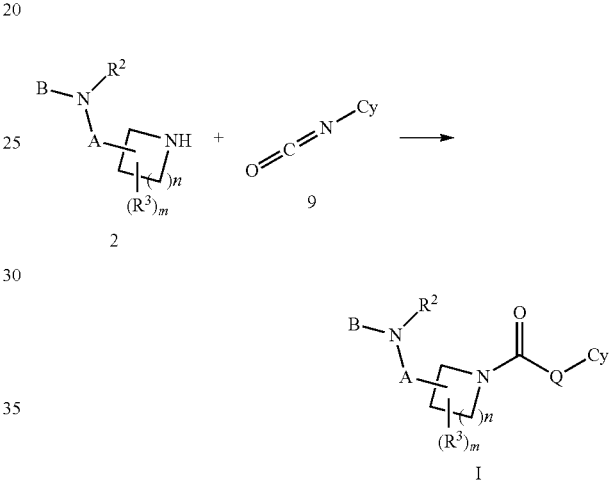

Isocyanates of Formula 9 can be prepared from amines of Formula 10 by treatment with phosgene or triphosgene.

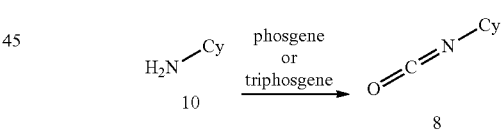

In a fourth process, a compound of Formula I, wherein Q is NR$^5$ and R$^5$ is (C$_1$-C$_6$)alkyl, can be prepared by reaction of an amine of Formula 2 with a carbamoyl chloride of Formula 11, in an inert solvent such as CH$_2$Cl$_2$, THF or MeCN at 0-100° C.

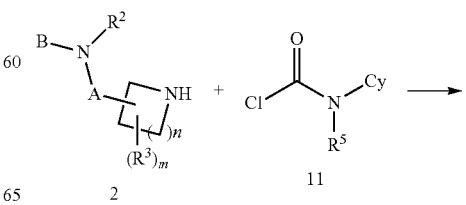

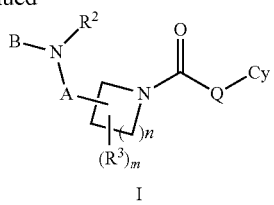

Carbamoyl chlorides of Formula 11 can be prepared from amines of Formula 12 by treatment with phosgene or triphosgene, in the presence of a base such as pyridine.

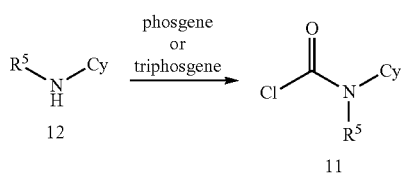

In a fifth process a compound of Formula I, wherein B is aryl or heteroaryl, can be prepared by reaction of an intermediate of Formula 5 with an amine of Formula 13.

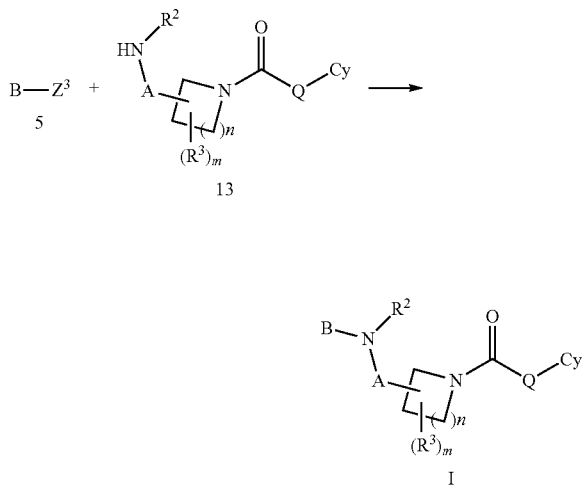

When B is aryl or heteroaryl bearing an electron withdrawing group such as cyano, trifluoromethyl or the like attached ortho or para to $Z^3$, $Z^3$ is preferably fluoro or chloro and the reaction can be run in the presence of a base such as i-$Pr_2NEt$ at a temperature from 50-200° C. in a solvent such as n-PrOH. When B does not bear an electron withdrawing group, $Z^3$ is preferably bromine or iodine and the reaction is run in the presence of a palladium or copper catalyst and suitable additives. Alternatively $Z^3$ is $B(OH)_2$ and a copper catalyst is used.

In a sixth process, a compound of Formula I, wherein B is $C(O)OR^1$, can be prepared by reaction of amine of Formula 13 with an electrophile of Formula 14, wherein $Z^5$ is halide, aryloxide, 1-succimidyloxy or 1-imidazolyl.

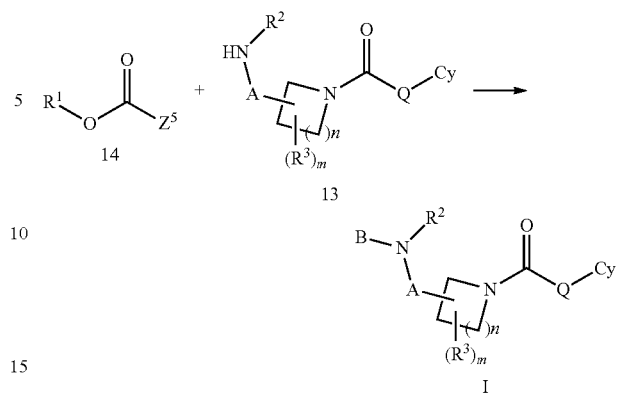

In a seventh process, a compound of Formula I can be prepared from another compound of Formula I. For example:
(1) a compound of Formula I, wherein Cy is substituted by $CO_2Me$, can be treated with $LiBH_4$ to afford a compound of Formula I, wherein Cy is substituted by $CH_2OH$.
(2) a compound of Formula I, wherein Cy is substituted with $CO_2Me$, can be treated with MeMgBr to afford a compound of Formula I, wherein Cy is substituted by $C(Me)_2OH$.
(3) a compound of Formula I, wherein Cy is substituted by $CO_2H$, can be coupled with $NH_3$ using, for example, EDC to afford a compound of Formula I, wherein Cy is substituted with $CONH_2$.
(4) a compound of Formula I, wherein Cy is substituted by $CONH_2$, can be treated with trifluoroacetic anhydride and pyridine, to afford a compound of Formula I, wherein Cy is substituted with CN.
(5) a compound of Formula I, wherein B is $C(O)OR^1$, $R^1$ is $(C_1-C_6)$alkyl and $R^2$ is H, can be alkylated with methyl iodide, allyl bromide or benzyl bromide to give a compound of Formula I, wherein B is $C(O)OR^1$, $R^1$ is $(C_1-C_6)$alkyl and $R^2$ is methyl, allyl or benzyl.
(6) a compound of Formula I, wherein $R^2$ is allyl, can be treated with disiamylborane followed by $H_2O_2$ and NaOH to afford a compound of Formula I, wherein $R^2$ is 3-hydroxypropyl.
(7) a compound of Formula I, wherein $R^2$ is allyl, can be treated with ozone followed by $NaBH_4$ to afford a compound of Formula I, wherein $R^2$ is 2-hydroxyethyl.

Analytical Methods

LC-MS Method 1 (3 min)
Column: Chromolith SpeedRod, RP-18e, 50×4.6 mm; Mobil phase: A: 0.01% TFA/water, B: 0.01% TFA/$CH_3CN$; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

LC-MS Method 2 (16 min)
Column: Chromolith SpeedRod, RP-18e, 50×4.6 mm; Mobil phase: A: 0.01% TFA/water, B: 0.01% TFA/$CH_3CN$; Flow rate: 1 mL/min; Gradient:

| Time (min) | A % | B % |
| --- | --- | --- |
| 0.0 | 90 | 10 |
| 14.0 | 10 | 90 |
| 15.0 | 10 | 90 |
| 15.1 | 90 | 10 |
| 16.0 | 90 | 10 |

LC-MS Method 3 (10-80)

| Column | YMC-PACK ODS-AQ, 50 × 2.0 mm 5 μm |
| --- | --- |
| Mobile Phase | A: water (4 L) + TFA (1.5 mL)) |
| | B: acetonitrile (4 L) + TFA (0.75 mL)) |

| TIME (min) | A % | B % |
| --- | --- | --- |
| 0 | 90 | 10 |
| 2.2 | 20 | 80 |
| 2.5 | 20 | 80 |

| Flow Rate | 1 mL/min |
| --- | --- |
| Wavelength | UV 220 nm |
| Oven Temp | 50° C. |
| MS ionization | ESI |

Preparations

Preparation 1

2-Adamantyl Chloroformate

The title compound was prepared from 2-adamantanol as disclosed in U.S. Pat. No. 5,270,302, Example 74, Step (a), the contents of which are hereby incorporated by reference.

Preparation 2

1-(methoxycarbonyl)-4-adamantyl chloroformate

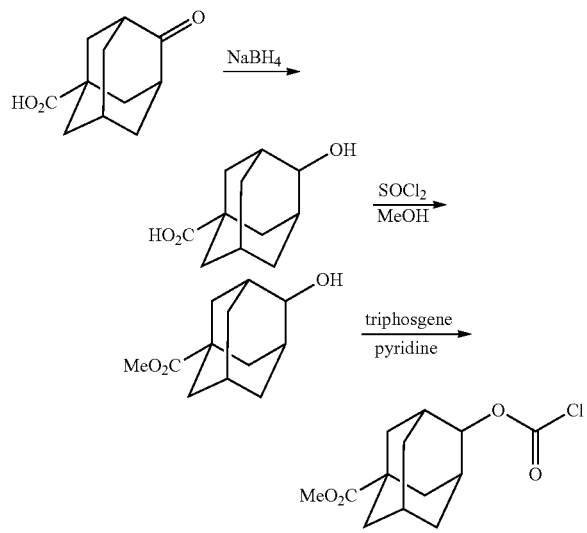

Step 1

To a stirred solution of 4-oxoadamantane-1-carboxylic acid (2.09 g, 10.8 mmol), in MeOH (100 mL), powdered NaBH$_4$ (815 mg, 21.5 mmol) was added cautiously in three portions. The mixture was stirred at rt for 1 h and concentrated under reduced pressure to remove the bulk of the methanol. The residue was diluted with 5% aq HCl (75 mL) and extracted with ether (2×100 mL). The combined ether extracts were washed with brine (25 mL) and dried over MgSO$_4$. Removal of the solvent left crude 4-hydroxy-1-adamantanecarboxylic acid (2.36 g, quant) as a white solid.

Step 2

MeOH (50 mL) was stirred and cooled in an ice bath and SOCl$_2$ (3 mL, 42 mmol) was added dropwise. The mixture was stirred for 15 min and added to a stirred suspension of crude 4-hydroxy-1-adamantanecarboxylic acid (2.36 g, 12.0 mmol) in MeOH (10 mL). The mixture was stirred overnight at rt and concentrated to leave an oil (2.46 g). Chromatography on a 40-g silica gel cartridge eluted with a gradient from 0-80% EtOAc in hexanes afforded methyl 4-hydroxyadamantane-1-carboxylate (1.88 g, 74%).

Step 3

A stirred solution of methyl 4-hydroxyadamantane-1-carboxylate (1.01 g, 4.8 mmol) and pyridine (0.38 mL, 4.8 mmol) in CH$_2$Cl$_2$ (25 mL) was cooled in an ice bath and a solution of triphosgene (0.48 g, 1.6 mmol) in CH$_2$Cl$_2$ (10 mL) was added dropwise over 15 min. The ice bath was allowed to melt and the mixture was stirred for 3 h at rt.* The mixture was evaporated to dryness and the residue was triturated with EtOAc (100 mL). The filtrate was concentrated to afford 1-(methoxycarbonyl)-4-adamantyl chloroformate (1.19 g, 91%) as an oil.

[* In some experiments the solution of 1-(methoxycarbonyl)-4-adamantyl chloroformate was used directly.]

Preparation 3

1-acetamido-4-hydroxyadamantane

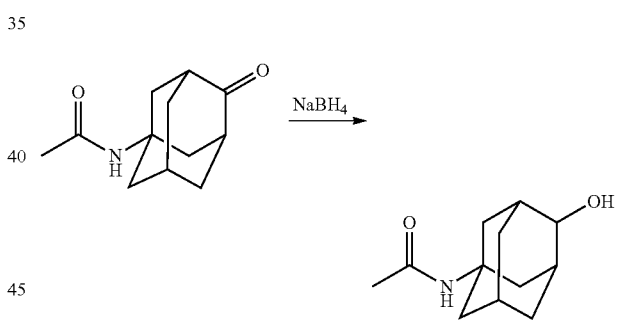

A stirred solution of 1-acetamido-4-oxoadamantane (420 mg, 2.0 mmol) in MeOH (20 mL) was cooled in an ice bath and an NaBH$_4$ caplet (1.0 g, 26 mmol) was added. The mixture was stirred over the weekend at rt and evaporated to dryness. The residue was taken up in EtOAc (90 mL), washed with 5% aq HCl (20 mL) and satd aq NaHCO$_3$ (20 mL), and dried over MgSO$_4$. Removal of the solvent left 1-acetamido-4-hydroxyadamantane (170 mg, 40%).

Preparation 4 tert-butyl 3-methylpyrrolidin-3-ylcarbamate

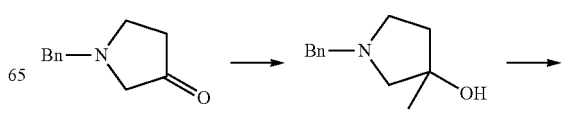

-continued

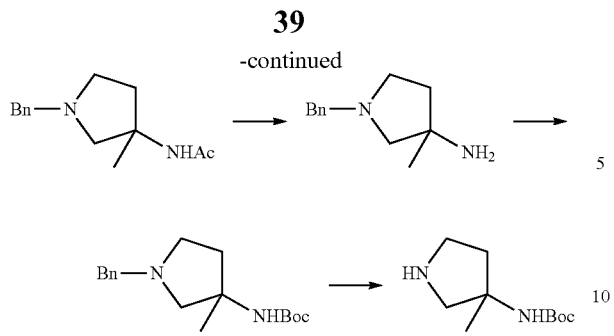

Step 1

A stirred solution of 1-benzyl-3-pyrrolidinone (8.36 g, 47.7 mmol) in dry THF (100 mL) was cooled to −70° C. and 3 M MeMgBr in ether (30 mL, 90 mmol) was added over 5 min. The cooling bath was allowed to expire and the mixture was stirred overnight at rt. The mixture was poured into satd aq $NH_4Cl$ (300 mL) and extracted with ether (3×100 mL). The combined organic extracts were washed with brine (50 mL), dried over $Na_2SO_4$ and concentrated to leave 1-benzyl-3-methylpyrrolidin-3-ol (8.98 g) as an oil.

Step 2

A solution of 1-benzyl-3-methylpyrrolidin-3-ol (5.94 g, 31.1 mmol) in MeCN (200 mL) was cooled in an ice bath and conc $H_2SO_4$ (25 mL) was added dropwise over 15 min. The ice bath was allowed to melt and the mixture was stirred at rt over the weekend. The mixture was poured onto crushed ice (600 mL). The mixture was evaporated under reduced pressure to remove MeCN. Solid $K_2CO_3$ was added in portions to the residue until it was basic. The mixture was extracted with $CH_2Cl_2$ (3×150 mL). The combined organic extracts were washed with brine (50 mL), dried over $Na_2SO_4$ and concentrated to leave N-(1-benzyl-3-methylpyrrolidin-3-yl)acetamide (4.01 g).

Step 3

A mixture of N-(1-benzyl-3-methylpyrrolidin-3-yl)acetamide (4.01 g, 17.2 mmol) and conc HCl (50 mL) was heated at reflux for 2 d. The mixture was evaporated under reduced pressure to leave 1-benzyl-3-methylpyrrolidin-3-amine dihydrochloride salt as a brown tar.

Step 4

To a stirred solution of crude 1-benzyl-3-methylpyrrolidin-3-amine dihydrochloride salt from Step 3 in THF (50 mL) and 10% aq $K_2CO_3$ (50 mL) was added di-tert-butyl dicarbonate (7.51 g, 34.5 mmol). The mixture was stirred at rt for 3 h and concentrated. The aqueous residue was extracted with $CH_2Cl_2$ (2×100 mL). The combined $CH_2Cl_2$ extracts were washed with brine (30 mL), dried over $Na_2SO_4$ and concentrated to leave a brown oil (3.80 g). Chromatography on a 40-g silica cartridge eluted with a 0-100% EtOAc in hexanes gradient afforded tert-butyl 1-benzyl-3-methylpyrrolidin-3-ylcarbamate (2.33 g).

Step 5

A solution of tert-butyl 1-benzyl-3-methylpyrrolidin-3-ylcarbamate (1.17 g, 4.0 mmol) in EtOH (40 mL) was added to 10% Pd on C and shaken under 45 psi of $H_2$ for 3 h. The mixture was filtered through Celite and concentrated to afford tert-butyl 3-methylpyrrolidin-3-ylcarbamate (0.59 g, 73%). LC-MS Method 1 $t_R$=0.72 min, m/z=201.

Preparation 5 tert-butyl 3-phenylpyrrolidin-3-ylcarbamate

The title compound was prepared following procedures analogous to those described in Preparation 4 using PhMgBr in place of MeMgBr in Step 1.

Preparation 6 tert-butyl 3-benzylpyrrolidin-3-ylcarbamate

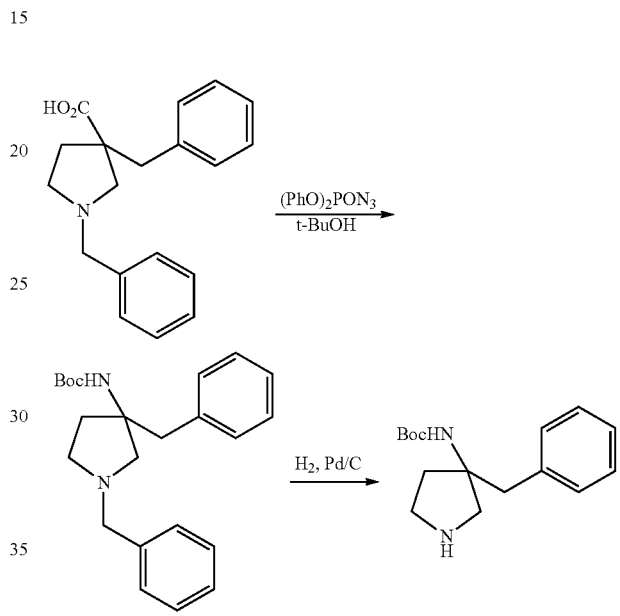

Step 1

1,3-dibenzylpyrrolidine-3-carboxylic acid HCl salt (2.13 g, 7.2 mmol) was suspended in dry t-BuOH (40 mL) and $Et_3N$ (3.0 mL, 21.6 mmol) was added followed by diphenylphosphoryl azide (1.55 mL, 7.2 mmol). The mixture was heated at reflux for 2 d. The mixture was concentrated and the residue was taken up in EtOAc (150 mL) and washed with 10% aq $Na_2CO_3$ (50 mL) and brine (50 mL). The combined aqueous washes were back extracted with EtOAc (50 mL). The combined EtOAc layers were dried over $Na_2SO_4$. Removal of the solvent left a brown syrup (3.65 g) which was purified by chromatography on a 40-g silica gel cartridge eluted with a 0-20% MeOH in $CH_2Cl_2$ gradient to afford tert-butyl 1,3-dibenzylpyrrolidin-3-ylcarbamate (1.24 g, 47%).

Step 2

A solution of tert-butyl 1,3-dibenzylpyrrolidin-3-ylcarbamate (0.62 g, 1.7 mmol) in EtOH (25 mL) and glacial HOAc (5 mL) was added to a suspension of 10% Pd on C in EtOH (25 mL). The mixture was shaken under 50 psi of $H_2$ for 5 h. The mixture was filtered through Celite and the filtrate was concentrated to afford a syrup (0.61 g) which was taken up in $CH_2Cl_2$ (90 mL), washed with 10% aq $Na_2CO_3$ (25 mL) and dried over $Na_2SO_4$. Removal of the solvent afforded tert-butyl 3-benzylpyrrolidin-3-ylcarbamate (0.31 g, 65%). LC-MS Method 1 $t_R$=1.17 min, m/z=277. This material was used without further purification.

Preparation 7

2-Adamantyl isocyanate

A vigorously stirred mixture of 2-aminoadamantane hydrochloride (5.01 g, 26.7 mmol), CH$_2$Cl$_2$ (50 mL) and satd aq NaHCO$_3$ (50 mL) was cooled in an ice bath. After 15 min, solid triphosgene (2.64 g, 8.9 mmol) was added. The mixture was stirred in the ice bath for 30 min and the layers were separated. The aqueous layer was extracted with CH$_2$Cl$_2$ (100 mL). The combined organic layers were washed with brine (50 mL), dried over MgSO$_4$ and concentrated under reduced pressure to afford the title compound (3.55 g, 75%) as a white solid.

Preparation 8

1,4-dihydroxyadamantane

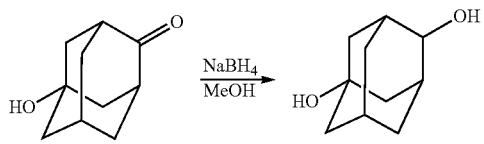

A stirred solution of 5-hydroxy-2-adamantanone (5.14 g, 30.9 mmol) in MeOH (100 mL) was cooled in an ice bath and three 1-g NaBH$_4$ caplets (3 g, 78 mmol) were added. The mixture was allowed to warm to rt and stirred overnight. The mixture was diluted with 5% aq HCl (20 mL) and concentrated to dryness. The residue was taken up in EtOAc (200 mL), washed with water (25 mL) and brine (25 mL), and dried over Na$_2$SO$_4$. Removal of the solvent left the title compound as a white solid (4.88 g, 94%) as a 1:1 mixture of cis and trans isomers.

Preparation 9

(R)-6-(pyrrolidin-3-ylamino)nicotinonitrile

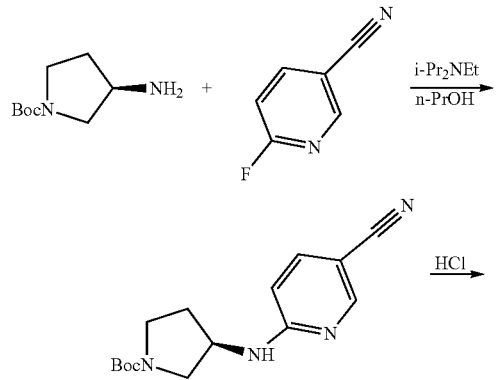

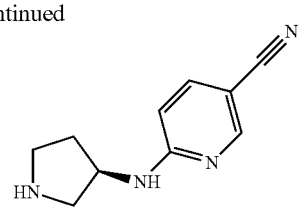

Step 1

A heavy-walled, screw-cap glass tube was charged with (R)-tert-butyl 3-aminopyrrolidine-1-carboxylate (3.30 g, 17.7 mmol), 2-fluoro-5-cyanopyridine (1.63 g, 13.2 mmol), i-Pr$_2$NEt (6.3 mL, 35.5 mmol) and n-PrOH (3 mL). The mixture was heated at 150° C. in an oil bath for 2 h. The mixture was diluted with EtOAc (180 mL), washed with 1% aq HCl (3×40 mL), satd aq NaHCO$_3$ (40 mL) and brine (40 mL), and dried over Na$_2$SO$_4$. Removal of the solvent left an oil (3.28 g) which was purified by chromatography on a 40-g silica gel cartridge eluted with a 0-100% EtOAc in hexanes gradient to afford (R)-tert-butyl 3-(5-cyanopyridin-2-ylamino)pyrrolidine-1-carboxylate (3.41 g, 88% based on 2-fluoro-5-cyanopyridine). LC-MS Method 1 $t_R$=1.57 min, m/z=289.

Step 2

A stirred solution of (R)-tert-butyl 3-(5-cyanopyridin-2-ylamino)pyrrolidine-1-carboxylate (102 mg, 0.35 mmol) in CH$_2$Cl$_2$ (3 mL) was treated with 4 M HCl in dioxane (1 mL, 4 mmol). The mixture was stirred at rt for 0.5 h. Additional 4 M HCl in dioxane was added (2 mL, 8 mmol) and stirring was continued for 1 h. The mixture was concentrated to leave (R)-6-(pyrrolidin-3-ylamino)nicotinonitrile as its dihydrochloride salt (112 mg, quant). LC-MS Method 1 $t_R$=0.53 min, m/z=189.

(R)-2-(pyrrolidin-3-ylamino)nicotinonitrile was prepared by a similar procedure using 2-fluoro-3-cyanopyridine in Step 1.

(R)-6-methyl-2-(pyrrolidin-3-ylamino)nicotinonitrile was prepared by a similar procedure using 2-chloro-3-cyano-6-methylpyridine in Step 1.

(R)-3-fluoro-N-(pyrrolidin-3-yl)pyridin-2-amine was prepared by a similar procedure using 2,3-difluoropyridine in Step 1.

Preparation 10

(R)-5-fluoro-N-(pyrrolidin-3-yl)pyridin-2-amine

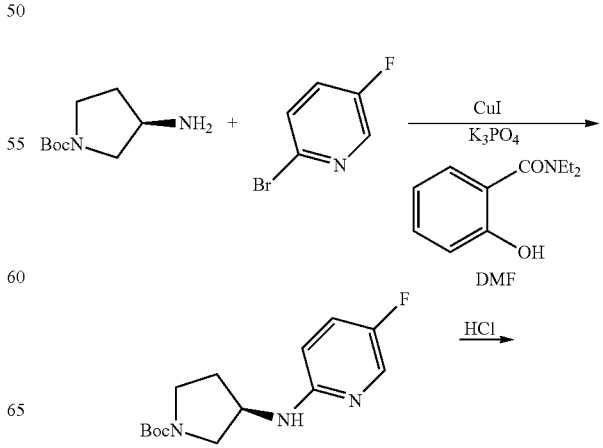

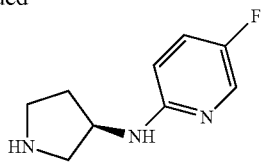

Step 1

A stirred mixture of (R)-tert-butyl 3-aminopyrrolidine-1-carboxylate (387 mg, 2.1 mmol), 2-bromo-5-fluoropyridine (366 mg, 2.1 mmol), CuI (99 mg, 0.52 mmol), $K_3PO_4$ (882 mg, 4.2 mmol), N,N-diethylsalicylamide (402 mg, 2.1 mmol) and dry DMF (2 mL) was heated at 100° C. for 3 days. The mixture was diluted with EtOAc (80 mL), washed with 1:1 $H_2O$/satd aq $NH_4Cl$ (20 mL), 1 M aq NaOH (20 mL) and brine (20 mL), and dried over $Na_2SO_4$. Removal of the solvent left a brown oil (693 mg) which was taken up in ether (100 mL) and extracted with 5% aq HCl (2×50 mL). The combined aq HCl extracts were basified with solid $K_2CO_3$ and back extracted with ether (2×60 mL). These ether extracts were combined, washed with brine, dried over $Na_2SO_4$ and concentrated to afford an oil (240 mg) which was purified by chromatography on a 12-g silica gel cartridge eluted with a 0-100% EtOAc in hexanes gradient to afford crude (R)-tert-butyl 3-(5-fluoropyridin-2-ylamino)pyrrolidine-1-carboxylate (85 mg, 14%) as an amber oil.

Step 2

Crude (R)-tert-butyl 3-(5-fluoropyridin-2-ylamino)pyrrolidine-1-carboxylate (85 mg, 0.3 mmol) was dissolved in $CH_2Cl_2$ (3 mL) and 4 M HCl in dioxane (1 mL, 4 mmol) was added. The mixture was stirred overnight at rt and concentrated to afford crude (R)-5-fluoro-N-(pyrrolidin-3-yl)pyridin-2-amine (76 mg, quant) which was used without further purification. LC-MS Method 1 $t_R$=0.42 min, m/z=182.

Preparation 11

2-chloroquinoxaline-6-carbonitrile

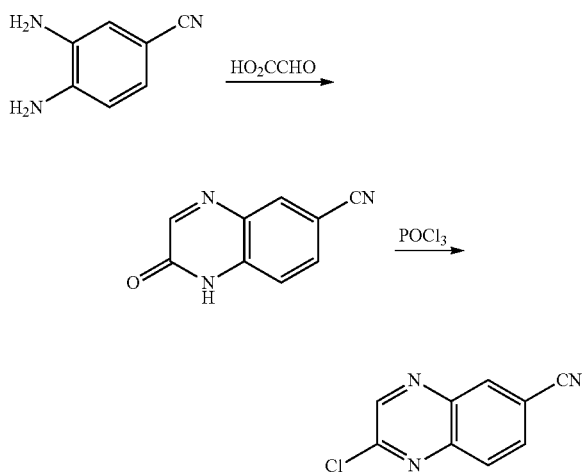

Step 1

To a stirred solution of 3,4-diaminobenzonitrile (5.00 g, 37.6 mmol) in 5% aq HCl (20 mL) was added glyoxilic acid monohydrate (4.32 g, 46.9 mmol). The mixture was stirred overnight at rt and filtered. The filter cake was washed with water and MeOH to afford 2-oxo-1,2-dihydroquinoxaline-6-carbonitrile as a grey solid which was used directly in the next step.

Step 2

2-Oxo-1,2-dihydroquinoxaline-6-carbonitrile was suspended in $POCl_3$ (25 mL) and DMF (10 drops) was added. The mixture was heated at 100° C. for 2 h, cooled and concentrated under reduced pressure to leave a black residue. The residue was dissolved in $CH_2Cl_2$ (200 mL), washed with satd aq $NaHCO_3$ (25 mL) and brine (25 mL) and dried over $Na_2SO_4$. Removal of the solvent left an off white solid (4.50 g). A 0.50-g portion was purified by chromatography on a 40-g silica gel cartridge eluted with a 0-50% EtOAc in hexanes gradient to afford 2-chloroquinoxaline-6-carbonitrile (118 mg). LC-MS Method 1 $t_R$=1.42 min, m/z=190.

EXAMPLES

Example 1

2-adamantyl 3-((tert-butoxycarbonylamino)methyl)azetidine-1-carboxylate

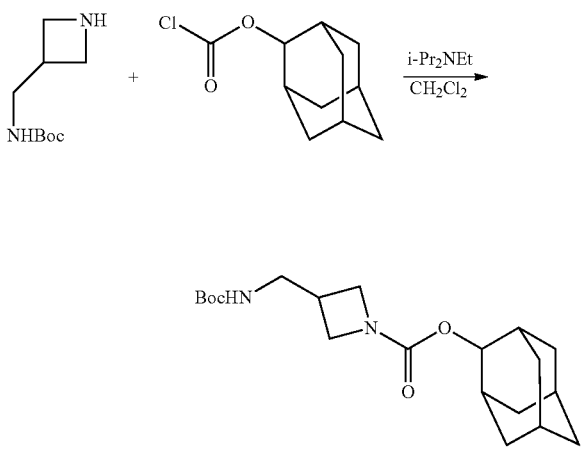

A vial was charged with tert-butyl azetidin-3-ylmethylcarbamate (25 mg, 0.12 mmol), i-$Pr_2NEt$ (31 µL, 0.17 mmol) and a flea stir bar. A solution of 2-adamantyl chloroformate in $CH_2Cl_2$ (1.5 mL, 17 mg mL$^{-1}$, 0.12 mmol) was added. The mixture was stirred overnight at rt. A 10-mL ChemElut cartridge (Varian Inc. catalog number 12198007) was wetted with 5% aq HCl (5 mL) and allowed to stand for 5 min. The reaction mixture was applied to the cartridge and eluted with ether (20 mL). The eluate was evaporated to dryness and the residue was purified by preparative HPLC to afford the title compound (10 mg, 23%). $^1$H NMR (CDCl$_3$) δ 1.42 (s, 9H), 1.5-2.0 (14H), 2.76 (m, 1H), 3.35 (m, 2H), 3.67 (m, 2H), 4.03 (m, 2H), 4.68 (m, 1H), 4.78 (s, 1H); LC-MS Method 1 $t_R$=2.08 min, m/z=387, 365, 309.

Example 2

(3R)-(2-adamantyl) 3-(tert-butoxycarbonylamino)pyrrolidine-1-carboxylate

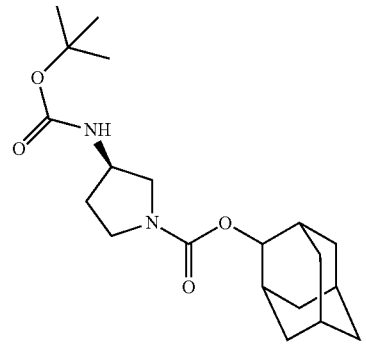 [SMILES: CC(C)(C)OC(=O)N[C@@H]1CCN(C(=O)OC2C3CC4CC(C3)CC2C4)C1]

The title compound was prepared following a procedure analogous to that described in Example 1 using (R)-tert-butyl pyrrolidin-3-ylcarbamate. $^1$H NMR (CDCl$_3$) δ 1.42 (s, 9H), 1.5-2.2 (16H), 3.26 (m, 1H), 3.49 (m, 2H), 3.67 (m, 1H), 4.22 (1H), 4.63 (1H), 4.83 (s, 1H); LC-MS Method 1 $t_R$=2.12 min, m/z=387, 365, 309.

Example 3

(R)-(2-adamantyl) 3-(ethoxycarbonylamino)pyrrolidine-1-carboxylate

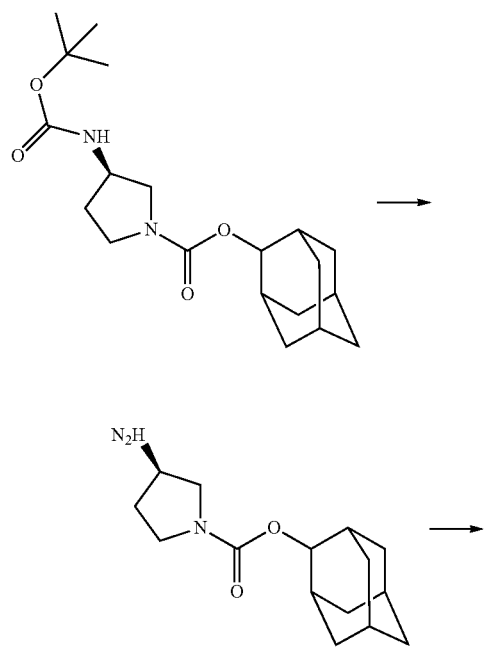

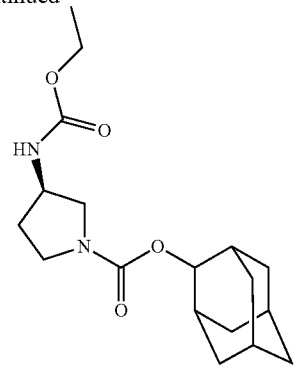

Step 1

To (3R)-(2-adamantyl) 3-(tert-butoxycarbonylamino)pyrrolidine-1-carboxylate (0.43 g, 1.18 mmol) was added 4 M HCl in dioxane (5 mL, 20 mmol). The mixture was stirred at rt for 1 h and concentrated to afford (R)-2-adamantyl 3-aminopyrrolidine-1-carboxylate HCl salt (0.45 g) as a white solid.

Step 2

A 1.5 dram vial equipped with a flea stirbar was charged with (R)-2-adamantyl 3-aminopyrrolidine-1-carboxylate HCl salt (30 mg, 0.10 mmol), i-Pr$_2$NEt (72 μL, 0.4 mmol) and CH$_2$Cl$_2$ (1 mL). Ethyl chloroformate (15 mL, 0.123 mmol) was added. The mixture was stirred at rt overnight and applied to a 10-mL Chem-Elut cartridge prewetted with 5% aq HCl (6 mL). The cartridge was eluted with ether (20 mL). The eluate was evaporated to dryness and the residue was purified by prep HPLC to afford (R)-(2-adamantyl) 3-(ethoxycarbonylamino)pyrrolidine-1-carboxylate (24 mg, 71%). LC-MS Method 1 $t_R$=1.88 min, m/z=337; $^1$H NMR (CDCl$_3$) 1.27 (t, 3H), 1.58 (d, 2H), 1.70-2.00 (13H), 2.19 (m, 1H), 3.13 (1H), 3.26 (dd, 1H), 3.59 (m, 2H), 3.70 (m, 1H), 4.17 (d, 1H), 4.29 (1H), 4.78 (1H), 4.82 (s, 1H)

Example 4

(R)-(2-adamantyl) 3-(isopropoxycarbonylamino)pyrrolidine-1-carboxylate

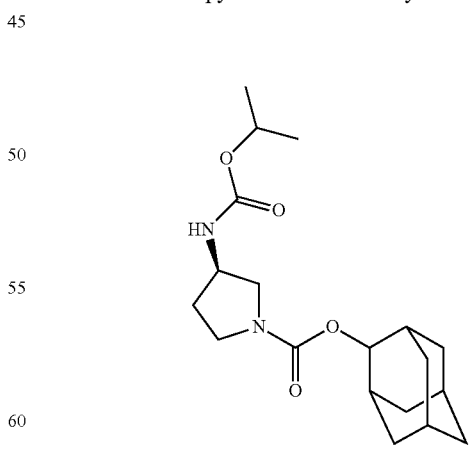

The title compound was prepared from (R)-2-adamantyl 3-aminopyrrolidine-1-carboxylate HCl salt and isopropyl chloroformate following a procedure analogous to that described in Example 3 Step 2. LC-MS Method 1 $t_R$=1.98 min, m/z=351; $^1$H NMR (CDCl$_3$) 1.24 (d, 6H), 1.57 (d, 2H), 1.70-2.00 (13H), 2.18 (m, 1H), 3.16 (1H), 3.49 (m, 2H), 3.69 (m, 1H), 4.24 (m, 1H), 4.74 (1H), 4.82 (s, 1H), 4.93 (m, 1H)

Example 5

(R)-(2-adamantyl) 3-(propoxycarbonylamino)pyrrolidine-1-carboxylate

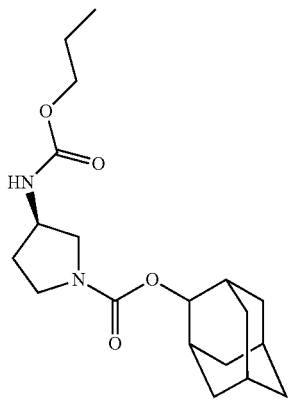 [SMILES: CCCOC(=O)N[C@@H]1CCN(C(=O)OC2C3CC4CC(C3)CC2C4)C1]

The title compound was prepared from (R)-2-adamantyl 3-aminopyrrolidine-1-carboxylate HCl salt and propyl chloroformate following a procedure analogous to that described in Example 3 Step 2. LC-MS Method 1 $t_R$=2.00 min, m/z=351; $^1$H NMR (CDCl$_3$) 0.97 (t, 3H), 1.50-2.05 (16H), 2.19 (m, 1H), 2.42 (1H), 3.29 (dd, 1H), 3.50 (m, 2H), 3.70 (m, 1H), 4.04 (m, 2H), 4.28 (1H), 4.78 (1H), 4.83 (s, 1H)

Example 6

(R)-(2-adamantyl) 3-(isobutoxycarbonylamino)pyrrolidine-1-carboxylate

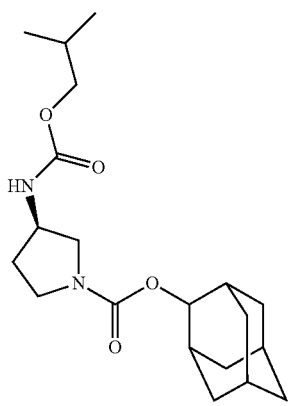

The title compound was prepared from (R)-2-adamantyl 3-aminopyrrolidine-1-carboxylate HCl salt and isobutyl chloroformate following a procedure analogous to that described in Example 3 Step 2. LC-MS Method 1 $t_R$=2.1 min, m/z=365; $^1$H NMR (CDCl$_3$) 0.97 (d, 6H), 1.58 (d, 2H), 1.70-2.05 (14H), 2.18 (m, 1H), 2.80 (1H), 3.29 (dd, 1H), 3.53 (m, 2H), 3.70 (m, 1H), 3.84 (m, 1H), 4.28 (1H), 4.80 (1H), 4.83 (s, 1H)

Example 7

(1S,4S)-2-tert-butyl 5-(2-adamantyl)-2,5-diazabicyclo[2.2.1]heptane-2,5-dicarboxylate

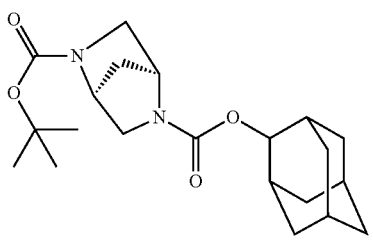 [SMILES: CC(C)(C)OC(=O)N1C[C@@H]2C[C@H]1CN2C(=O)OC1C2CC3CC(C2)CC1C3]

The title compound was prepared following a procedure analogous to that described in Example 1 using (1S,4S)-tert-butyl 2,5-diazabicyclo[2.2.1]heptane-2-carboxylate. $^1$H NMR (CDCl$_3$) δ 1.44 (9H), 1.5-2.1 (16H), 3.25-3.55 (3H), 4.4-4.9 (4H); LC-MS Method 1 $t_R$=2.22 min, m/z=399, 377, 321.

Example 8

(3R)-(2-adamantyl) 3-(tert-butoxycarbonylamino)piperidine-1-carboxylate

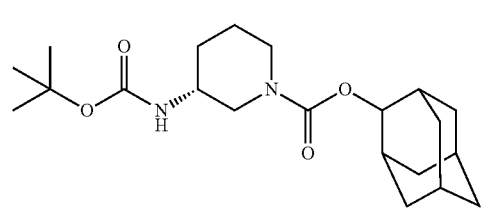 [SMILES: CC(C)(C)OC(=O)N[C@@H]1CCCN(C(=O)OC2C3CC4CC(C3)CC2C4)C1]

The title compound was prepared using a procedure analogous to that described in Example 1 using (R)-tert-butyl piperidin-3-ylcarbamate. $^1$H NMR (CDCl$_3$) δ 1.42 (s, 9H), 1.5-2.1 (17H), 2.4 (3H), 3.2-4.0 (3H), 4.67 (1H), 4.85 (s, 1H); LC-MS Method 1 $t_R$=2.22 min, m/z=401, 379, 323.

Example 9

2-adamantyl 3-(tert-butoxycarbonyl(methyl)amino)pyrrolidine-1-carboxylate

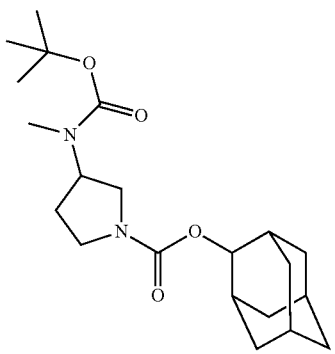 [SMILES: CN(C(=O)OC(C)(C)C)C1CCN(C(=O)OC2C3CC4CC(C3)CC2C4)C1]

Method 1

(±)-2-adamantyl 3-(tert-butoxycarbonyl(methyl)amino)pyrrolidine-1-carboxylate was prepared following a procedure analogous to that described in Example 1 using (±)-tert-butyl methyl(pyrrolidin-3-yl)carbamate. $^1$H NMR (CDCl$_3$) δ 1.48 (s, 9H), 1.5-2.1 (15H), 2.79 (s, 3H), 3.15 (1H), 3.28 (2H), 3.39 (1H), 3.61 (1H), 4.74 (1H), 4.84 (s, 1H); LC-MS Method 1 $t_R$=2.28 min, m/z=401, 379, 323.

Method 2

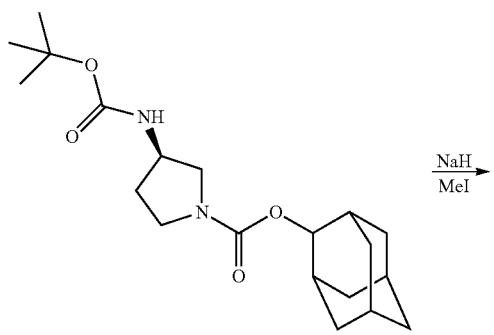

(R) 2-adamantyl 3-(tert-butoxycarbonyl(methyl)amino)pyrrolidine-1-carboxylate was prepared as follows. A vial equipped with a flea stirbar was charged with (3R)-(2-adamantyl) 3-(tert-butoxycarbonylamino)pyrrolidine-1-carboxylate (105 mg, 0.29 mmol), methyl iodide (36 μL, 0.58 mmol) and dry THF (1 mL). 60% NaH in oil (14 mg, 0.58 mmol) was added and the mixture was stirred overnight under N$_2$. The mixture was heated at 50° C. for 1 h, cooled and applied to a 10-mL ChemElut cartridge, prewetted with 5% aq HCl (6 mL), and eluted with ether (20 mL). The eluate was concentrated and the residue was purified by preparative HPLC to afford (R) 2-adamantyl 3-(tert-butoxycarbonyl(methyl)amino)pyrrolidine-1-carboxylate (32 mg, 29%).

Example 10

(3R)-(2-adamantyl) 3-(benzyloxycarbonylamino)pyrrolidine-1-carboxylate

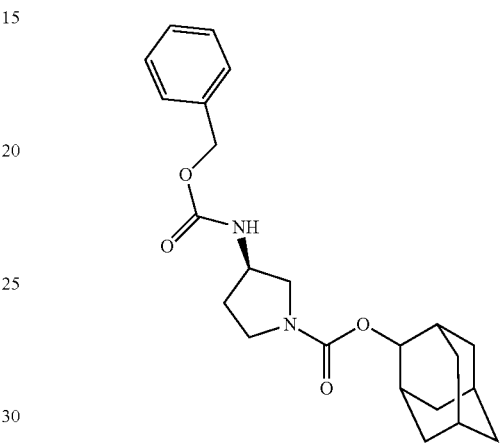

The title compound was prepared following a procedure analogous to that described in Example 1 using (R)-benzyl pyrrolidin-3-ylcarbamate. $^1$H NMR (CDCl$_3$) δ 1.5-2.2 (16H), 3.11 (s, 1H), 3.28 (dd, 1H), 3.49 (m, 1H), 3.68 (m, 1H), 4.30 (m, 1H), 4.82 (s, 1H), 4.97 (m, 1H), 5.08 (s, 2H), 7.36 (5H); LC-MS Method 1 $t_R$=2.10 min, m/z=421, 399.

Example 11

(±)-1-tert-butyl 5-(2-adamantyl) hexahydropyrrolo[3,4-b]pyrrole-1,5-dicarboxylate

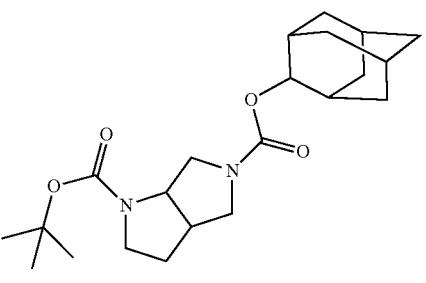 [SMILES: CC(C)(C)OC(=O)N1CCC2CN(C(=O)OC3C4CC5CC(C4)CC3C5)CC21]

The title compound was prepared following a procedure analogous to that described in Example 1 using (±)-tert-butyl hexahydropyrrolo[2,3-c]pyrrole-1(2H)-carboxylate. $^1$H NMR (CDCl$_3$) δ 1.43 (s, 9H), 1.5-2.1 (17H), 2.92 (1H), 3.27 (m, 1H), 3.4-3.7 (3H), 4.19 (0.5H), 4.29 (0.5H), 3.38 (s, 1H), 4.82 (s, 1H); LC-MS Method 1 $t_R$=2.28 min, m/z=413, 391, 291.

Example 12

(R)-(2-adamantyl) 3-(benzyl(tert-butoxycarbonyl)amino)pyrrolidine-1-carboxylate

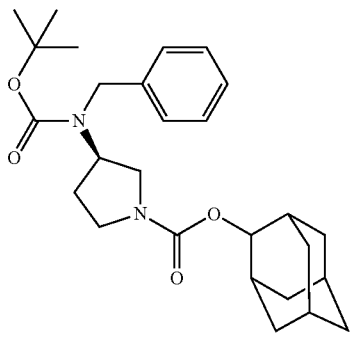 [SMILES: CC(C)(C)OC(=O)N(Cc1ccccc1)[C@@H]1CCN(C(=O)OC2C3CC4CC(C3)CC2C4)C1]

The title compound was prepared following a procedure analogous to that described in Example 9 Method 2 using benzyl bromide in place of methyl iodide. $^1$H NMR (CDCl$_3$) 1.41 (9H), 1.53 (d, 2H), 1.70-2.05 (14H), 3.27 (m, 2H), 3.57 (m, 1H), 3.60 (m, 1H), 3.71 (1H), 4.42 (2H), 4.80 (s, 1H), 7.10-7.30 (5H)

Example 13

(2-adamantyl) 3-(tert-butoxycarbonylamino)-3-phenylpyrrolidine-1-carboxylate The title compound was prepared following a procedure analogous to that described in Example 1 using tert-butyl 3-phenylpyrrolidin-3-ylcarbamate. LC-MS Method 1 $t_R$=2.35 min, m/z=463, 441, 385; $^1$H NMR (CDCl$_3$) 1.35 (9H), 1.55 (d, 2H), 1.70-2.05 (13H), 2.28 (m, 1H), 3.59 (m, 2H), 3.80 (m, 1H), 3.98 (1H), 4.86 (s, 1H), 5.02 (1H), 7.35 (5H)

Example 14

(R)-(1-(methoxycarbonyl)-4-adamantyl) 3-(tert-butoxycarbonylamino)pyrrolidine-1-carboxylate

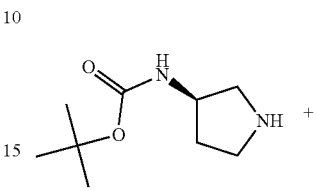

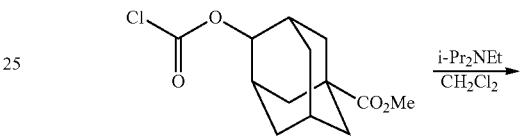

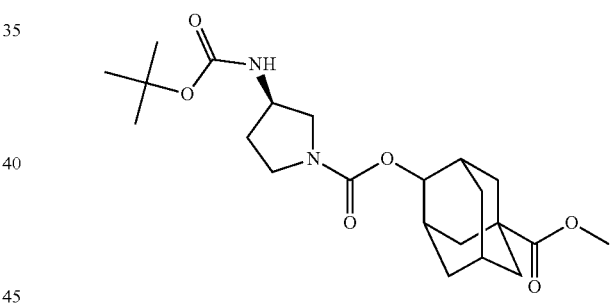

A stirred solution of 1-(methoxycarbonyl)-4-adamantyl chloroformate (455 mg, 1.67 mmol) in CH$_2$Cl$_2$ (25 mL) was cooled in an ice bath and (R)-tert-butyl pyrrolidin-3-ylcarbamate (310 mg, 1.67 mmol) was added, followed by i-Pr$_2$NEt (0.60 mL, 3.4 mmol). The ice bath was allowed to melt and the mixture was stirred overnight at rt. The mixture was diluted with ether (75 mL), washed with 5% aq HCl (20 mL) and satd aq NaHCO$_3$ (20 mL), and dried over MgSO$_4$. Removal of the solvent left an oil (776 mg). Chromatography on a 40-g silica gel cartridge eluted with a 0-100% EtOAc in hexanes gradient afforded (R)-(1-(methoxycarbonyl)-4-adamantyl) 3-(tert-butoxycarbonylamino)pyrrolidine-1-carboxylate (499 mg, 71%) as an oil. $^1$H NMR (CDCl$_3$) δ 1.43 (s, 9H), 1.5-2.3 (15H), 3.23 (m, 1H), 3.47 (m, 2H), 3.64 (4H), 4.22 (1H), 4.7-4.9 (2H); LC-MS Method 1 $t_R$=1.87 min, m/z=446, 423, 323.

Example 15

(3R)-(1-(hydroxymethyl)-4-adamantyl) 3-(tert-butoxycarbonylamino)pyrrolidine-1-carboxylate

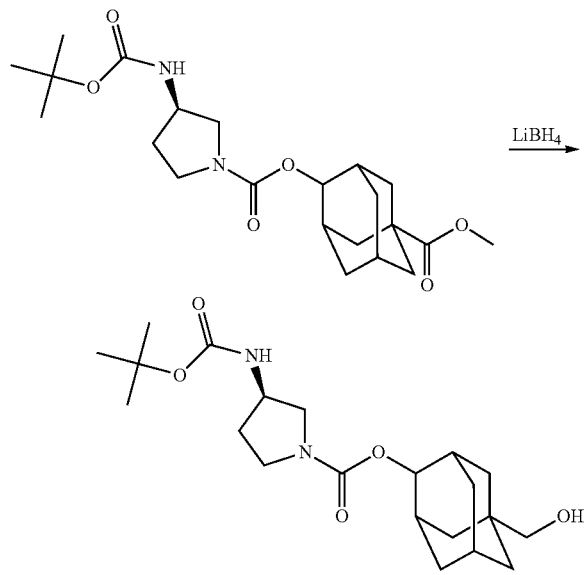

A stirred solution of (R)-(1-(methoxycarbonyl)-4-adamantyl) 3-(tert-butoxycarbonylamino)pyrrolidine-1-carboxylate (77 mg, 0.18 mmol) and MeOH (3.7 µL, 0.09 mmol) in dry THF (2.5 mL) was cooled in an ice bath and solid LiBH$_4$ (8.0 mg, 0.36 mmol) was added. The mixture was stirred in the ice bath for 1 h and at rt for 3.5 h. Additional LiBH$_4$ (16 mg, 0.72 mmol) was added and stirring was continued overnight. The mixture was diluted with 5% aq HCl (30 mL) and extracted with ether (2×50 mL). The combined ether extracts were washed with satd aq NaHCO$_3$ (15 mL), dried over MgSO$_4$ and rotovaped to leave an oil which was purified by preparative HPLC to afford two isomeric products.

Isomer 1 (29 mg). $^1$H NMR (CDCl$_3$) δ 1.43 (s, 9H), 1.5-2.2 (16H), 3.22 (3H), 3.49 (2H), 3.65 (m, 1H), 4.22 (m, 1H), 4.61 (m, 1H), 4.8 (s, 1H); LC-MS Method 1 t$_R$=1.53 min, m/z=395, 339.

Isomer 2 (14 mg). $^1$H NMR (CDCl$_3$) δ 1.44 (s, 9H), 1.5-2.2 (16H), 3.23 (s, 2H), 3.28 (1H), 3.50 (m, 2H), 3.68 (m, 1H), 4.21 (1H), 4.67 (1H), 4.80 (s, 1H); LC-MS Method 1 t$_R$=1.60 min, m/z=395, 339.

Example 16

(3R) (1-carbamoyl-4-adamantyl) 3-(tert-butoxycarbonylamino)pyrrolidine-1-carboxylate

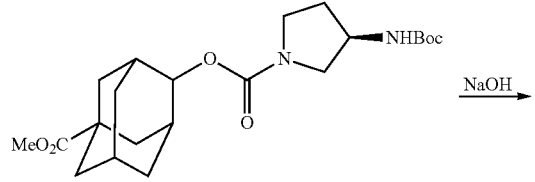

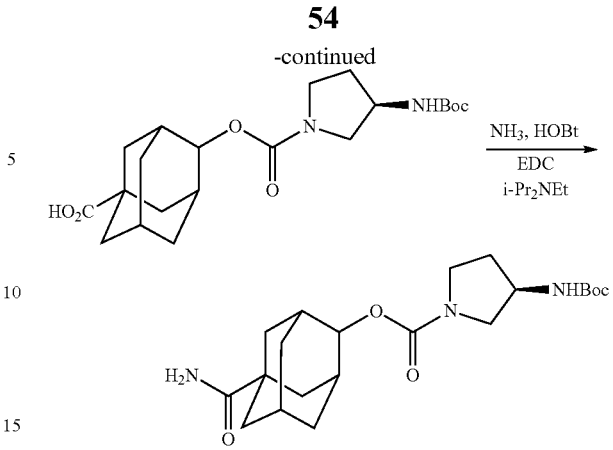

Step 1

To a stirred solution of (3R)-(1-(methoxycarbonyl)-4-adamantyl) 3-(tert-butoxycarbonylamino)pyrrolidine-1-carboxylate (352 mg, 0.83 mmol) in THF (2 mL) and MeOH (4 mL) was added 1 M aq NaOH (2 mL, 2.0 mmol). The mixture was stirred at rt for 2 d and evaporated to remove organic solvents. The aqueous residue was partitioned between EtOAc (2×50 mL) and 5% aq HCl (40 mL). The combined organic layers were dried over MgSO$_4$ and concentrated to afford (R)-4-(3-(tert-butoxycarbonylamino)pyrrolidine-1-carbonyloxy)adamantane-1-carboxylic acid (347 mg, quant) as an oil.

Step 2

To a stirred solution of (R)-4-(3-(tert-butoxycarbonylamino)pyrrolidine-1-carbonyloxy)adamantane-1-carboxylic acid (97 mg, 0.24 mmol), HOBt (73 mg, 0.47 mmol) and i-Pr$_2$NEt (0.10 mL, 0.50 mmol) in CH$_2$Cl$_2$ (5 mL) was added 0.5 M NH$_3$ in dioxane (1 mL, 0.50 mmol) followed by solid EDC.HCl (91 mg, 0.47 mmol). The mixture was stirred overnight at rt, diluted with EtOAc (100 mL), washed with 5% aq HCl (15 mL) and satd aq NaHCO$_3$ (15 mL), and dried over MgSO$_4$. Removal of the solvent left an oil (91 mg) which was purified by preparative HPLC to give two isomers of (3R) (1-carbamoyl-4-adamantyl) 3-(tert-butoxycarbonylamino)pyrrolidine-1-carboxylate.

Example 16 Isomer 1: (3R) (cis-1-carbamoyl-4-adamantyl) 3-(tert-butoxycarbonylamino)pyrrolidine-1-carboxylate (27 mg): LC-MS Method 1 t$_R$=1.37 min, m/z=408, 352, 308; $^1$H NMR (CD$_3$OD) 1.46 (s, 9H), 1.60-2.20 (15H), 3.2-3.7 (4H), 4.10 (m, 1H), 4.74 (s, 1H)

Example 16 Isomer 2: (3R) (trans-1-carbamoyl-4-adamantyl) 3-(tert-butoxycarbonylamino)pyrrolidine-1-carboxylate (24 mg): LC-MS Method 1 t$_R$=1.43 min, m/z=408, 352, 308; $^1$H NMR (CD$_3$OD) 1.43 (s, 9H), 1.58 (d, 2H), 1.80-2.20 (13H), 3.2-3.7 (4H), 4.08 (m, 1H), 4.78 (s, 1H)

Example 17

1-carbamoyl-4-adamantyl 3-((tert-butoxycarbonylamino)methyl)azetidine-1-carboxylate

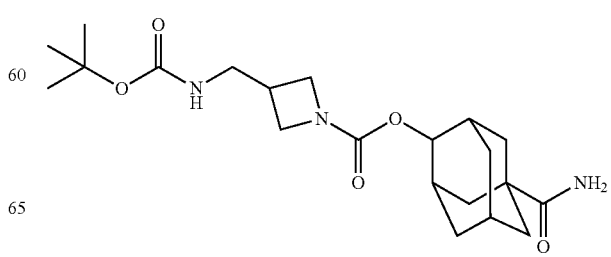

The title compound was prepared by a procedure analogous to that described in Example 16 using tert-butyl azetidin-3-ylmethylcarbamate in Step 1. Two isomers were separated by preparative HPLC.

Isomer 1: (cis-1-carbamoyl-4-adamantyl) 3-((tert-butoxycarbonylamino)methyl)azetidine-1-carboxylate. LC-MS Method 1 $t_R$=1.33 min, m/z=408, 352, 308.

Isomer 2: (trans-1-carbamoyl-4-adamantyl) 3-((tert-butoxycarbonylamino)methyl)azetidine-1-carboxylate. LC-MS Method 1 $t_R$=1.42 min, m/z=408, 352, 308; $^1$H NMR (CDCl$_3$) 1.43 (s, 9H), 1.50 (d, 2H), 1.85-2.05 (9H), 2.12 (s, 2H), 2.77 (m, 1H), 3.36 (m, 2H), 3.69 (2H), 4.08 (m, 2H), 4.75 (1H), 4.79 (1H), 5.83 (1H), 6.20 (1H).

Example 18

(1-carbamoyl-4-adamantyl) (3R-(isobutoxycarbonylamino)pyrrolidine-1-carboxylate)

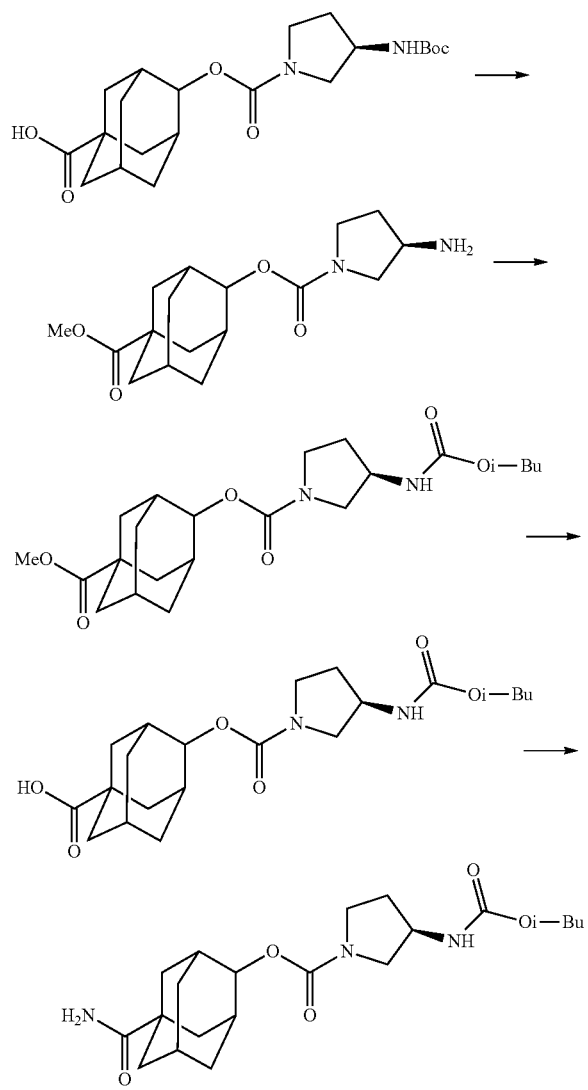

Step 1

To a stirred solution of (R)-4-(3-(tert-butoxycarbonylamino)pyrrolidine-1-carbonyloxy)adamantane-1-carboxylic acid (600 mg, 1.5 mmol) in MeOH (30 mL) was added 4 M HCl in dioxane (10 mL, 40 mmol). The mixture was stirred at rt for 18 h. The mixture was concentrated to afford (3R)-(1-(methoxycarbonyl)-4-adamantyl) 3-aminopyrrolidine-1-carboxylate HCl salt as a syrup.

Step 2

To a stirred, ice-cold solution of (3R)-(1-(methoxycarbonyl)-4-adamantyl) 3-aminopyrrolidine-1-carboxylate HCl salt (200 mg, 0.56 mmol) and i-Pr$_2$NEt (0.45 mL, 2.5 mmol) in CH$_2$Cl$_2$ (10 mL) was added dropwise over 2 min a solution of isobutyl chloroformate (0.08 mL, 0.62 mmol) in CH$_2$Cl$_2$ (5 mL). The mixture was allowed to warm to rt and stirred overnight. The mixture was diluted with ether (80 mL), washed with 5% aq HCl (20 mL) and satd aq NaHCO$_3$ (20 mL), and dried over MgSO$_4$. Removal of the solvent left (3R) (1-(methoxycarbonyl)-4-adamantyl) 3-(isobutoxycarbonylamino)pyrrolidine-1-carboxylate (269 mg) as an oil.

Step 3

To a stirred solution of (3R) (1-(methoxycarbonyl)-4-adamantyl) 3-(isobutoxycarbonylamino)pyrrolidine-1-carboxylate (130 mg, 0.28 mmol) in THF (5 mL) and MeOH (10 mL) was added 5% aq NaOH (5 mL). The mixture was stirred at rt for 3 d. The mixture was concentrated under reduced pressure, diluted with water (15 mL) and washed with ether (80 mL). The aqueous layer was diluted with 10% aq citric acid (30 mL) and extracted with EtOAc (3×40 mL). The combined organic extracts were dried over MgSO$_4$ and concentrated to leave (3R)-4-(3-(isobutoxycarbonylamino)pyrrolidine-1-carbonyloxy)adamantane-1-carboxylic acid (178 mg) as an oil.

Step 4

To a stirred mixture of (3R)-4-(3-(isobutoxycarbonylamino)pyrrolidine-1-carbonyloxy)adamantane-1-carboxylic acid (178 mg, 0.28 mmol), HOBt (94 mg, 0.61 mmol) and i-Pr$_2$NEt (0.165 mL, 0.92 mmol) and 0.5 M NH$_3$ in dioxane (1.25 mL, 0.62 mmol) was added solid EDC.HCl (118 mg, 0.61 mmol). The mixture was stirred at rt for 18 h, diluted with EtOAc (80 mL), washed with 5% aq HCl (2×15 mL) and satd aq NaHCO$_3$ (15 mL), and dried over MgSO$_4$. Removal of the solvent left an oil (63 mg) which was purified by preparative HPLC to afford two isomers.

Isomer 1: (cis-1-carbamoyl-4-adamantyl) (3R-(isobutoxycarbonylamino)pyrrolidine-1-carboxylate) LC-MS Method 1 $t_R$=1.37 min, m/z=408.

Isomer 2: (trans-1-carbamoyl-4-adamantyl) (3R-(isobutoxycarbonylamino)pyrrolidine-1-carboxylate). LC-MS Method 1 $t_R$=1.45 min, m/z=408; $^1$H NMR (CDCl$_3$) 0.92 (d, 6H), 1.55 (d, 2H), 1.80-2.25 (14H), 3.28 (dd, 1H), 3.50 (2H), 3.70 (m, 1H), 4.84 (2H), 4.29 (1H), 4.79 (d, 1H), 4.83 (s, 1H), 5.70 (1H), 5.80 (1H).

Example 19

(R)-(1-cyano-4-adamantyl) 3-(tert-butoxycarbonylamino)pyrrolidine-1-carboxylate

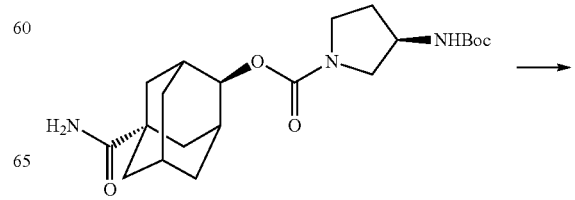

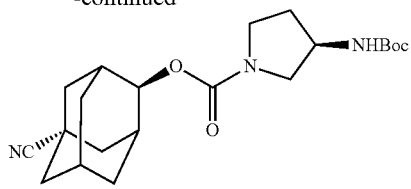

A stirred solution of (3R) (trans-1-carbamoyl-4-adamantyl) 3-(tert-butoxycarbonylamino)pyrrolidine-1-carboxylate (10.8 mg, 0.027 mmol) and pyridine (0.010 mL, 0.11 mmol) in $CH_2Cl_2$ (1 mL) was cooled in an ice bath and trifluoroacetic anhydride (0.04 mL, 0.029 mmol) was added. The mixture was stirred for 1 h. A second aliquot of trifluoroacetic anhydride (0.04 mL, 0.029 mmol) was added and stirring was continued overnight. The mixture was concentrated and the residue was purified by preparative HPLC to afford (R)-(trans-1-cyano-4-adamantyl) 3-(tert-butoxycarbonylamino)pyrrolidine-1-carboxylate (4.8 mg, 49%) as an oil. LC-MS Method 1 $t_R$=1.75 min, m/z=390, 334, 290; $^1$H NMR ($CDCl_3$) 1.45 (s, 9H), 1.55 (d, 2H), 1.84 (m, 2H), 1.95-2.20 (11H), 3.26 (m, 1H), 3.48 (m, 2H), 3.64 (m, 1H), 4.22 (1H), 4.63 (1H), 4.82 (s, 1H)

Example 20

(R)-1-acetamido-4-adamantyl 3-(tert-butoxycarbonylamino)pyrrolidine-1-carboxylate

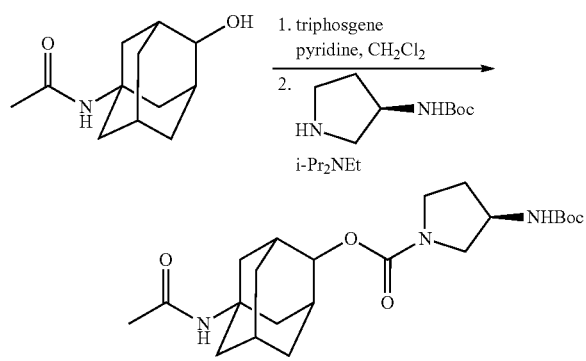

A stirred solution of 1-acetamido-4-hydroxyadamantane (170 mg, 0.81 mmol) and pyridine (0.10 mL, 1.2 mmol) in $CH_2Cl_2$ (16 mL) was cooled in an ice bath and a solution of triphosgene (80 mg, 0.27 mmol) in $CH_2Cl_2$ (4 mL) was added. The mixture was stirred in the ice bath for 2 h. A 5-mL aliquot of this solution (0.20 mmol) was added to a stirred solution of (R)-3-(t-butoxycarbonylamino)pyrrolidine (45 mg, 0.24 mmol) and i-$Pr_2NEt$ (0.10 mL, 0.75 mmol) in $CH_2Cl_2$ (2 mL). The mixture was stirred overnight at rt, diluted with ether (50 mL), washed with 5% aq HCl (20 mL) and satd aq $NaHCO_3$ (20 mL), and dried over $MgSO_4$. Removal of the solvent left a white solid (43 mg) which was purified by preparative HPLC to give two isomers.

Example 20 Isomer 1: LC-MS Method 1 $t_R$=1.45 min, m/z=422, 366.

Example 20 Isomer 2: LC-MS Method 1 $t_R$=1.52 min, m/z=422, 366, 322; $^1$H NMR ($CDCl_3$) 1.45 (s, 9H), 1.52 (d, 2H), 1.80-2.20 (16H), 3.24 (dd, 1H), 3.49 (m, 2H), 3.68 (m, 1H), 4.22 (1H), 4.61 (1H), 4.86 (s, 1H), 5.17 (s, 1H).

Example 21

(R) (1-carbamoyl-4-adamantyl) 3-(tert-butoxycarbonyl(methyl)amino)pyrrolidine-1-carboxylate

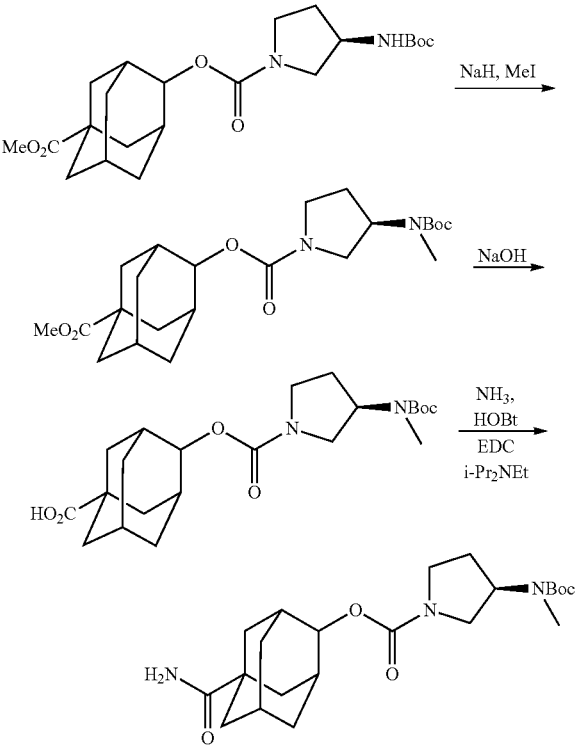

The title compound was prepared using a procedure analogous to that described in Example 9 Method 2, followed by procedures analogous to those described in Example 16 Steps 1 and 2. Preparative HPLC afforded two isomers.

Example 21 Isomer 1: (R) (cis-1-carbamoyl-4-adamantyl) 3-(tert-butoxycarbonyl(methyl)amino)pyrrolidine-1-carboxylate. LC-MS Method 1 $t_R$=1.42 min, m/z=422; $^1$H NMR ($CDCl_3$) selected resonances: 1.47 (s, 9H), 1.79 (s, 3H), 4.79 (m, 2H), 5.87 (br s, 1H), 6.76 (br s, 1H).

Example 21 Isomer 2: (R) (trans-1-carbamoyl-4-adamantyl) 3-(tert-butoxycarbonyl(methyl)amino)pyrrolidine-1-carboxylate. LC-MS Method 1 $t_R$=1.53 min, m/z=422; $^1$H NMR ($CDCl_3$) selected resonances: 1.47 (s, 9H), 2.79 (s, 3H), 4.79 (m, 2H), 5.92 (br s, 1H), 7.03 (m, 1H).

Example 22

1-carbamoyl-4-adamantyl 3-(tert-butoxycarbonylamino)-3-methylpyrrolidine-1-carboxylate

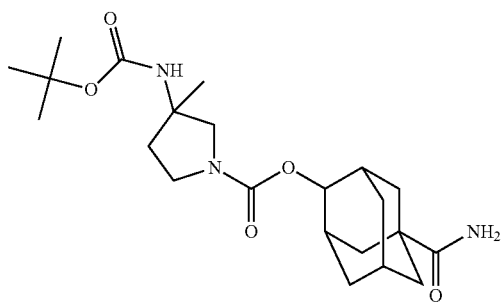 [SMILES: CC1(NC(=O)OC(C)(C)C)CCN(C(=O)OC2C3CC4CC2CC(C(N)=O)(C4)C3)C1]

The title compound was prepared by a procedure analogous to that described in Example 14 using tert-butyl 3-methylpyrrolidin-3-ylcarbamate, followed by procedures analogous to those described in Example 16. Two isomers were separated by preparative HPLC.

Isomer 1: (cis-1-carbamoyl-4-adamantyl) 3-(tert-butoxycarbonylamino)-3-methylpyrrolidine-1-carboxylate. LC-MS Method 1 $t_R$=1.42 min, m/z=422, 366, 322.

Isomer 2: (trans-1-carbamoyl-4-adamantyl) 3-(tert-butoxycarbonylamino)-3-methylpyrrolidine-1-carboxylate. LC-MS Method 1 $t_R$=1.47 min, m/z=422, 366, 322.

Isomer 2 (7.9 mg) was further fractionated by chromatography on a Chiralpak IA column eluted with 80:20 hexanes/EtOH to afford two enantiomers.

Isomer 2.1 (3.0 mg): LC-MS Method 2 $t_R$=6.53 min, m/z=422, 366, 322.

Isomer 2.2 (3.2 mg): LC-MS Method 2 $t_R$=6.53 min, m/z=422, 366, 322.

Example 23

1-tert-butyl 5-(1-carbamoyl-4-adamantyl)hexahydropyrrolo[3,4-b]pyrrole-1,5-dicarboxylate

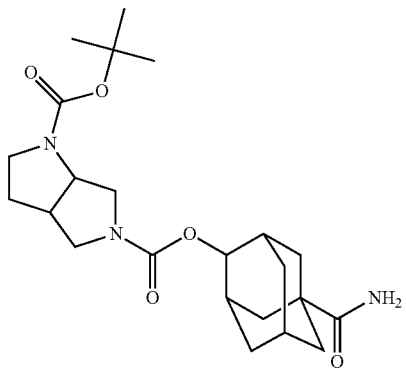 [SMILES: CC(C)(C)OC(=O)N1CCC2CN(C(=O)OC3C4CC5CC3CC(C(N)=O)(C5)C4)CC21]

The title compound was prepared by a procedure analogous to that described in Example 14 using tert-butyl hexahydropyrrolo[3,4-b]pyrrole-1(2H)-carboxylate, followed by procedures analogous to those described in Example 16. Two isomers were separated by preparative HPLC.

Isomer 1: 1-tert-butyl 5-(cis-1-carbamoyl-4-adamantyl) hexahydropyrrolo[3,4-b]pyrrole-1,5-dicarboxylate. LC-MS Method 1 $t_R$=1.43 min, m/z=434, 378, 334.

Isomer 2: 1-tert-butyl 5-(trans-1-carbamoyl-4-adamantyl) hexahydropyrrolo[3,4-b]pyrrole-1,5-dicarboxylate. LC-MS Method 1 $t_R$=1.52 min, m/z=434, 378, 334.

Example 24

(R)-(1-carbamoyl-4-adamantyl) 3-(isopropoxycarbonylamino)pyrrolidine-1-carboxylate

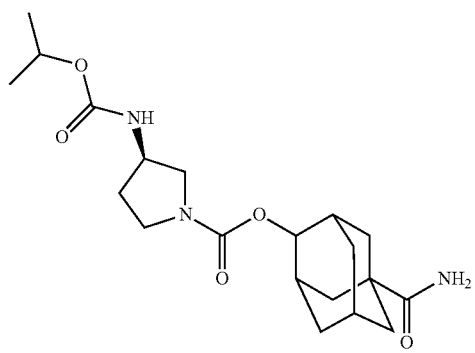 [SMILES: CC(C)OC(=O)N[C@@H]1CCN(C(=O)OC2C3CC4CC2CC(C(N)=O)(C4)C3)C1]

The title compound was prepared following procedures analogous to those described in Example 18 using isopropyl chloroformate in Step 2. Two isomers were separated by preparative HPLC.

Isomer 1: (R)-(cis-1-carbamoyl-4-adamantyl) 3-(isopropoxycarbonylamino)pyrrolidine-1-carboxylate. LC-MS Method 2 $t_R$=4.72 min, m/z=394.

Isomer 2: (R)-(trans-1-carbamoyl-4-adamantyl) 3-(isopropoxycarbonylamino)pyrrolidine-1-carboxylate. LC-MS Method 2 $t_R$=5.31 min, m/z=394; $^1$H NMR (CDCl$_3$) 1.22 (d, 6H), 1.53 (d, 2H), 1.90-2.25 (13H), 2.66 (2H), 3.28 (dd, 1H), 3.49 (1H), 3.70 (m, 1H), 4.27 (1H), 4.82 (s, 1H), 4.93 (m, 1H), 5.74 (1H), 5.83 (1H).

Example 25

(R)-(1-carbamoyl-4-adamantyl) 3-(benzyloxycarbonylamino)pyrrolidine-1-carboxylate

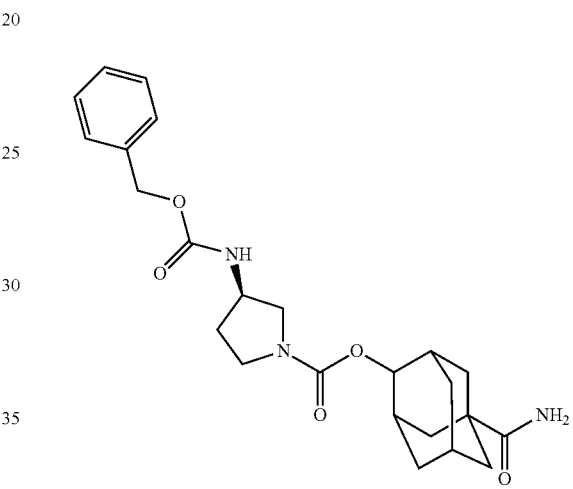

The title compound was prepared following procedures analogous to those described in Example 18 using Cbz-OSu in Step 2. Two isomers were separated by preparative HPLC.

Isomer 1: (R)-(cis-1-carbamoyl-4-adamantyl) 3-(benzyloxycarbonylamino)pyrrolidine-1-carboxylate. LC-MS Method 2 $t_R$=5.87 min, m/z=442.

Isomer 2: (R)-(trans-1-carbamoyl-4-adamantyl) 3-(benzyloxycarbonylamino)pyrrolidine-1-carboxylate. LC-MS Method 2 $t_R$=6.37 min, m/z=442; $^1$H NMR (CDCl$_3$) 1.53 (d, 2H), 1.80-0.25 (13H), 3.29 (dd, 1H), 3.48 (m, 2H), 3.67 (m, 1H), 4.29 (1H), 4.83 (s, 1H), 5.02 (s, 1H), 5.12 (s, 2H), 5.75 (1H), 5.87 (1H), 7.37 (5H).

Example 26

(R)-(1-carbamoyl-4-adamantyl) 3-(allyl(tert-butoxycarbonyl)amino)pyrrolidine-1-carboxylate

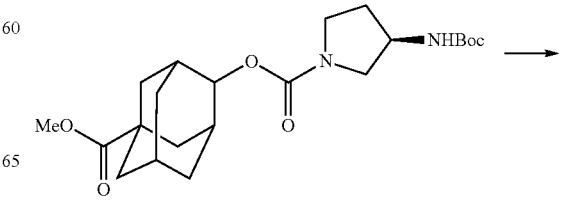

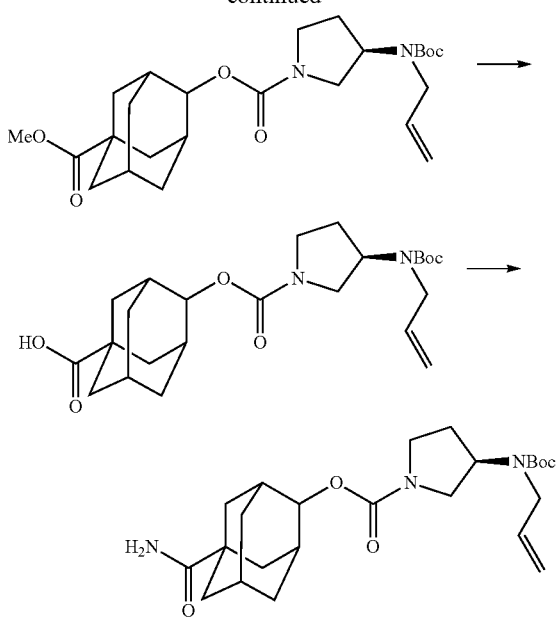

The title compound was prepared using a procedure analogous to that described in Example 9 Method 2 replacing methyl iodide with allyl bromide, followed by procedures analogous to those described in Example 16 Steps 1 and 2. Preparative HPLC afforded two isomers.

Isomer 1: (R)-(cis-1-carbamoyl-4-adamantyl) 3-(allyl (tert-butoxycarbonyl)amino)pyrrolidine-1-carboxylate. LC-MS Method 1 $t_R$=1.62 min, m/z=470, 348.

Isomer 2: (R)-(trans-1-carbamoyl-4-adamantyl) 3-(allyl (tert-butoxycarbonyl)amino)pyrrolidine-1-carboxylate. LC-MS Method 1 $t_R$=1.72 min, m/z=470, 448, 348; $^1$H NMR (CDCl$_3$) 1.44 (s, 9H), 1.52 (d, 2H), 1.80-2.30 (13H), 3.30 (3H), 3.59 (m, 2H), 3.78 (2H), 4.83 (s, 1H), 5.12 (d, 2H), 5.63 (2H), 5.79 (m, 1H).

Example 27

(R)-(1-(2-hydroxy-2-propyl)-4-adamantyl) 3-(tert-butoxycarbonylamino)pyrrolidine-1-carboxylate

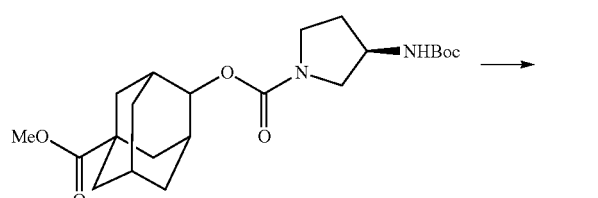

A stirred solution of (3R)-(1-(methoxycarbonyl)-4-adamantyl) 3-(tert-butoxycarbonylamino)pyrrolidine-1-carboxylate (76 mg, 0.18 mmol) in dry THF (3 mL) was cooled to −70° C. and 3 M MeMgBr in Et$_2$O (0.5 mL<1.5 mmol) was added. The mixture was allowed to warm to rt over 2 h. LC-MS showed unconsumed starting material. The mixture was recooled to −70° C. and a second aliquot of 3 M MeMgBr in Et$_2$O (0.5 mL, 1.5 mmol). The mixture was allowed to warm to rt over 2 h, quenched with satd aq NH$_4$Cl (30 mL) and extracted with ether (80 mL). The ether layer was washed with brine (30 mL), dried over MgSO$_4$ and concentrated to leave an oil (54 mg) which was purified by preparative HPLC to afford two isomers.

Isomer 1: (R)-(cis-1-(2-hydroxy-2-propyl)-4-adamantyl) 3-(tert-butoxycarbonylamino)pyrrolidine-1-carboxylate (16 mg). LC-MS Method 1 $t_R$=1.68 min, m/z=445, 349.

Isomer 2: (R)-(trans-1-(2-hydroxy-2-propyl)-4-adamantyl) 3-(tert-butoxycarbonylamino)pyrrolidine-1-carboxylate (13 mg). LC-MS Method 1 $t_R$=1.76 min, m/z=445, 423, 349; $^1$H NMR (CDCl$_3$) 1.16 (s, 6H), 1.43 (s, 9H), 1.65-2.15 (15H), 3.26 (dd, 1H), 3.50 (2H), 3.68 (1H), 4.21 (1H), 4.70 (1H), 4.79 (1H).

Example 28

(R)-(1-carbamoyl-4-adamantyl) 3-(tert-butoxycarbonyl(2-hydroxyethyl)amino)pyrrolidine-1-carboxylate

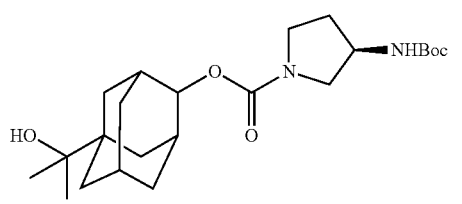

To a stirred solution of (R)-(trans 1-carbamoyl-4-adamantyl) 3-(allyl(tert-butoxycarbonyl)amino)pyrrolidine-1-carboxylate (isomer 2) (5 mg, 0.011 mmol) in 1:1 THF/water (1 mL) were added NaIO$_4$ (12 mg, 0.056 mmol) and 2.5% OsO$_4$ in t-BuOH (0.003 mL, 0.00011 mmol). The mixture was stirred at rt for 4 h, diluted with EtOAc (90 mL), washed with brine (20 mL) and dried over Na$_2$SO$_4$. The solvent was removed and the residue (5.6 mg) was dissolved in MeOH (3 mL) and treated with NaBH$_4$ (50 mg). The mixture was stirred at rt for 5 h and quenched with brine (20 mL). The mixture was extracted with EtOAc (2×75 mL). The combined EtOAc extracts were dried over Na$_2$SO$_4$ and concentrated to leave a yellow oil (9.5 mg) which was purified by preparative HPLC to afford (R)-(trans-1-carbamoyl-4-adamantyl 3-(tert-butoxycarbonyl(2-hydroxyethyl)amino)pyrrolidine-1-carboxylate (3 mg, 59%). LC-MS Method 1 $t_R$=1.35 min, m/z=452, 396, 352.

Example 29

(1-carbamoyl-4-adamantyl) 3-benzyl-3-(tert-butoxy-carbonylamino)pyrrolidine-1-carboxylate

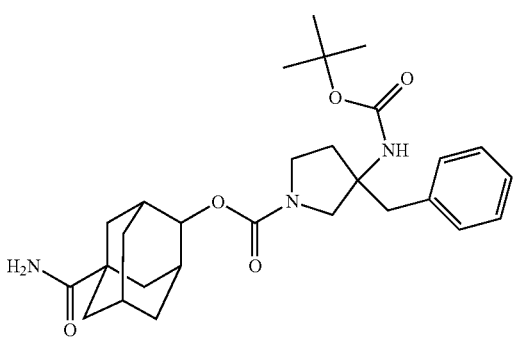 [SMILES: CC(C)(C)OC(=O)NC1(Cc2ccccc2)CCN(C(=O)OC2C3CC4CC2CC(C(N)=O)(C4)C3)C1]

The title compound was prepared by a procedure analogous to that described in Example 14 using tert-butyl 3-benzylpyrrolidin-3-ylcarbamate, followed by procedures analogous to those described in Example 16. Two isomers were separated by preparative HPLC.

Isomer 1: (cis-1-carbamoyl-4-adamantyl) 3-benzyl-3-(tert-butoxycarbonylamino)pyrrolidine-1-carboxylate. LC-MS Method 1 $t_R$=1.70 min, m/z=520, 398.

Isomer 2: (trans-1-carbamoyl-4-adamantyl) 3-benzyl-3-(tert-butoxycarbonylamino)pyrrolidine-1-carboxylate. LC-MS Method 1 $t_R$=1.8 min, m/z=520, 398; $^1$H NMR (CDCl$_3$) 1.45 (s, 9H), 1.52 (2H), 1.85-2.10 (11H), 2.17 (2H), 2.85-3.95 (6H), 4.84 (1H), 5.15 (1H), 5.88 (1H), 6.32 (1H), 7.15 (2H), 7.29 (3H).

Isomer 2 (13.8 mg) was further fractionated by chromatography on a Chiralpak IA column eluted with 78:22 hexanes/EtOH to afford two enantiomers.

Isomer 2.1 (5.4 mg): $^1$H NMR (CDCl$_3$) 1.45 (s, 9H), 1.52 (2H), 1.85-2.10 (11H), 2.17 (2H), 2.85-3.95 (6H), 4.30 (1H), 4.85 (1H), 5.22 (1H), 5.57 (1H), 7.15 (2H), 7.29 (3H).

Isomer 2.2 (5.7 mg): $^1$H NMR (CDCl$_3$) 1.45 (s, 9H), 1.52 (2H), 1.85-2.10 (11H), 2.17 (2H), 2.85-3.95 (6H), 4.30 (1H), 4.85 (1H), 5.22 (1H), 5.57 (1H), 7.15 (2H), 7.29 (3H).

Example 30

1-tert-butyl 7-(1-carbamoyl-4-adamantyl) 1,7-diazaspiro[4.4]nonane-1,7-dicarboxylate

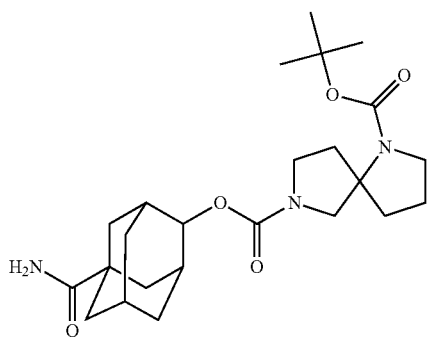 [SMILES: CC(C)(C)OC(=O)N1CCCC12CCN(C(=O)OC1C3CC4CC1CC(C(N)=O)(C4)C3)C2]

The title compound was prepared by a procedure analogous to that described in Example 14 using tert-butyl 1,7-diazaspiro[4.4]nonane-1-carboxylate, followed by procedures analogous to those described in Example 16. Two isomers were separated by preparative HPLC.

Isomer 1: 1-tert-butyl 7-(cis-1-carbamoyl-4-adamantyl) 1,7-diazaspiro[4.4]nonane-1,7-dicarboxylate. LC-MS Method 1 $t_R$=1.47 min, m/z=470, 348.

Isomer 2: 1-tert-butyl 7-(trans-1-carbamoyl-4-adamantyl) 1,7-diazaspiro[4.4]nonane-1,7-dicarboxylate. LC-MS Method 1 $t_R$=1.67 min, m/z=470, 348.

Example 31

(R)-(1-carbamoyl-4-adamantyl) 3-(4-(trifluoromethyl)pyrimidin-2-ylamino)pyrrolidine-1-carboxylate

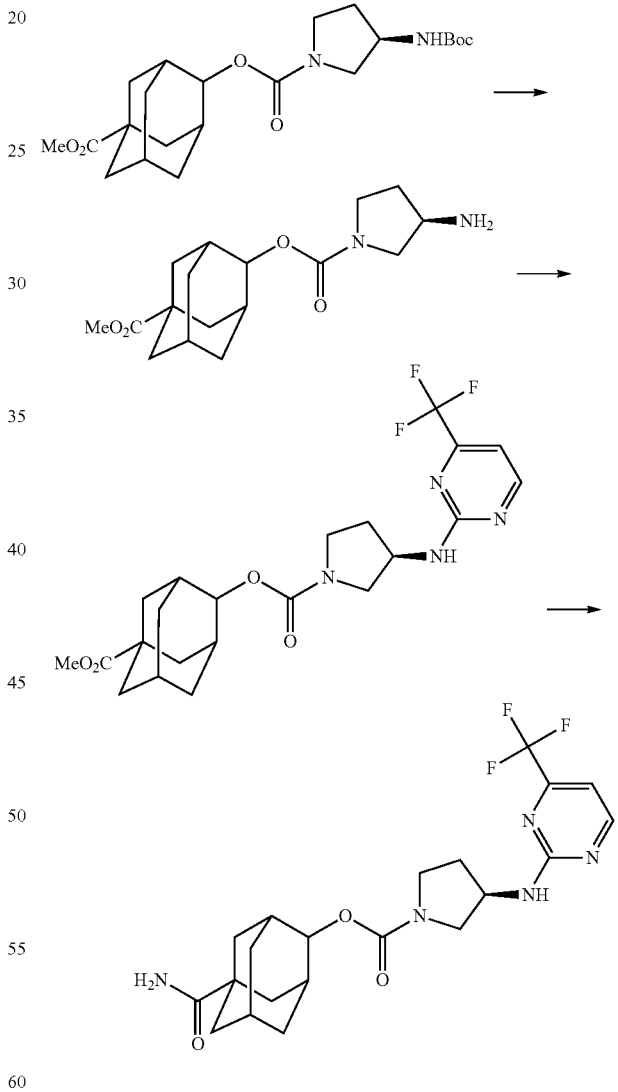

The title compound was prepared following procedures analogous to those described in Example 32 using 2-chloro-4-(trifluoromethyl)pyrimidine in Step 2. Two isomers were isolated.

Isomer 1: (R)-(cis-1-carbamoyl-4-adamantyl) 3-(4-(trifluoromethyl)pyrimidin-2-ylamino)pyrrolidine-1-carboxylate. LC-MS Method 2, $t_R$=6.30 min, m/z=454; $^1$H NMR (CDCl₃) 1.65-2.20 (14H), 2.29 (m, 1H), 3.39 (m, 1H), 3.56 (m, 2H), 3.80 (m, 1H), 4.58 (m, 1H), 4.83 (s, 1H), 5.66 (3H), 6.91 (d, 1H), 8.50 (1H)

Isomer 2: (R)-(trans-1-carbamoyl-4-adamantyl) 3-(4-(trifluoromethyl)pyrimidin-2-ylamino)pyrrolidine-1-carboxylate. LC-MS Method 2, $t_R$=6.89 min, m/z=454.

Example 32

(R)-(trans-1-carbamoyl-4-adamantyl) 3-(5-(trifluoromethyl)pyridin-2-ylamino)pyrrolidine-1-carboxylate

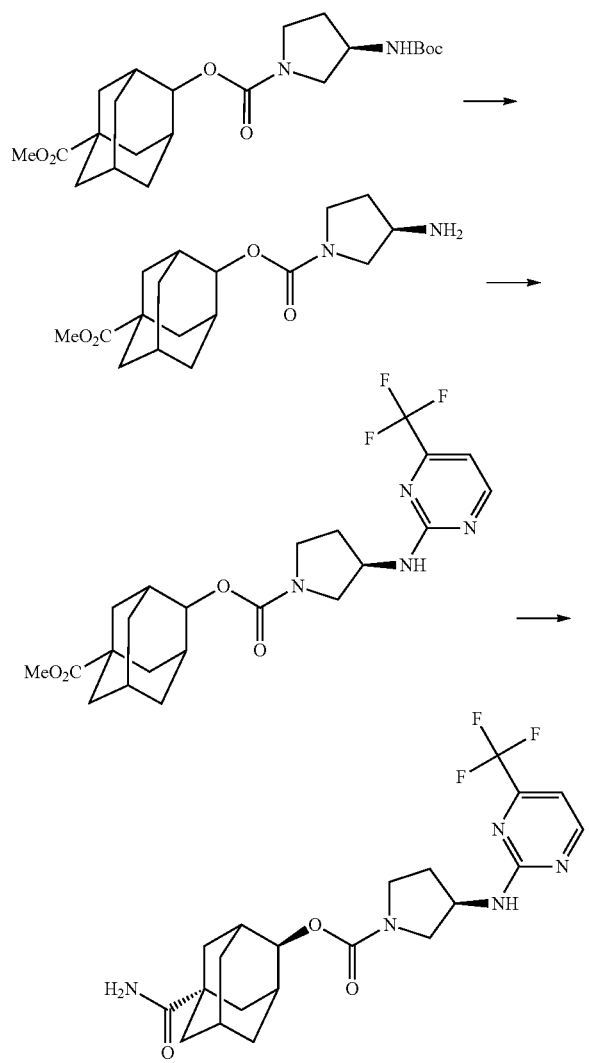

Step 1

(R)-(1-(methoxycarbonyl)-4-adamantyl) 3-(tert-butoxycarbonylamino)pyrrolidine-1-carboxylate (3.32 g, 7.86 mmol) was dissolved in MeOH (30 mL) and 4 M HCl in dioxane (10 mL) was added. The mixture was stirred at rt overnight and concentrated to afford (R)-(1-(methoxycarbonyl)-4-adamantyl) 3-aminopyrrolidine-1-carboxylate as its HCl salt (2.85 g, quant). LC-MS Method 1 $t_R$=1.03 min, m/z=323.

Step 2

A mixture of (R)-(1-(methoxycarbonyl)-4-adamantyl) 3-aminopyrrolidine-1-carboxylate HCl salt (252 mg, 0.78 mmol), 2-chloro-5-(trifluoromethyl)pyridine (156 mg, 0.86 mmol), i-Pr₂NEt (0.17 mL, 0.94 mmol) and i-PrOH (3 mL) was heated in a microwave at 150° C. for 1 h and at 160° C. for 2 h. The mixture was diluted with EtOAc (100 mL) and washed with 5% aq HCl (15 mL) and brine (15 mL). The combined aqueous washes were back extracted with EtOAc (20 mL). The combined organic layers were dried over Na₂SO₄ and concentrated to give crude (R)-(1-(methoxycarbonyl)-4-adamantyl) 3-(4-(trifluoromethyl)pyrimidin-2-ylamino)pyrrolidine-1-carboxylate (181 mg, 49%) which was used without purification. LC-MS Method 1 $t_R$=1.86 min, m/z=468 and $t_R$=1.93 min, m/z=468.

Step 3

Crude (R)-(1-(methoxycarbonyl)-4-adamantyl) 3-(4-(trifluoromethyl)pyrimidin-2-ylamino)pyrrolidine-1-carboxylate (204 mg, 0.44 mmol) was dissolved in MeOH (4 mL) and THF (2 mL). A solution of LiOH.H₂O (40 mg, 1 mmol) in water (2 mL) was added. The mixture was stirred overnight at rt. Additional LiOH.H₂O (40 mg, 1 mmol) in water (2 mL) was added and stirring was continued for 2 d. The mixture was concentrated and the residue was purified by preparative HPLC to afford (R)-4-(3-(4-(trifluoromethyl)pyrimidin-2-ylamino)pyrrolidine-1-carbonyloxy)adamantane-1-carboxylic acid (39.7 mg). LC-MS Method 1 $t_R$=1.62 min, m/z=454 and $t_R$=1.72 min, m/z=454.

Step 4

A stirred solution of (R)-4-(3-(4-(trifluoromethyl)pyrimidin-2-ylamino)pyrrolidine-1-carbonyloxy)adamantane-1-carboxylic acid (39.7 mg, 0.09 mmol), HOBt (67 mg, 0.44 mmol) and i-Pr₂NEt (0.16 mL, 0.88 mmol) in CH₂Cl₂ (9 mL) was cooled in an ice bath and 0.5 M NH₃ in dioxane (1 mL, 0.5 mmol) was added, followed by solid EDC.HCl (85 mg, 0.44 mmol). The ice bath was allowed to melt and the mixture was stirred overnight at rt. The mixture was diluted with EtOAc (90 mL), washed with 10% aq Na₂CO₃ (15 mL) and brine (15 mL), and dried over Na₂SO₄. Removal of the solvent left an oil (47 mg) which was purified by preparative HPLC. The longer $t_R$ isomer was isolated as its TFA salt. LC-MS Method 2, $t_R$=6.89 min, m/z=454; ¹H NMR (CD₃OD) 1.58 (m, 2H), 1.85-2.10 (12H), 2.33 (m, 1H), 3.44 (m, 0.5H), 3.52 (m, 1.5H), 3.64 (m, 1H), 3.76 (m, 0.5H), 3.83 (m, 0.5H), 4.46 (m, 1H), 4.90 (s, 1H), 6.99 (t, 1H), 7.92 (m, 1H), 8.28 (s, 1H).

Example 33

(R)-(trans-1-carbamoyl-4-adamantyl) 3-(2,6-dimethylpyrimidin-4-ylamino)pyrrolidine-1-carboxylate

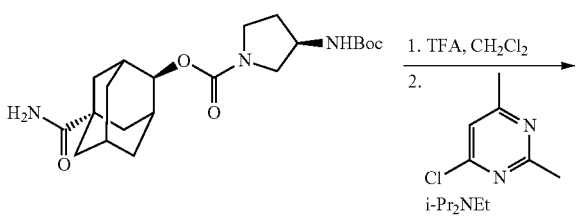

67

-continued

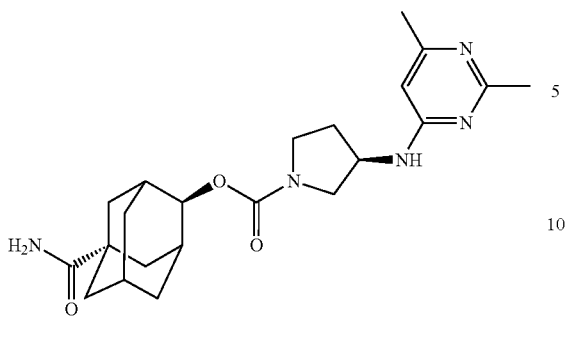

Step 1

To a stirred solution of (3R) (1-carbamoyl-4-adamantyl) 3-(tert-butoxycarbonylamino)pyrrolidine-1-carboxylate isomer 2 (81 mg) in $CH_2Cl_2$ (8 mL) was added TFA (2 mL). The mixture was stirred at rt for 1 h and concentrated. The residue was diluted with $CH_2Cl_2$ (80 mL), washed with satd aq $NaHCO_3$ (20 mL) and brine (20 mL), and dried over $Na_2SO_4$. Removal of the solvent left (3R)-(1-carbamoyl-4-adamantyl) 3-aminopyrrolidine-1-carboxylate (72 mg) as an oil. LC-MS Method 1 $t_R$=0.60 min, m/z=308.

Step 2

A solution of (3R)-(1-carbamoyl-4-adamantyl) 3-aminopyrrolidine-1-carboxylate (7 mg, 0.023 mmol), i-$Pr_2$NEt (0.016 mL, 0.091 mmol) and 4-chloro-2,6-dimethylpyrimidine (6.5 mg, 0.046 mmol) in i-PrOH (1 mL) was heated at 160° C. for 4 h in a microwave. The reaction solution was purified by preparative HPLC to afford (R)-(trans-1-carbamoyl-4-adamantyl) 3-(2,6-dimethylpyrimidin-4-ylamino)pyrrolidine-1-carboxylate (4.2 mg, 44%). LC-MS Method 1, $t_R$=0.98 min, m/z=414; $^1$H NMR ($CD_3OD$) 1.59 (m, 2H), 1.85-2.15 (12H), 2.30 (m, 1H), 2.40 (s, 3H), 3.58 (s, 3H), 3.30-3.90 (4H), 4.80 (2H), 6.43 (s, 1H)

Example 34

(R)-(trans-1-carbamoyl-4-adamantyl) 3-(3-cyanopyridin-2-ylamino)pyrrolidine-1-carboxylate

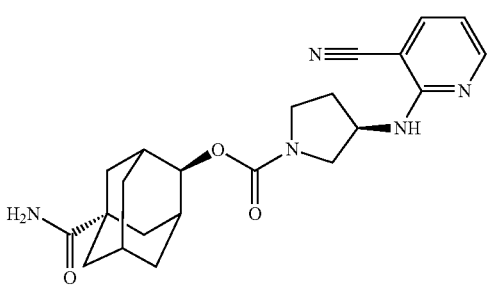 [SMILES: N#Cc1cccnc1N[C@@H]1CCN(C(=O)O[C@H]2C3CC4CC2C[C@](C(N)=O)(C4)C3)C1]

The title compound was prepared following a procedure analogous to that described in Example 33 Step 2 using 2-fluoro-3-cyanopyridine. LC-MS Method 1, $t_R$=5.83 min, m/z=410; $^1$H NMR ($CD_3OD$) 1.59 (m, 2H), 1.85-2.15 (12H), 2.32 (m, 1H), 3.35-3.90 (4H), 4.63 (m, 1H), 4.78 (s, 1H), 6.76 (m, 1H), 7.88 (d, 1H), 8.27 (s, 1H).

68

Example 35

(R)-(trans-1-carbamoyl-4-adamantyl) 3-(5-cyanopyridin-2-ylamino)pyrrolidine-1-carboxylate

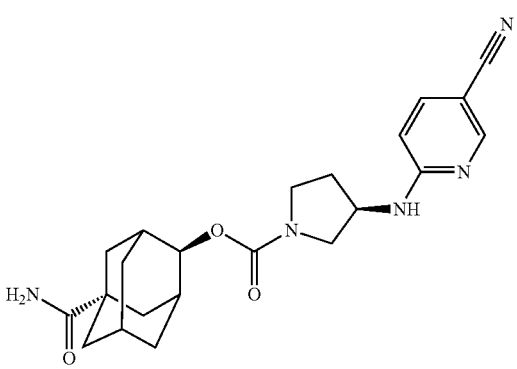 [SMILES: N#Cc1ccc(N[C@@H]2CCN(C(=O)O[C@H]3C4CC5CC3C[C@](C(N)=O)(C5)C4)C2)nc1]

The title compound was prepared following a procedure analogous to that described in Example 33 Step 2 using 2-fluoro-5-cyanopyridine. LC-MS Method 1, $t_R$=1.33 min, m/z=410; $^1$H NMR ($CD_3OD$) 1.58 (m, 2H), 1.85-2.15 (12H), 2.27 (m, 1H), 3.35-3.90 (4H), 4.51 (m, 1H), 4.77 (s, 1H), 6.66 (d, 1H), 7.66 (d, 1H), 8.37 (s, 1H).

Example 36

(S)-(trans-1-carbamoyl-4-adamantyl) 3-(5-(trifluoromethyl)pyridin-2-ylamino)pyrrolidine-1-carboxylate

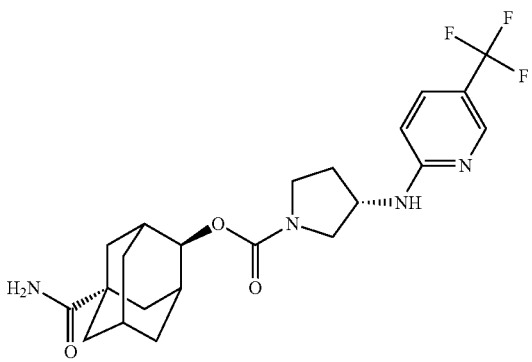 [SMILES: NC(=O)[C@]12CC3CC(C1)[C@@H](OC(=O)N1CC[C@H](Nc4ccc(C(F)(F)F)cn4)C1)C(C3)C2]

The title compound was prepared following procedures analogous to those described in Example 31 using (S)-(1-(methoxycarbonyl)-4-adamantyl) 3-(tert-butoxycarbonylamino)pyrrolidine-1-carboxylate in Step 1. The longer $t_R$ isomer was isolated. LC-MS Method 1, $t_R$=1.53 min, m/z=453; $^1$H NMR ($CD_3OD$) 1.58 (m, 2H), 1.85-2.15 (12H), 2.33 (m, 1H), 3.46 (m, 0.5H), 3.54 (m, 1.5H), 3.64 (m, 1H), 3.77 (m, 0.5H), 3.83 (m, 0.5H), 4.47 (m, 1H), 4.79 (s, 1H), 7.00 (m, 1H), 7.90 (m, 1H), 8.28 (s, 1H).

Example 37

(R)-(trans-1-carbamoyl-4-adamantyl) 3-(3-(trifluoromethyl)pyridin-2-ylamino)pyrrolidine-1-carboxylate

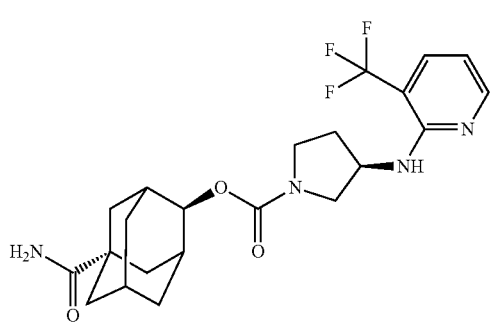 [SMILES: NC(=O)[C@]12CC3CC(C1)[C@@H](OC(=O)N1CC[C@@H](Nc4ncccc4C(F)(F)F)C1)C(C3)C2]

The title compound was prepared following procedures analogous to those described in Example 31 using 2-chloro-3-(trifluoromethyl)pyridine in Step 2. The longer $t_R$ isomer was isolated. LC-MS Method 1, $t_R$=1.62 min, m/z=453; $^1$H NMR (CD$_3$OD) 1.58 (m, 2H), 1.85-2.15 (12H), 2.33 (m, 1H), 3.35-3.90 (4H), 4.70 (m, 1H), 4.79 (s, 1H), 6.78 (m, 1H), 7.84 (d, 1H), 8.28 (m, 1H).

Example 38

(R)-(trans-1-carbamoyl-4-adamantyl) 3-(6-(trifluoromethyl)pyridin-2-ylamino)pyrrolidine-1-carboxylate

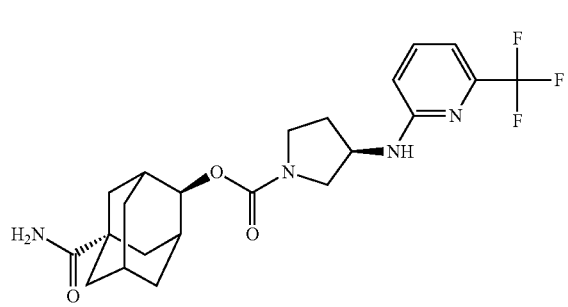 [SMILES: NC(=O)[C@]12CC3CC(C1)[C@@H](OC(=O)N1CC[C@@H](Nc4cccc(C(F)(F)F)n4)C1)C(C3)C2]

The title compound was prepared following procedures analogous to those described in Example 31 using 2-bromo-6-(trifluoromethyl)pyridine in Step 2. The longer $t_R$ isomer was isolated. LC-MS Method 1, $t_R$=1.7 min, m/z=453; $^1$H NMR (CD$_3$OD) 1.58 (m, 2H), 1.85-2.15 (12H), 2.35 (m, 1H), 3.40-3.90 (4H), 4.46 (m, 1H), 4.78 (m, 1H), 6.71 (d, 1H), 6.90 (d, 1H), 7.53 (t, 1H).

Example 39

(R)-(trans-1-carbamoyl-4-adamantyl) 3-(4-(trifluoromethyl)pyridin-2-ylamino)pyrrolidine-1-carboxylate

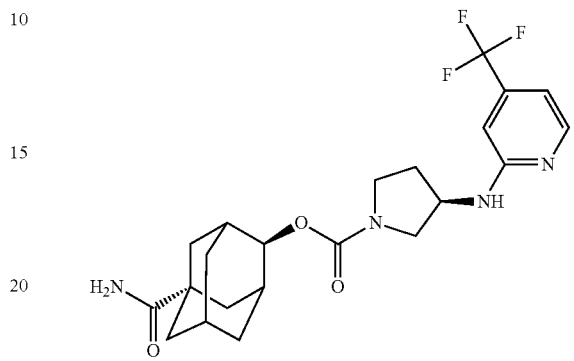

The title compound was prepared following procedures analogous to those described in Example 31 using 2-bromo-4-(trifluoromethyl)pyridine in Step 2. The longer $t_R$ isomer was isolated. LC-MS Method 1, $t_R$=1.47 min, m/z=453; $^1$H NMR (CD$_3$OD) 1.58 (m, 2H), 1.85-2.15 (12H), 2.35 (m, 1H), 3.40-3.90 (4H), 4.43 (m, 1H), 4.80 (s, 1H), 6.98 (t, 1H), 7.15 (d, 1H), 8.13 (m, 1H).

Example 40

(S)-(trans-1-carbamoyl-4-adamantyl) 3-(3-(trifluoromethyl)pyridin-2-ylamino)pyrrolidine-1-carboxylate

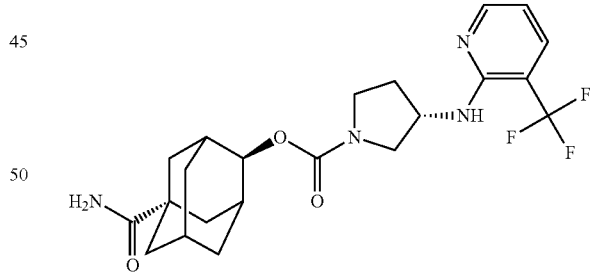

The title compound was prepared following procedures analogous to those described in Example 31 using (S)-(1-(methoxycarbonyl)-4-adamantyl) 3-(tert-butoxycarbonylamino)pyrrolidine-1-carboxylate in Step 1 and 2-chloro-3-(trifluoromethyl)pyridine in Step 2. The longer $t_R$ isomer was isolated. LC-MS Method 1, $t_R$=1.63 min, m/z=453; $^1$H NMR (CD$_3$OD) 1.58 (m, 2H), 1.85-2.15 (12H), 2.33 (m, 1H), 3.35-3.90 (4H), 4.70 (m, 1H), 4.79 (s, 1H), 6.78 (m, 1H), 7.84 (d, 1H), 8.28 (m, 1H).

Example 41

(R)-(trans-1-carbamoyl-4-adamantyl) 3-(2-(trifluoromethyl)pyrimidin-4-ylamino)pyrrolidine-1-carboxylate

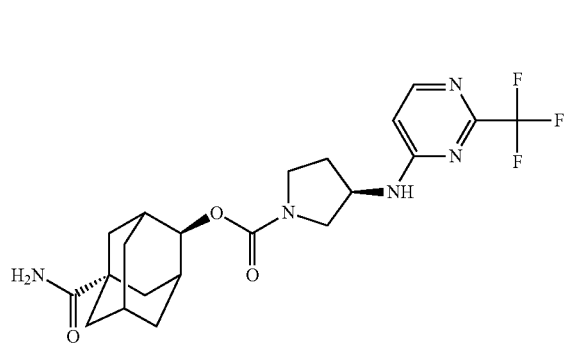 [SMILES: NC(=O)[C@]12CC3CC(C1)[C@@H](OC(=O)N1CC[C@@H](Nc4ccnc(C(F)(F)F)n4)C1)C(C3)C2]

The title compound was prepared following procedures analogous to those described in Example 31 using 4-chloro-2-(trifluoromethyl)pyrimidine in Step 2. The longer $t_R$ isomer was isolated. LC-MS Method 1, $t_R$=1.45 min, m/z=454; $^1$H NMR (CD$_3$OD) 1.58 (m, 2H), 1.85-2.15 (12H), 2.29 (m, 1H), 3.30-3.90 (4H), 4.60 (m, 1H), 4.78 (m, 1H), 6.64 (m, 1H), 8.13 (m, 1H)

Example 42

(R)-(trans-1-carbamoyl-4-adamantyl) 3-(5-(trifluoromethyl)-1,3,4-thiadiazol-2-ylamino)pyrrolidine-1-carboxylate

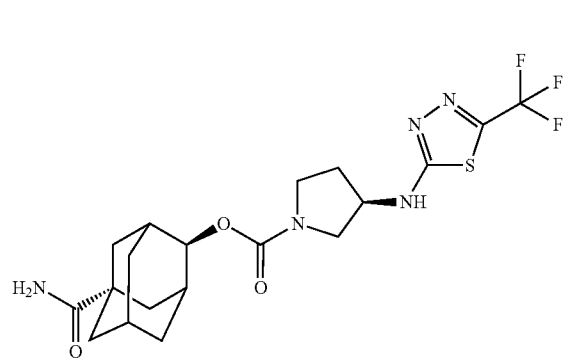 [SMILES: NC(=O)[C@]12CC3CC(C1)[C@@H](OC(=O)N1CC[C@@H](Nc4nnc(C(F)(F)F)s4)C1)C(C3)C2]

The title compound was prepared following a procedure analogous to that described in Example 33 Step 2 using 2-chloro-5-(trifluoromethyl)-1,3,4-thiadiazole. LC-MS Method 1 $t_R$=1.45 min, m/z=460; $^1$H NMR (CD$_3$OD) 1.58 (m, 2H), 1.90-2.20 (12H), 2.29 (m, 1H), 3.50-3.80 (4H), 4.44 (m, 1H), 4.78 (s, 1H).

Example 43

(trans-1-carbamoyl-4-adamantyl) 3-(methyl(5-(trifluoromethyl)pyridin-2-yl)amino)pyrrolidine-1-carboxylate

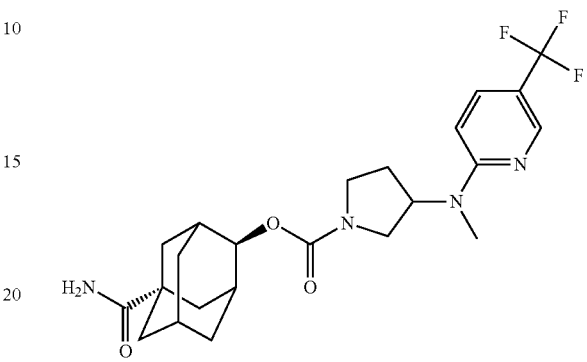

The title compound was prepared following procedures analogous to those described in Example 31 using (1-(methoxycarbonyl)-4-adamantyl) 3-(tert-butoxycarbonyl(methyl)amino)pyrrolidine-1-carboxylate in Step 1 and 2-chloro-5-(trifluoromethyl)pyridine in Step 2. The longer $t_R$ isomer was isolated. LC-MS Method 1 $t_R$=1.72 min, m/z=467; $^1$H NMR (CD$_3$OD) 1.58 (m, 2H), 1.85-2.25 (13H), 3.04 (s, 3H), 3.35-3.80 (4H), 4.81 (s, 1H), 5.35 (m, 1H), 6.92 (d, 1H), 7.82 (d, 1H), 8.38 (s, 1H).

Example 44

(trans-1-carbamoyl-4-adamantyl) 3-(methyl(3-(trifluoromethyl)pyridin-2-yl)amino)pyrrolidine-1-carboxylate

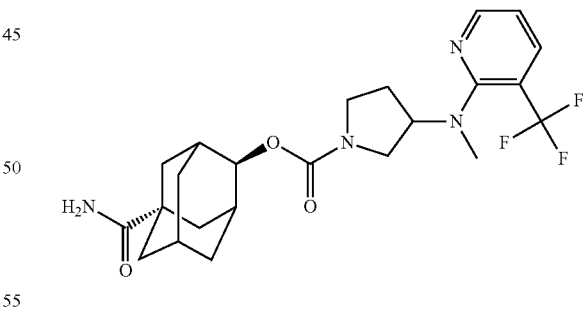

The title compound was prepared following procedures analogous to those described in Example 31 using (1-(methoxycarbonyl)-4-adamantyl) 3-(tert-butoxycarbonyl(methyl)amino)pyrrolidine-1-carboxylate in Step 1 and 2-chloro-3-(trifluoromethyl)pyridine in Step 2. The longer $t_R$ isomer was isolated. LC-MS Method 1, $t_R$=1.7 min, m/z=467; $^1$H NMR (CD$_3$OD) 1.58 (m, 2H), 1.85-2.15 (13H), 2.75 (s, 1.5H), 2.78 (s, 1.5H), 3.10-3.70 (4H), 4.20 (m, 1H), 4.74 (s, 1H), 7.25 (m, 1H), 8.08 (d, 1H), 8.56 (m, 1H).

Example 45

(trans-1-carbamoyl-4-adamantyl) 3-(methyl(6-(trifluoromethyl)pyridin-2-yl)amino)pyrrolidine-1-carboxylate

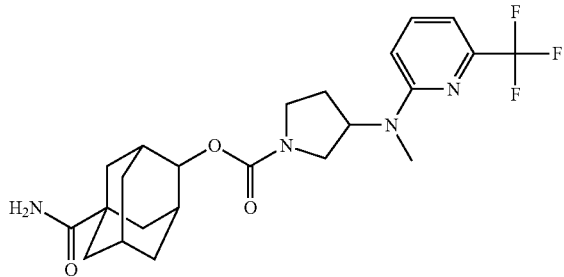 [SMILES: CN(c1cccc(C(F)(F)F)n1)C1CCN(C(=O)OC2C3CC4CC2CC(C(N)=O)(C4)C3)C1]

The title compound was prepared following procedures analogous to those described in Example 31 using (1-(methoxycarbonyl)-4-adamantyl) 3-(tert-butoxycarbonyl(methyl) amino)pyrrolidine-1-carboxylate in Step 1 and 2-bromo-6-(trifluoromethyl)pyridine in Step 2. The longer $t_R$ isomer was isolated. LC-MS Method 2, $t_R$=8.52 min, m/z=467; $^1$H NMR (CD$_3$OD) 1.58 (m, 2H), 1.85-2.15 (13H), 2.90-3.05 (3H), 3.30-3.80 (4H), 4.80 (m, 1H), 5.30 (m, 1H), 6.60-7.80 (3H).

Example 46

(R)-tert-butyl 1-(2-adamantylcarbamoyl)pyrrolidin-3-ylcarbamate

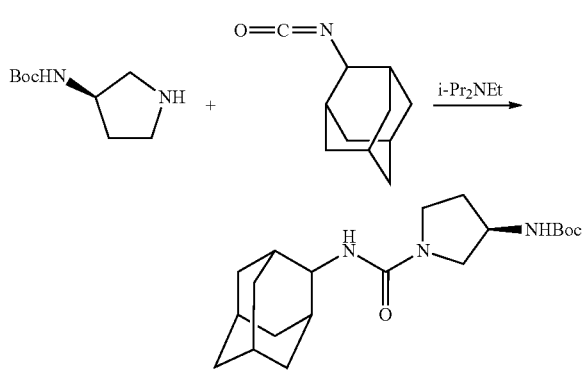

A vial was charged with (R)-tert-butyl pyrrolidin-3-ylcarbamate (21 mg, 0.11 mmol) and i-Pr$_2$NEt (0.025 mL, 0.14 mmol). A solution of 2-adamantyl isocyanate (25 mg, 0.14 mmol) in CH$_2$Cl$_2$ (2 mL) was added with stirring. After stirring overnight the mixture was applied to a 10-mL ChemElut cartridge that had been prewetted with 5% aq HCl (6 mL). The cartridge was eluted with ether (20 mL). The eluate was evaporated to dryness and the residue was applied to a 2-g silica SPE cartridge. The cartridge was eluted sequentially with 0, 10, 25, 50, 75 and 100% EtOAc in hexanes (15 mL of each) to afford six fractions. Fractions 4 and 5 were pooled and concentrated to afford (R)-tert-butyl 1-(2-adamantylcarbamoyl)pyrrolidin-3-ylcarbamate (7.9 mg, 15%). LC-MS Method 1, $t_R$=1.83 min, m/z=364; $^1$H NMR (CDCl$_3$) 1.42 (s, 9H), 1.60-1.95 (15H), 2.17 (m, 1H), 3.21 (m, 1H), 3.46 (m, 2H), 3.61 (m, 1H), 3.96 (m, 1H), 4.22 (1H), 4.53 (d, 1H), 4.72 (1H)

Example 47

(S)-tert-butyl 1-(2-adamantylcarbamoyl)pyrrolidin-3-ylcarbamate

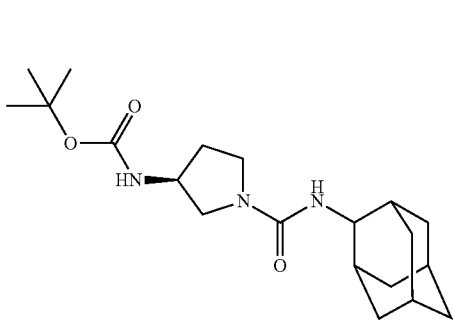 [SMILES: CC(C)(C)OC(=O)N[C@H]1CCN(C(=O)NC2C3CC4CC(C3)CC2C4)C1]

The title compound was prepared following a procedure analogous to that described in Example 46 using (S)-tert-butyl pyrrolidin-3-ylcarbamate. LC-MS Method 1, $t_R$=1.82 min, m/z=364, 308; $^1$H NMR (CDCl$_3$) 1.42 (s, 9H), 1.60-1.95 (15H), 2.17 (m, 1H), 3.21 (m, 1H), 3.46 (m, 2H), 3.61 (m, 1H), 3.96 (m, 1H), 4.22 (1H), 4.53 (d, 1H), 4.72 (1H).

Example 48

(R)-methyl 1-(2-adamantylcarbamoyl)pyrrolidin-3-ylcarbamate

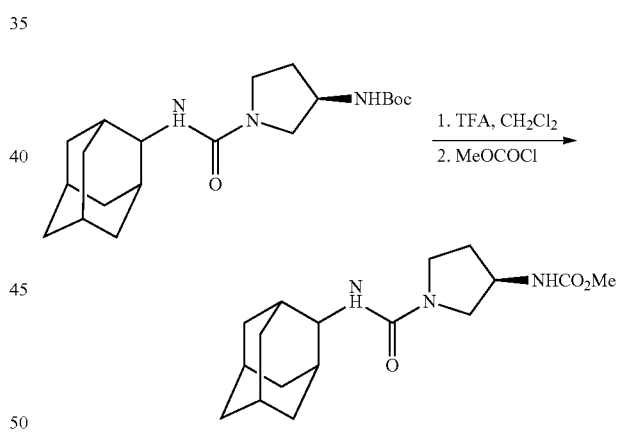

Step 1

(R)-tert-butyl 1-(2-adamantylcarbamoyl)pyrrolidin-3-ylcarbamate was reacted under conditions analogous to those described in Example 33 Step 1 to afford (R)-3-amino-N-(2-adamantyl)pyrrolidine-1-carboxamide.

Step 2

A vial equipped with a flea stir bar was charged with (R)-3-amino-N-(2-adamantyl)pyrrolidine-1-carboxamide (25 mg, 0.095 mmol), i-Pr$_2$NEt (0.07 mL, 0.38 mmol) and CH$_2$Cl$_2$. The solution was stirred and methyl chloroformate (0.009 mL, 0.11 mmol) was added. The mixture was stirred overnight at rt and applied to a 10-mL ChemElut cartridge prewetted with 5% aq HCl (6 mL). The cartridge was eluted with ether (20 mL). The eluate was evaporated to dryness and the residue was purified by preparative HPLC to afford (R)-methyl 1-(2-adamantylcarbamoyl)pyrrolidin-3-ylcarbamate (15 mg, 49%). LC-MS Method 1, $t_R$=1.5 min, m/z=322; $^1$H NMR (CDCl$_3$) 1.60-2.00 (15H), 2.20 (m, 1H), 3.26 (m, 1H), 3.46 (m, 2H), 3.63 (m, 1H), 3.69 (s, 3H), 3.96 (s, 1H), 4.30 (1H), 4.60 (1H), 4.89 (d, 1H).

Example 49

(R)-isopropyl 1-((2-adamantyl)carbamoyl)pyrrolidin-3-ylcarbamate

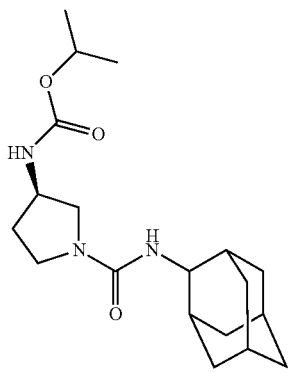 [SMILES: CC(C)OC(=O)N[C@@H]1CCN(C(=O)NC2C3CC4CC(C3)CC2C4)C1]

The title compound was prepared following a procedure analogous to that described in Example 48 Step 2 using isopropyl chloroformate. LC-MS Method 1, $t_R$=1.65 min.

Example 50

(R)-isobutyl 1-((2-adamantyl)carbamoyl)pyrrolidin-3-ylcarbamate

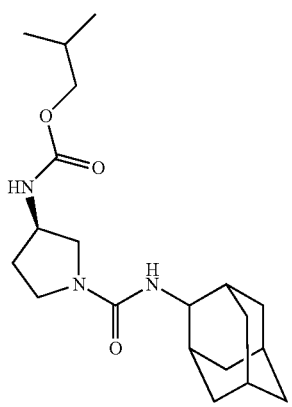 [SMILES: CC(C)COC(=O)N[C@@H]1CCN(C(=O)NC2C3CC4CC(C3)CC2C4)C1]

The title compound was prepared following a procedure analogous to that described in Example 48 Step 2 using isobutyl chloroformate. LC-MS Method 1, $t_R$=1.82 min, m/z=364.

Example 51 tert-butyl 1-(2-adamantylcarbamoyl)azetidin-3-ylcarbamate

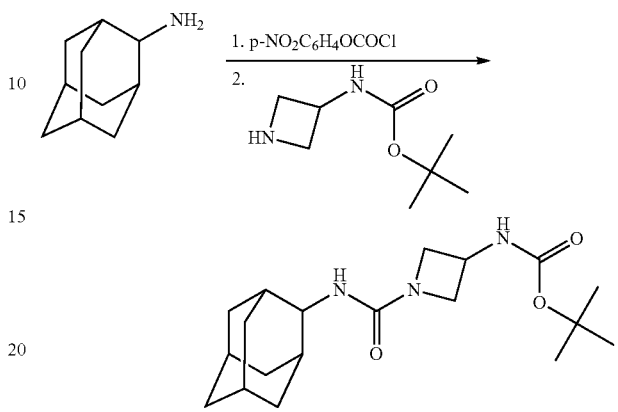

Step 1

To a stirred mixture of 2-aminoadamantane HCl salt (1.24 g, 6.61 mmol) and powdered NaHCO$_3$ (1.17 g, 13.9 mmol) in MeCN (40 mL) was added p-nitrophenyl chloroformate (1.40 g, 6.9 mmol). The mixture was stirred at rt for 1 d. The mixture was concentrated and the residue was taken up in ether (150 mL), washed with 5% aq HCl (50 mL) and brine (50 mL), and dried over MgSO$_4$. Removal of the solvent left a white solid (1.81 g). Chromatography on a 40-g silica cartridge eluted with a 30-100% EtOAc in hexanes gradient to afford 4-nitrophenyl (2-adamantyl)carbamate (1.33 g, 63%).

Step 2

To a stirred solution of 4-nitrophenyl (2-adamantyl)carbamate (40 mg, 0.12 mmol) in CH$_2$Cl$_2$ (2 mL) was added tert-butyl azetidin-3-ylcarbamate (40 mg, 0.23 mmol), followed by i-Pr$_2$NEt (0.05 mL, 0.28 mmol). The mixture was stirred over the weekend and applied to a 10-mL ChemElut cartridge prewetted with 5% aq HCl (6 mL). The cartridge was eluted with ether (20 mL). The eluate was evaporated to dryness and the residue was applied to 2-g silica SPE cartridge which was eluted sequentially with 0, 25, 50, 75, 100 and 100% EtOAc in hexanes (15 mL of each) to afford six fractions. Fraction 4 was concentrated to provide tert-butyl 1-(2-adamantylcarbamoyl)azetidin-3-ylcarbamate (19 mg, 43%). LC-MS Method 1, $t_R$=1.74 min, m/z=350, 294; $^1$H NMR (CDCl$_3$) 1.45 (s, 9H), 1.60-1.95 (14H), 3.75 (m, 2H), 3.89 (m, 1H), 4.22 (m, 2H), 4.39 (d, 1H), 4.46 (1H), 5.06 (1H).

Example 52 tert-butyl (1-(2-adamantylcarbamoyl)azetidin-3-yl)methylcarbamate

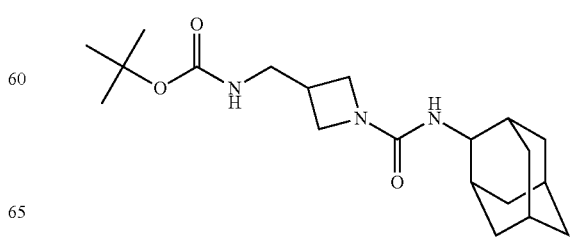

The title compound was prepared following a procedure analogous to that described in Example 51 Step 2 using tert-butyl azetidin-3-ylmethylcarbamate. LC-MS Method 1, $t_R$=1.75 min, m/z=364, 308; $^1$H NMR (CDCl$_3$) 1.44 (s, 9H), 1.60-1.95 (14H), 2.75 (m, 1H), 3.35 (m, 2H), 3.62 (m, 2H), 3.89 (m, 1H), 4.00 (t, 2H), 4.38 (d, 1H), 4.74 (1H).

Example 53 tert-butyl 1-(2-adamantylcarbamoyl)piperidin-4-ylcarbamate

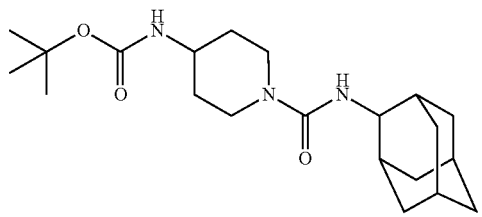 [SMILES: CC(C)(C)OC(=O)NC1CCN(C(=O)NC2C3CC4CC(C3)CC2C4)CC1]

The title compound was prepared following a procedure analogous to that described in Example 46 using tert-butyl piperidin-4-ylcarbamate. LC-MS Method 1, $t_R$=1.88 min, m/z=378, 322; $^1$H NMR (CDCl$_3$) 1.36 (m, 2H), 1.42 (s, 9H), 1.60-2.00 (16H), 2.95 (m, 2H), 3.61 (1H), 3.90 (m, 3H), 4.48 (1H), 4.83 (1H).

Example 54

(S)-tert-butyl (1-(2-adamantylcarbamoyl)pyrrolidin-3-yl)methylcarbamate

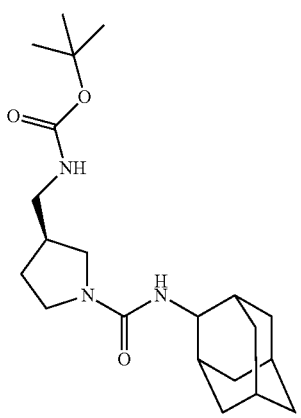 [SMILES: CC(C)(C)OC(=O)NC[C@@H]1CCN(C(=O)NC2C3CC4CC(C3)CC2C4)C1]

The title compound was prepared following a procedure analogous to that described in Example 46 using (R)-tert-butyl pyrrolidin-3-ylmethylcarbamate. LC-MS Method 1, $t_R$=1.85 min, m/z=378, 329; $^1$H NMR (CDCl$_3$) 1.43 (s, 9H), 1.60-1.95 (17H), 2.07 (m, 1H), 2.44 (m, 1H), 3.12 (m, 2H), 3.21 (m, 1H), 3.36 (m, 1H), 3.50 (2H), 3.96 (s, 1H).

Example 55 tert-butyl 1-(2-adamantylcarbamoyl)pyrrolidin-3-yl(methyl)carbamate

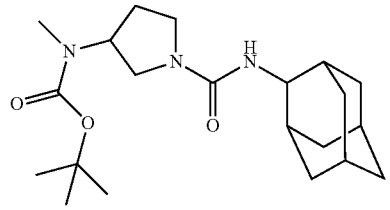 [SMILES: CN(C(=O)OC(C)(C)C)C1CCN(C(=O)NC2C3CC4CC(C3)CC2C4)C1]

The title compound was prepared following a procedure analogous to that described in Example 46 using tert-butyl methyl(pyrrolidin-3-yl)carbamate. LC-MS Method 1 $t_R$=1.97 min, m/z=378, 322; $^1$H NMR (CDCl$_3$) 1.46 (s, 9H), 1.60-1.95 (14H), 2.06 (m, 2H), 2.79 (s, 3H), 3.22 (m, 1H), 3.35 (m, 1H), 3.57 (m, 2H), 3.97 (1H), 4.60 (1H), 4.80 (1H).

Example 56

(R)-tert-butyl 1-(2-adamantylcarbamoyl)piperidin-3-ylcarbamate

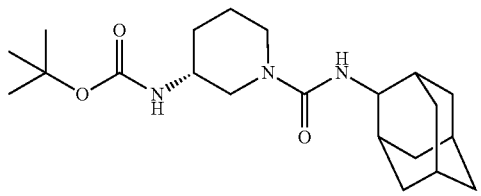 [SMILES: CC(C)(C)OC(=O)N[C@@H]1CCCN(C(=O)NC2C3CC4CC(C3)CC2C4)C1]

The title compound was prepared following a procedure analogous to that described in Example 46 using (R)-tert-butyl piperidin-3-ylcarbamate. $^1$H NMR (CDCl$_3$) 1.43 (s, 9H), 1.50-1.95 (18H), 3.26 (1H), 3.38 (m, 2H), 3.48 (d, 1H), 3.63 (1H), 3.94 (d, 1H), 4.73 (1H), 4.98 (1H).

Example 57

(S)-tert-butyl 1-(2-adamantylcarbamoyl)piperidin-3-ylcarbamate

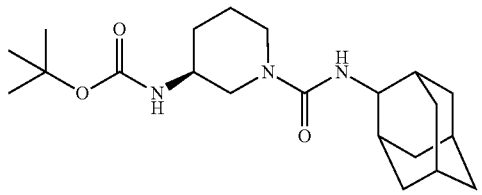 [SMILES: CC(C)(C)OC(=O)N[C@H]1CCCN(C(=O)NC2C3CC4CC(C3)CC2C4)C1]

The title compound was prepared following a procedure analogous to that described in Example 46 using (S)-tert-butyl piperidin-3-ylcarbamate. $^1$H NMR (CDCl$_3$) 1.43 (s, 9H), 1.50-1.95 (18H), 3.26 (1H), 3.38 (m, 2H), 3.48 (d, 1H), 3.63 (1H), 3.94 (d, 1H), 4.73 (1H), 4.98 (1H).

Example 58 tert-butyl 7-(2-adamantylcarbamoyl)-1,7-diazaspiro[4.4]nonane-1-carboxylate

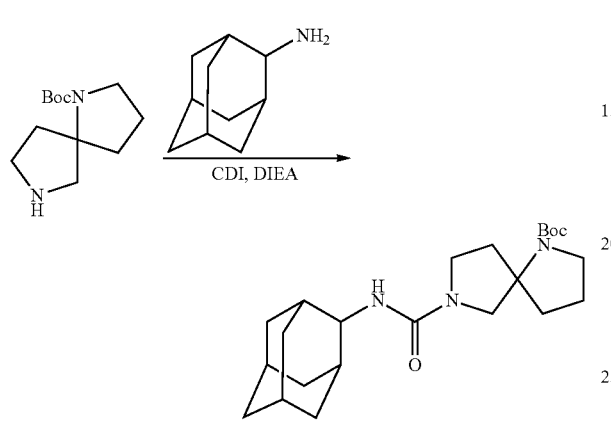

A solution of adamantan-2-ylamine (75 mg, 0.38 mmol), CDI (80 mg, 0.46 mmol), i-Pr$_2$NEt (150 mg, 1.14 mmol) in CH$_2$Cl$_2$ (5 mL) was stirred at 0° C. for 1 h, and tert-butyl 1,7-diazaspiro[4.4]nonane-1-carboxylate (100 mg, 0.38 mmol) was added. The reaction mixture stirred at room temperature overnight. The solvent was removed under reduced pressure to give crude product which was purified by preparative TLC to afford tert-butyl 7-(2-adamantylcarbamoyl)-1,7-diazaspiro[4.4]nonane-1-carboxylate (136 mg, 89%). LC-MS Method 3, $t_R$=4.24 min, m/z=404.1; $^1$H NMR (CDCl$_3$) 1.39 (s, 9H), 1.48-1.52 (m, 4H), 1.62-1.71 (m, 5H), 1.71-1.81 (m, 10H), 1.81-1.88 (m, 3H), 1.89-2.01 (m, 1H), 2.93-3.12 (m, 1H), 3.21 (m, 1H), 3.28-3.49 (m, 2H), 3.55 (m, 1H), 3.68 (m, 1H), 3.88 (m, 1H), 4.46 (m, 1H).

Example 59

Ethyl 1-(2-adamantylcarbamoyl)-4-(phenylamino)piperidine-4-carboxylate

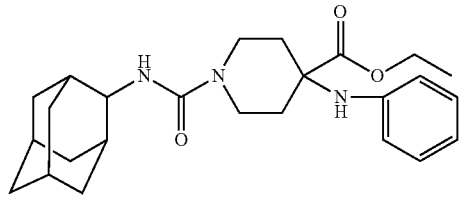 [SMILES: CCOC(=O)C1(Nc2ccccc2)CCN(C(=O)NC2C3CC4CC(C3)CC2C4)CC1]

The title compound was prepared following a procedure analogous to that described in Example 58 using ethyl 4-(phenylamino)piperidine-4-carboxylate in place of tert-butyl 1,7-diazaspiro[4.4]nonane-1-carboxylate (100 mg, 0.38 mmol). LC-MS Method 4, $t_R$=2.61 min, m/z=426.3; $^1$H NMR (CD$_3$OD) 1.14 (t, 3H), 1.61 (d, 2H), 1.62-1.90 (m, 8H), 1.91-2.02 (m, 5H), 2.02-2.21 (m, 4H), 3.48 (m, 2H), 3.61 (m, 2H), 3.82 (s, 1H), 4.13 (m, 2H), 6.71 (d, 2H), 6.78 (t, 1H), 7.15 (t, 2H).

Example 60 tert-butyl 1-(2-adamantylcarbamoyl)-3-phenylpyrrolidin-3-ylcarbamate

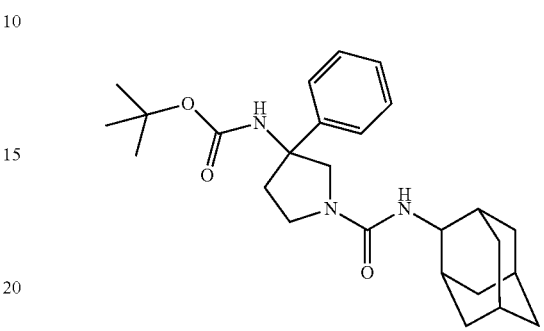

The title compound was prepared following a procedure analogous to that described in Example 46 using tert-butyl 3-phenylpyrrolidin-3-ylcarbamate. LC-MS Method 1, $t_R$=2.05 min, m/z=440; $^1$H NMR (CDCl$_3$) 1.35 (br s, 9H), 1.60-2.00 (14H), 2.33 (m, 1H), 2.70 (1H), 3.50 (1H), 3.57 (m, 1H), 3.74 (1H), 3.90 (1H), 3.98 (d, 1H), 4.62 (d, 1H), 5.17 (1H), 7.20-7.40 (5H).

Example 61

(R)-3-(5-cyanopyridin-2-ylamino)-N-(2-adamantyl)pyrrolidine-1-carboxamide

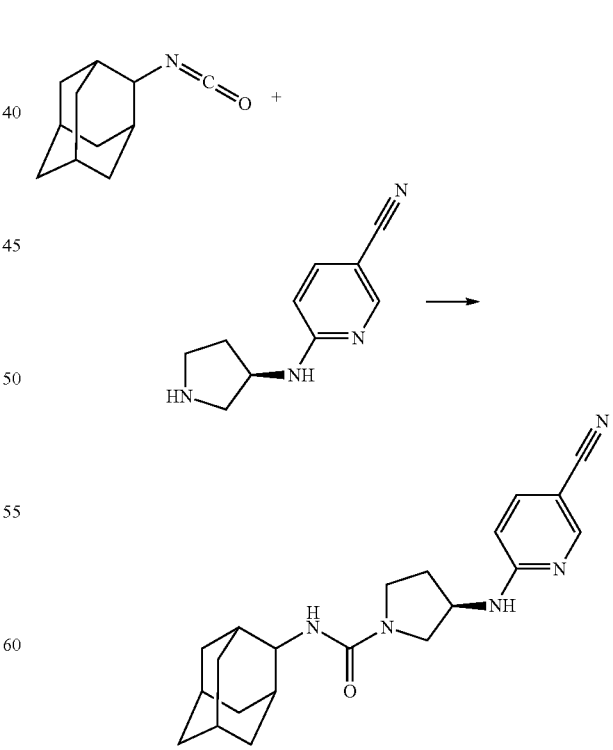

The title compound was prepared using the procedure of Example 46. LC-MS Method 1, $t_R$=1.68 min, m/z=366; $^1$H NMR (CD₃OD) 1.62 (2H), 1.75-2.05 (13H), 2.28 (m, 1H), 3.33 (m, 1H), 3.50 (m, 2H), 4.74 (m, 1H), 3.84 (s, 1H), 4.56 (m, 1H), 6.60 (d, 1H), 7.62 (d, 1H), 8.37 (s, 1H)

Example 62

(R)-(1-carbamoyl-4-adamantyl) 3-(pyrimidin-2-ylamino)pyrrolidine-1-carboxylate

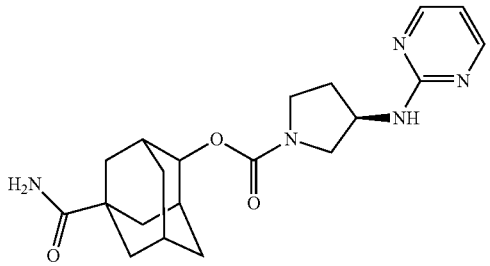 [SMILES: NC(=O)C12CC3CC(C1)C(OC(=O)N1CC[C@@H](Nc4ncccn4)C1)C(C3)C2]

The title compound was prepared following a procedure analogous to that described in Example 33 Step 2 using (3R)-(1-carbamoyl-4-adamantyl) 3-aminopyrrolidine-1-carboxylate and 2-chloropyrimidine. Two isomers were isolated.

Isomer 1: LC-MS Method 3 $t_R$=0.939 min, m/z=386; ¹H NMR (CD₃OD) 1.62-1.77 (m, 5H), 1.79 (m, 4H), 1.92 (m, 3H), 2.11 (m, 5H), 2.23 (m, 1H), 3.09 (m, 2H), 3.42 (m, 2H), 3.55 (m, 2H), 3.61-3.79 (m, 2H), 4.02-4.19 (m, 1H), 4.46 (m, 1H), 4.72 (m, 1H), 6.61 (m, 1H) 8.28 (m, 2H).

Isomer 2: LC-MS Method 3 $t_R$=0.973 min, m/z=386; ¹H NMR (CD₃OD) 1.49-1.59 (m, 4H), 1.88 (m, 2H), 1.94 (m, 5H), 2.09 (m, 4H), 2.21 (m, 3H), 3.09-3.21 (m, 2H), 3.39-3.51 (m, 2H), 3.53 (m, 1H), 3.69 (m, 2H), 4.06 (m, 1H), 4.44 (m, 1H), 4.72 (m, 1H), 6.61 (m, 1H) 8.28 (m, 2H).

Example 63

(R)-(trans-1-carbamoyl-4-adamantyl) 3-(3-fluoropyridin-2-ylamino)pyrrolidine-1-carboxylate

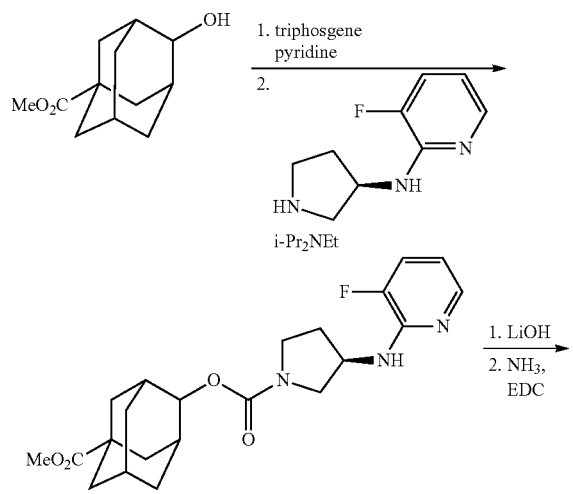

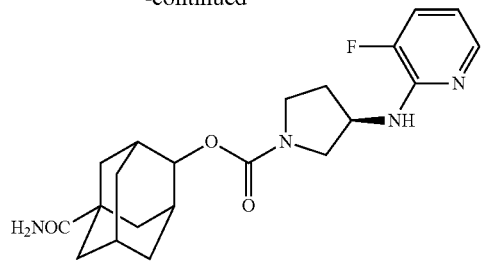

The title compound was prepared employing a procedure analogous to Example 14 Step 1 using (R)-3-fluoro-N-(pyrrolidin-3-yl)pyridin-2-amine, followed by procedures analogous to Example 16 Steps 1 and 2 and was isolated as a mixture of cis and trans isomers. LC-MS Method 1, $t_R$=1.2 min, m/z=403; ¹H NMR (CD₃OD) 1.58 (m, 2H), 1.85-2.15 (12H), 2.37 (m, 1H), 3.45-3.95 (4H), 4.44 (m, 1H), 4.80 (s, 1H), 6.86 (m, 1H), 7.68 (m, 1H), 7.79 (d, 1H)

Example 64

(3S) (trans-1-carbamoyl-4-adamantyl) 3-(tert-butoxycarbonylamino)pyrrolidine-1-carboxylate

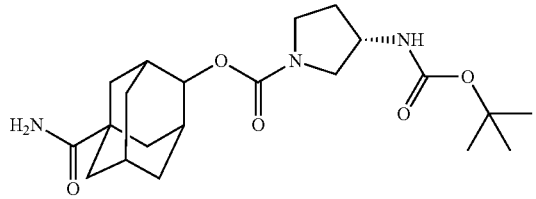 [SMILES: CC(C)(C)OC(=O)N[C@H]1CCN(C(=O)OC2C3CC4CC2CC(C(N)=O)(C4)C3)C1]

The title compound was prepared from (S)-tert-butyl pyrrolidine-3-carboxylate and 1-(methoxycarbonyl)-4-adamantyl chloroformate using a procedure analogous to that in Example 14, followed by procedures analogous to those described in Example 16. The isomer with the longer retention time on reverse phase HPLC was isolated. LC-MS Method 1, $t_R$=1.43 min, m/z=407; ¹H NMR (CDCl₃) 1.44 (s, 9H), 1.51 (m, 2H), 1.80-2.25 (13H), 3.28 (m, 1H), 3.47 (m, 2H), 3.66 (m, 1H), 4.23 (br s, 1H), 4.76 (br s, 1H), 4.83 (s, 1H), 5.82 (br s, 1H), 6.07 (br s, 1H).

Example 65

(S)-(trans-1-carbamoyl-4-adamantyl) 3-(5-cyanopyridin-2-ylamino)pyrrolidine-1-carboxylate

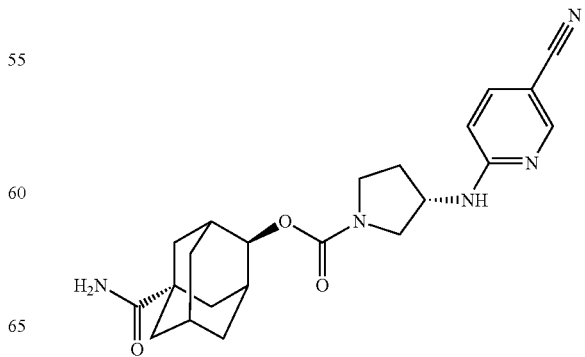

The title compound was prepared from the product of Example 64 following a procedure analogous to that described in Example 33 using 5-cyano-2-fluoropyridine in Step 2. LC-MS Method 1, $t_R$=1.35 min, m/z=410; $^1$H NMR (CD$_3$OD) 1.57 (m, 2H), 1.85-2.15 (12H), 2.27 (m, 1H), 3.30-3.85 (4H), 4.50 (m, 1H), 4.79 (s, 1H), 6.69 (d, 1H), 7.70 (d, 1H), 8.38 (s, 1H)

Example 66

(S)-(trans-1-carbamoyl-4-adamantyl) 3-(3-cyanopyridin-2-ylamino)pyrrolidine-1-carboxylate

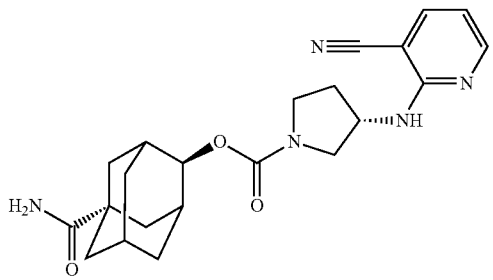 [SMILES: N#Cc1cccnc1N[C@H]1CCN(C(=O)O[C@H]2C3CC4CC2C[C@](C(N)=O)(C4)C3)C1]

The title compound was prepared from the product of Example 64 following a procedure analogous to that described in Example 33 using 3-cyano-2-fluoropyridine in Step 2. LC-MS Method 1, $t_R$=1.42 min, m/z=410; $^1$H NMR (CD$_3$OD) 1.58 (m, 2H), 1.85-2.15 (12H), 2.30 (m, 1H), 3.30-3.90 (4H), 4.62 (m, 1H), 4.80 (s, 1H), 6.77 (dd, 1H), 7.88 (d, 1H), 8.27 (d, 1H)

Example 67

(trans-1-carbamoyl-4-adamantyl) 3-(3-cyanopyridin-2-ylamino)-3-methylpyrrolidine-1-carboxylate

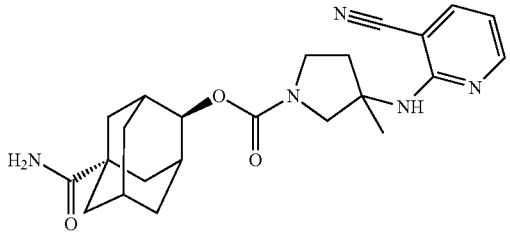 [SMILES: CC1(Nc2ncccc2C#N)CCN(C(=O)O[C@H]2C3CC4CC2C[C@](C(N)=O)(C4)C3)C1]

The title compound was prepared from 1-carbamoyl-4-adamantyll 3-(tert-butoxycarbonylamino)-3-methylpyrrolidine-1-carboxylate isomer 2 (Example 22) following a procedure analogous to that described in Example 33 using 3-cyano-2-fluoropyridine in Step 2. LC-MS Method 1, $t_R$=1.55 min, m/z=424; $^1$H NMR (CD$_3$OD) [selected resonances] 2.45 (m, 1H), 3.90 (d, 0.5H), 4.13 (d, 0.5H), 6.69 (m, 1H), 7.79 (d, 1H), 8.27 (d, 1H).

Example 68

(1-carbamoyl-4-adamantyl) 4-(3-cyanopyridin-2-ylamino)piperidine-1-carboxylate

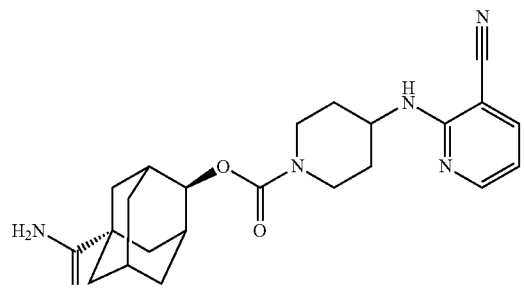

The title compound was prepared from 2-adamantyl chloroformate and 2-(piperidin-4-ylamino)nicotinonitrile following procedures analogous to those described in Example 63. LC-MS Method 1, $t_R$=1.48 min, m/z=424; $^1$H NMR (CD$_3$OD) 1.60 (m, 4H), 1.85-2.15 (13H), 3.02 (m, 2H), 4.20 (m, 3H), 4.79 (s, 1H), 6.75 (dd, 1H), 7.92 (d, 1H), 8.22 (d, 1H).

Example 69

(trans-1-carbamoyl-4-adamantyl) 3-(5-cyanopyridin-2-ylamino)-3-methylpyrrolidine-1-carboxylate

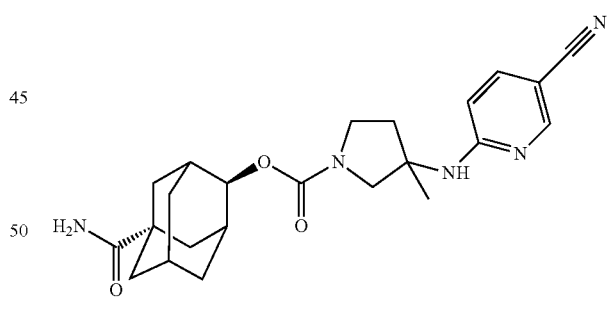

The title compound was prepared from 1-carbamoyl-4-adamantyll 3-(tert-butoxycarbonylamino)-3-methylpyrrolidine-1-carboxylate isomer 2 (Example 22) following a procedure analogous to that described in Example 33 using 5-cyano-2-fluoropyridine in Step 2. LC-MS Method 1, $t_R$=1.5 min, m/z=424; $^1$H NMR (CD$_3$OD) 1.28 (s, 3H), 1.58 (m, 2H), 1.80-2.15 (11H), 2.41 (m, 2H), 3.30-3.60 (3H), 3.91 (d, 0.5H), 4.13 (d, 0.5H), 4.73 (0.5H), 4.78 (0.5H), 6.58 (d, 1H), 7.56 (d, 1H), 8.34 (s, 1H).

Example 70

(R)-(1-(methoxycarbonyl)-4-adamantyl) 3-(3-cyanopyridin-2-ylamino)pyrrolidine-1-carboxylate

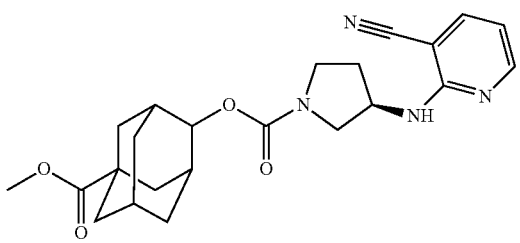 [SMILES: COC(=O)C12CC3CC(C1)C(OC(=O)N1CC[C@@H](Nc4ncccc4C#N)C1)C(C3)C2]

The title compound was prepared from 2-adamantyl chloroformate and (R)-2-(pyrrolidin-3-ylamino)nicotinonitrile following procedures analogous to those described in Example 63 Step 1. LC-MS Method 1, $t_R$=1.8 min, m/z=425; $^1$H NMR (CDCl$_3$) [selected resonances] 3.66 (s, 3H), 5.25 (m, 1H), 6.67 (m, 1H), 7.70 (m, 1H), 8.32 (m, 1H)

Example 71

(3R)-3-carbamoylbicyclo[3.3.1]nonan-9-yl 3-(5-(trifluoromethyl)pyridin-2-ylamino)pyrrolidine-1-carboxylate

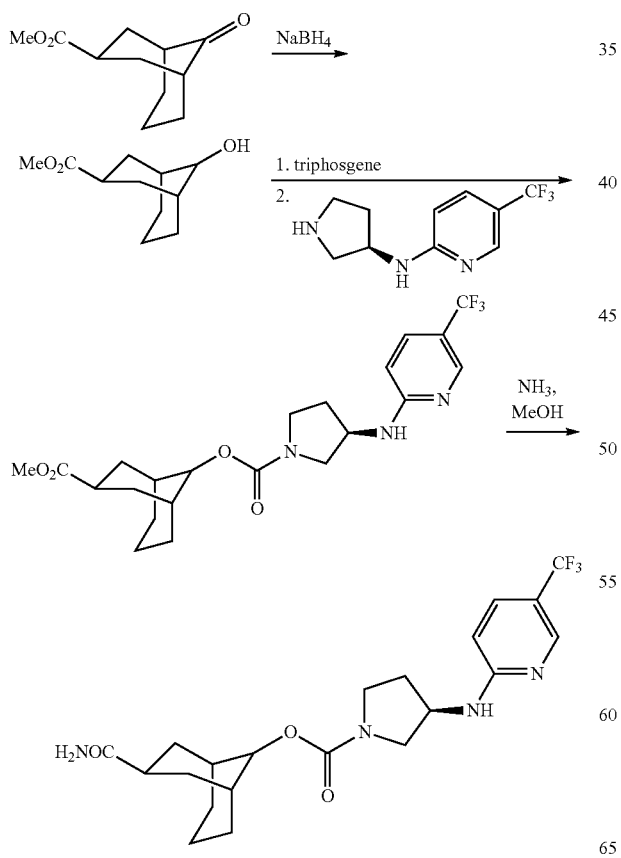

Step 1

To a solution of methyl 9-oxobicyclo[3.3.1]nonane-3-carboxylate (190 mg, 0.97 mmol) in methanol was added NaBH$_4$ (76 mg, 2 mmol) at 0° C. The mixture was stirred at rt for 2 h, and concentrated. The residue was diluted with water, and the mixture was extracted with Et$_2$O. The organic layer was concentrated to give methyl 9-hydroxybicyclo-[3.3.1]nonane-3-carboxylate, which was used in the next step directly without purification (140 mg, crude).

Step 2

To a solution of methyl 9-hydroxybicyclo[3.3.1]nonane-3-carboxylate (140 mg, crude) and Et$_3$N (0.28 mL, 2.02 mmol) in CH$_2$Cl$_2$ was added triphosgene (293 mg, 1 mmol) at 0° C. After the mixture was stirred at 0° C. for 1 h, a solution of (R)—N-(pyrrolidin-3-yl)-5-(trifluoromethyl)pyridin-2-amine (128.3 mg, 0.56 mmol) was added. The mixture was stirred at rt for 2 h, added water, and extracted with CH$_2$Cl$_2$. The combined organic layer was concentrated, and purified by prep TLC to give (3R)-3-(ethoxycarbonyl)bicyclo[3.3.1]nonan-9-yl 3-(5-(trifluoromethyl)-pyridin-2-ylamino)pyrrolidine-1-carboxylate (100 mg, 44%). $^1$H NMR (CDCl$_3$): δ 1.47 (m, 4H), 1.92 (m, 8H), 2.22 (m, 2H), 3.01 (m, 1H), 3.29 (m, 1H), 3.52 (m, 2H), 3.60 (s, 3H), 3.73 (m, 1H), 4.40 (m, 1H), 4.68 (s, 1H), 6.40 (d, 1H), 7.55 (d, 1H), 8.3 (s, 1H).

Step 3

A mixture of (3R)-3-(ethoxycarbonyl)bicyclo[3.3.1]nonan-9-yl-3-(5-(trifluoro methyl)pyridin-2-ylamino)pyrrolidine-1-carboxylate (100 mg, 0.22 mmol) and NH$_3$/MeOH (20 mL) was stirred at room temperature for 72 h. The reaction mixture was concentrated, and purified by preparative HPLC to afford (3R)-3-carbamoylbicyclo[3.3.1]nonan-9-yl 3-(5-(trifluoromethyl)pyridin-2-ylamino)pyrrolidine-1-carboxylate (1.53 mg, 2%). LC-MS Method 3 $t_R$=1.19 min, m/z=441. $^1$H NMR (CDCl$_3$): δ 1.48 (m, 3H), 1.68-1.99 (m, 11H), 2.21 (m, 2H), 2.81 (s, 1H), 3.01 (m, 1H), 3.48 (m, 4H), 3.68 (m, 1H), 4.40 (s, 1H), 4.62 (s, 1H), 6.60 (d, 1H), 7.56 (d, 1H), 8.16 (s, 1H).

Example 72

(3R) (1-carbamoyl-4-adamantyl) 3-(5-cyanothiazol-2-ylamino)pyrrolidine-1-carboxylate

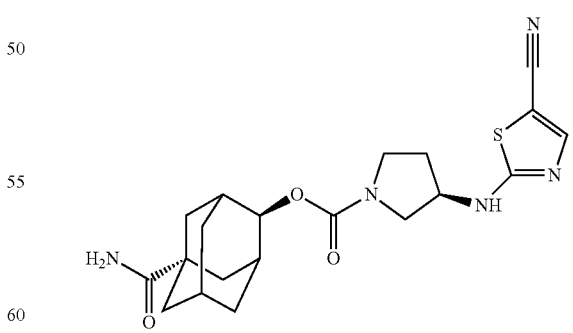

The title compound was prepared from (3R) (1-carbamoyl-4-adamantyl) 3-(tert-butoxycarbonylamino)pyrrolidine-1-carboxylate isomer 2 following procedures analogous to those described in Example 33 using 2-chloro-5-cyanothiazole in Step 2. LC-MS Method 1 $t_R$=1.32 min, m/z=415; $^1$H NMR (CD₃OD) 1.55 (2H), 1.85-2.15 (12H), 2.25 (m, 1H), 3.35-3.80 (4H), 4.40 (br s, 1H), 4.78 (s, 1H), 7.74 (s, 1H).

Example 73

(3R) (trans-1-cyano-4-adamantyl) 3-(3-cyanopyridin-2-ylamino)pyrrolidine-1-carboxylate

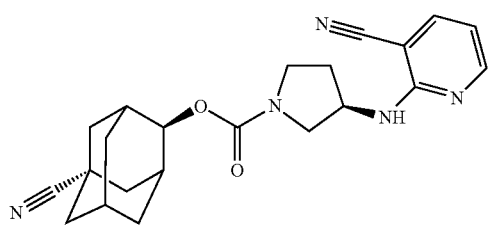 [SMILES: N#Cc1cccnc1N[C@@H]1CCN(C(=O)O[C@H]2C3CC4CC2C[C@](C#N)(C4)C3)C1]

The title compound was prepared from (R)-(1-carbamoyl-4-adamantyl) 3-(3-cyanopyridin-2-ylamino)pyrrolidine-1-carboxylate following a procedure analogous to that described in Example 19. LC-MS Method 1 $t_R$=1.75 min, m/z=392; ¹H NMR (CD₃OD) 1.60 (2H), 1.90-2.20 (12H), 2.28 (m, 1H), 3.35-3.90 (4H), 4.64 (m, 1H), 4.79 (s, 1H), 6.72 (m, 1H), 7.80 (m, 1H), 8.29 (m, 1H).

Example 74

(trans-1-carbamoyl-4-adamantyl) 3-((5-cyanopyridin-2-yl)(methyl)amino)pyrrolidine-1-carboxylate

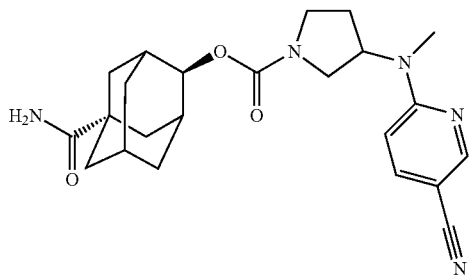 [SMILES: CN(c1ccc(C#N)cn1)C1CCN(C(=O)O[C@H]2C3CC4CC2C[C@](C(N)=O)(C4)C3)C1]

The title compound was prepared from 3-(tert-butoxycarbonyl-methyl-amino)-pyrrolidine-1-carboxylic acid 5-carbamoyl-adamantan-2-yl ester isomer 2 following procedures analogous to those described in Example 33 using 5-cyano-2-fluoropyridine in Step 2. LC-MS Method 1 $t_R$=1.45 min, m/z=424; ¹H NMR (CD₃OD) 1.57 (2H), 1.85-2.25 (13H), 3.03 (s, 3H), 3.30-3.80 (4H), 4.79 (s, 1H), 5.38 (m, 1H), 6.84 (d, 1H), 7.78 (dd, 1H), 8.44 (d, 1H).

Example 75

(trans-1-carbamoyl-4-adamantyl) 1-(5-cyanopyridin-2-yl)-1,7-diazaspiro[4.4]nonane-7-carboxylate

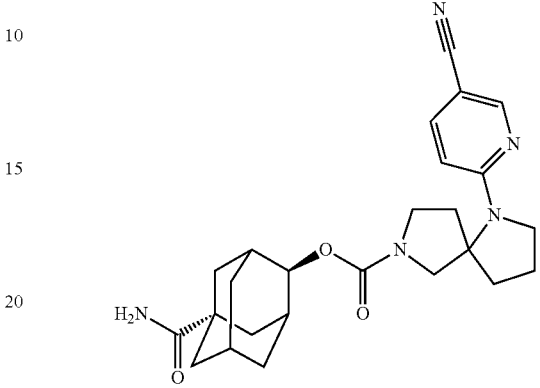

The title compound was prepared from 1-tert-butyl 7-(1-carbamoyl-4-adamantyl) 1,7-diazaspiro[4.4]nonane-1,7-dicarboxylate isomer 2 following procedures analogous to those described in Example 33 using 5-cyano-2-fluoropyridine in Step 2. LC-MS Method 1 $t_R$=1.65 min, m/z=450; ¹H NMR (CD₃OD) [selected resonances] 4.80 (s, 1H), 6.59 (d, 1H), 7.72 (dd, 1H), 8.39 (d, 1H).

Example 76

(trans-1-carbamoyl-4-adamantyl) 1-(5-cyanopyridin-2-yl)hexahydropyrrolo[3,4-b]pyrrole-5(1H)-carboxylate

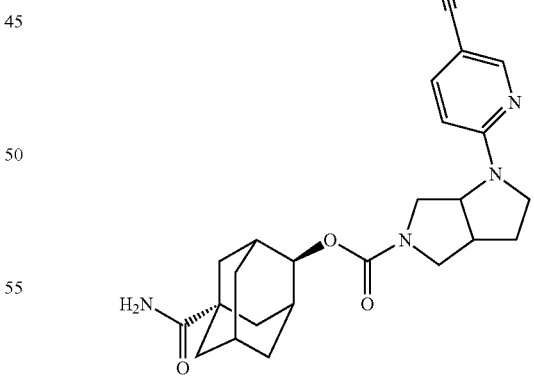

The title compound was prepared from 1-tert-butyl 5-(1-carbamoyl-4-adamantyl) hexahydropyrrolo[3,4-b]pyrrole-1,5-dicarboxylate isomer 2 following procedures analogous to those described in Example 33 using 5-cyano-2-fluoropyridine in Step 2. LC-MS Method 1 $t_R$=1.42 min, m/z=436; ¹H NMR (CD₃OD) [selected resonances] 4.59 (m, 1H), 4.75 (m, 1H), 6.65 (d, 1H), 7.78 (dd, 1H), 8.43 (d, 1H).

Example 77

(R)-(1-hydroxy-4-adamantyl) 3-(tert-butoxycarbonylamino)pyrrolidine-1-carboxylate

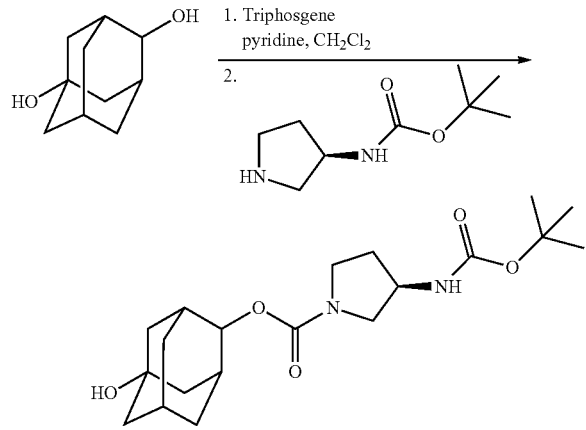

A stirred solution of 1,4-dihydroxyadamantane (858 mg, 5.10 mmol) in CH$_2$Cl$_2$ (30 mL) and dry pyridine (10 mL) was cooled in an ice-salt bath and a solution of triphosgene (500 mg, 1.68 mmol) in CH$_2$Cl$_2$ (10 mL) was added dropwise over 5 min. The mixture was stirred in the ice bath for 2.5 h. (R)-tert-butyl pyrrolidin-3-ylcarbamate (949 mg, 5.1 mmol) was added to the mixture. The cooling bath was allowed to expire and the mixture was stirred overnight at rt. The mixture was concentrated. The residue was taken up in EtOAc (100 mL) and washed with water (15 mL) and brine (15 mL), and dried over Na$_2$SO$_4$. Removal of the solvent left a white foam (1.57 g) which was purified by chromatography on a 40-g silica gel cartridge eluted with a 20 to 100% EtOAc in hexanes gradient to afford two isomeric products.

Isomer 1: (R)-(cis-1-hydroxy-4-adamantyl) 3-(tert-butoxycarbonylamino)pyrrolidine-1-carboxylate (512 mg, 26%). LC-MS Method 1 t$_R$=1.39 min, m/z=381; $^1$H NMR (CDCl$_3$) [selected resonances] 1.43 (s, 9H), 3.23 (m, 1H), 3.48 (m, 2H), 3.67 (m, 1H), 4.22 (1H), 4.63 (1H), 4.73 (s, 1H).

Isomer 2: (R)-(trans-1-hydroxy-4-adamantyl) 3-(tert-butoxycarbonylamino)pyrrolidine-1-carboxylate (475 mg, 24%). LC-MS Method 1 t$_R$=1.45 min, m/z=381; $^1$H NMR (CDCl$_3$) [selected resonances] 1.44 (s, 9H), 3.25 (dd, 1H), 3.48 (m, 2H), 3.66 (m, 1H), 4.22 (1H), 4.62 (1H), 4.82 (s, 1H).

Example 78

(R)-(trans-1-hydroxy-4-adamantyl) 3-(4-cyanophnylamino)pyrrolidine-1-carboxylate

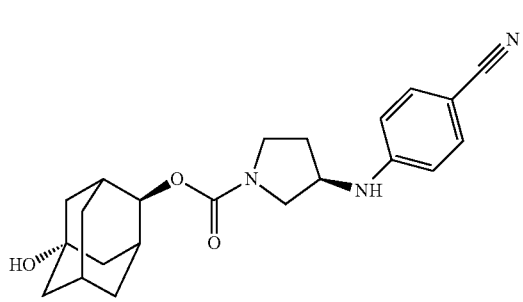 [SMILES: N#Cc1ccc(N[C@@H]2CCN(C(=O)O[C@H]3C4CC5CC3C[C@](O)(C5)C4)C2)cc1]

Step 1

(R)-(trans-1-hydroxy-4-adamantyl) 3-(tert-butoxycarbonylamino)pyrrolidine-1-carboxylate (Example 77 Isomer 2, 472 mg, 1.2 mmol) was dissolved in CH$_2$Cl$_2$ (15 mL) and trifluoroacetic acid (5 mL) was added. The mixture was stirred at rt for 5 h and concentrated under reduced pressure. The residue was dissolved in MeOH (50 mL) and treated with Amberlyst A26 OH$^-$ (ca. 10 g). The mixture was filtered and the filtrate was concentrated to afford (R)-(trans-1-hydroxy-4-adamantyl) 3-aminopyrrolidine-1-carboxylate (319 mg, 92%) as an oil. LC-MS Method 1 t$_R$=0.56 min, m/z=281.

Step 2

A heavy-walled glass vial was charged with 4-cyanophenylboronic acid (21 mg, 0.14 mmol), Cu(OAc)$_2$.H$_2$O (3 mg, 0.014 mmol), 4 Å molecular sieves (54 mg) and dry CH$_2$Cl$_2$ (1 mL). The mixture was stirred at rt for 5 min and (R)-(trans-1-hydroxy-4-adamantyl) 3-aminopyrrolidine-1-carboxylate (20 mg, 0.07 mmol) was added. The mixture was stirred under O$_2$ at 40° C. for 30 h. The mixture was diluted with CH$_2$Cl$_2$ (5 mL) and filtered. The filtrate was concentrated and the residue was purified by prep HPLC to afford (R)-(trans-1-hydroxy-4-adamantyl) 3-(4-cyanophenylamino)pyrrolidine-1-carboxylate (0.4 mg, 1.5%) as an oil. LC-MS Method 1 t$_R$=1.52 min, m/z=382; $^1$H NMR (CD$_3$OD) [selected resonances] 6.69 (d, 2H), 7.41 (d, 2H).

Example 79

(R)-(1-hydroxy-4-adamantyl) 3-(5-cyanopyridin-2-ylamino)pyrrolidine-1-carboxylate

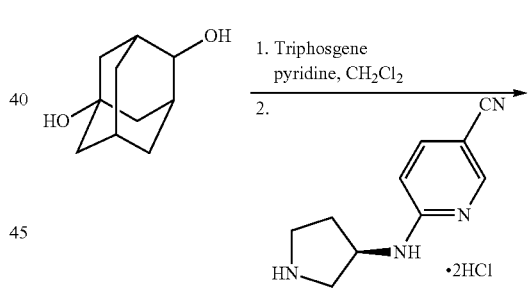

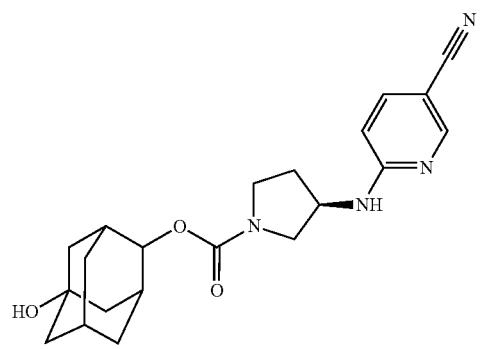

A stirred solution of 1,4-dihydroxyadamantane (41 mg, 0.24 mmol) in CH$_2$Cl$_2$ (1.5 mL) and dry pyridine (0.5 mL) was cooled in an ice-salt bath and a solution of triphosgene (24 mg, 0.08 mmol) in CH$_2$Cl$_2$ (3 mL) was added dropwise over 2 min. The mixture was stirred in the ice bath for 2 h and (R)-6-(pyrrolidin-3-ylamino)nicotinonitrile (63 mg, 0.24 mmol) was added. The cooling bath was allowed to expire and the mixture was stirred overnight at rt. The mixture was diluted with EtOAc (90 mL), washed with water (15 mL) and brine (15 mL), and dried over Na$_2$SO$_4$. Removal of the solvent left an oil (69 mg) which was purified by prep HPLC to afford two isomers of the desired product.

Isomer 1: (R)-(cis-1-hydroxy-4-adamantyl) 3-(5-cyanopyridin-2-ylamino)pyrrolidine-1-carboxylate (11 mg, 12%). LC-MS Method 1 t$_R$=1.3 min, m/z=383; $^1$H NMR (CD$_3$OD) 1.52 (m, 2H), 1.70 (6H), 2.00 (4H), 2.10-2.35 (3H), 3.30-3.85 (4H), 3.50 (m, 1H), 4.66 (s, 1H), 6.65 (d, 1H), 7.67 (d, 1H), 8.37 (s, 1H).

Isomer 2: (R)-(trans-1-hydroxy-4-adamantyl) 3-(5-cyanopyridin-2-ylamino)pyrrolidine-1-carboxylate (31 mg, 33%). LC-MS Method 1 t$_R$=1.37 min, m/z=383; $^1$H NMR (CD$_3$OD) 1.43 (m, 2H), 1.70-2.20 (12H), 2.26 (m, 1H), 3.30-3.80 (4H), 4.50 (m, 1H), 4.77 (s, 1H), 6.66 (d, 1H), 7.65 (d, 1H), 8.37 (s, 1H).

Example 80

(R)-(trans-1-hydroxy-4-adamantyl) 3-(3-cyanopyridin-2-ylamino)pyrrolidine-1-carboxylate

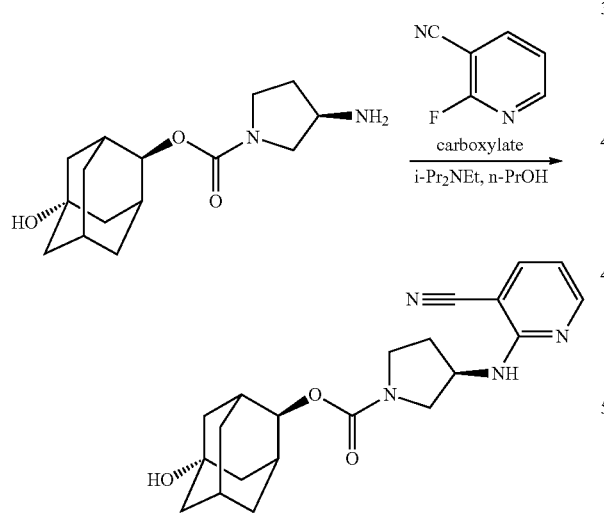

A microwave vial was charged with (R)-(trans-1-hydroxy-4-adamantyl) 3-aminopyrrolidine-1-carboxylate (10 mg, 0.036 mmol), i-Pr$_2$NEt (0.013 mL, 0.071 mmol), 2-fluoro-3-cyanopyridine (6.5 mg, 0.054 mmol) and n-PrOH (1 mL) was heated in the microwave at 160° C. for 4 h. Prep HPLC afforded the title compound (11.9 mg, 67%) as its TFA salt. LC-MS Method 1 t$_R$=1.45 min, m/z=383; $^1$H NMR (CD$_3$OD) 1.44 (m, 2H), 1.70-2.20 (12H), 2.28 (m, 1H), 3.35-3.90 (4H), 4.63 (m, 1H), 4.78 (s, 1H), 6.75 (m, 1H), 6.85 (m, 1H), 8.29 (m, 1H).

Example 81

(R)-(trans-1-hydroxy-4-adamantyl) 3-(6-cyanopyrazin-2-ylamino)pyrrolidine-1-carboxylate

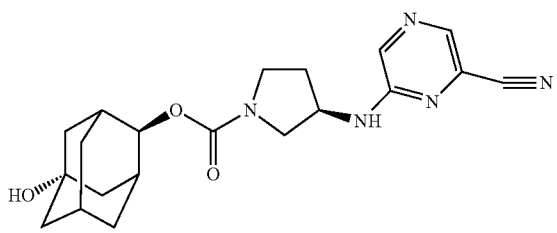 [SMILES: N#Cc1cncc(N[C@@H]2CCN(C(=O)O[C@H]3C4CC5CC3C[C@](O)(C5)C4)C2)n1]

The title compound was prepared by the procedure of Example 80 using 2-chloro-6-cyanopyrazine. LC-MS Method 1 t$_R$=1.4 min, m/z=384.

Example 82

(R)-(trans-1-hydroxy-4-adamantyl) 3-(5-cyanothiazol-2-ylamino)pyrrolidine-1-carboxylate

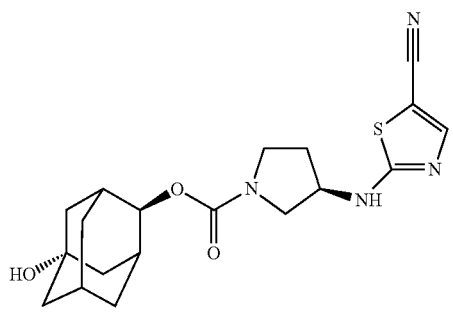 [SMILES: N#Cc1cnc(N[C@@H]2CCN(C(=O)O[C@H]3C4CC5CC3C[C@](O)(C5)C4)C2)s1]

The title compound was prepared by the procedure of Example 80 using 2-chloro-5-cyanothiazole. LC-MS Method 1 t$_R$=1.35 min, m/z=389; $^1$H NMR (CD$_3$OD) [selected resonances] 4.40 (m, 1H), 7.73 (s, 1H).

Example 83

(R)-(trans-1-hydroxy-4-adamantyl) 3-(3-cyano-6-methylpyridin-2-ylamino)pyrrolidine-1-carboxylate

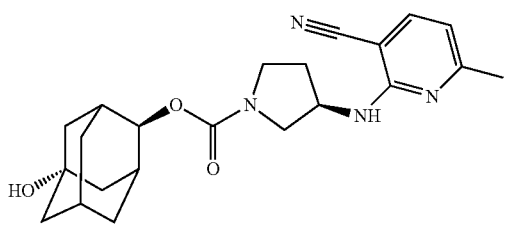 [SMILES: Cc1ccc(C#N)c(N[C@@H]2CCN(C(=O)O[C@H]3C4CC5CC3C[C@](O)(C5)C4)C2)n1]

The title compound was prepared by the procedure of Example 80 using 2-chloro-3-cyano-6-methylpyridine. LC-MS Method 1 $t_R$=1.63 min, m/z=397; $^1$H NMR (CD$_3$OD) [selected resonances] 4.70 (m, 1H), 6.60 (d, 1H), 7.58 (d, 1H).

Example 84

(R)-(trans-1-hydroxy-4-adamantyl) 3-(5-cyano-6-methylpyridin-2-ylamino)pyrrolidine-1-carboxylate

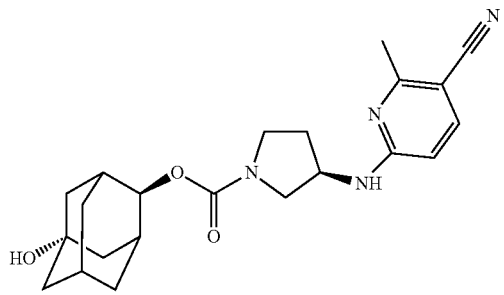 [SMILES: Cc1nc(N[C@@H]2CCN(C(=O)O[C@H]3C4CC5CC3C[C@](O)(C5)C4)C2)ccc1C#N]

The title compound was prepared by the procedure of Example 80 using 6-fluoro-2-methylnicotinonitrile. LC-MS Method 1 $t_R$=1.48 min, m/z=397; $^1$H NMR (CD$_3$OD) 1.45 (m, 2H), 1.70-2.20 (12H), 2.28 (m, 1H), 2.57 (s, 3H), 2.40-2.80 (4H), 4.55 (1H), 4.77 (s, 1H), 6.55 (m, 1H), 7.61 (m, 1H).

Example 85

(R)-(trans-1-hydroxy-4-adamantyl) 3-(quinazolin-4-ylamino)pyrrolidine-1-caboxylate

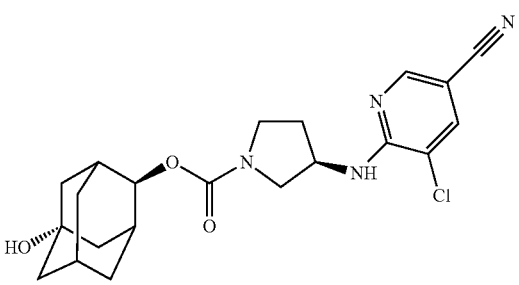 [SMILES: N#Cc1cnc(N[C@@H]2CCN(C(=O)O[C@H]3C4CC5CC3C[C@](O)(C5)C4)C2)c(Cl)c1]

The title compound was prepared by the procedure of Example 80 using 4-chloroquinazoline and heating at 120° C. for 2 h. LC-MS Method 1 $t_R$=1.03 min, m/z=409; $^1$H NMR (CD$_3$OD) 1.44 (m, 2H), 1.70-2.35 (12H), 2.44 (m, 1H), 3.50-4.05 (4H), 4.80 (s, 1H), 5.17 (m, 1H), 7.81 (m, 2H), 8.07 (m, 1H), 8.52 (d, 1H), 8.83 (s, 1H)

Example 86

(R)-(trans-1-hydroxy-4-adamantyl) 3-(5-chloro-3-cyanopyridin-2-ylamino)pyrrolidine-1-carboxylate

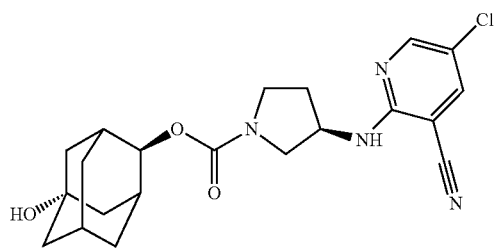 [SMILES: N#Cc1cc(Cl)cnc1N[C@@H]1CCN(C(=O)O[C@H]2C3CC4CC2C[C@](O)(C4)C3)C1]

The title compound was prepared by the procedure of Example 80 using 2,5-dichloronicotinonitrile. LC-MS Method 1 $t_R$=1.7 min, m/z=419, 417; $^1$H NMR (CD$_3$OD) 1.47 (m, 2H), 1.70-2.20 (12H), 2.27 (m, 1H), 3.35-3.90 (4H), 4.64 (m, 1H), 4.77 (s, 1H), 7.90 (s, 1H), 8.27 (s, 1H)

Example 87

(R)-(trans-1-hydroxy-4-adamantyl) 3-(3-chloro-5-cyanopyridin-2-ylamino)pyrrolidine-1-carboxylate

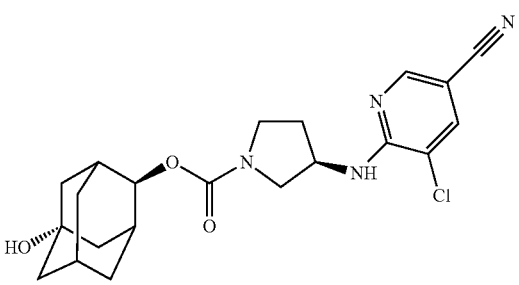 [SMILES: N#Cc1cnc(N[C@@H]2CCN(C(=O)O[C@H]3C4CC5CC3C[C@](O)(C5)C4)C2)c(Cl)c1]

The title compound was prepared by the procedure of Example 80 using 5,6-dichloronicotinonitrile. LC-MS Method 1 $t_R$=1.6 min, m/z=419, 417; $^1$H NMR (CD$_3$OD) 1.48 (m, 2H), 1.70-2.20 (12H), 2.29 (m, 1H), 3.40-3.90 (4H), 4.72 (m, 1H), 4.77 (s, 1H), 7.86 (s, 1H), 8.34 (s, 1H)

Example 88

(R)-(trans-1-hydroxy-4-adamantyl) 3-(5-methyl-1,6-naphthyridin-2-ylamino)pyrrolidine-1-carboxylate

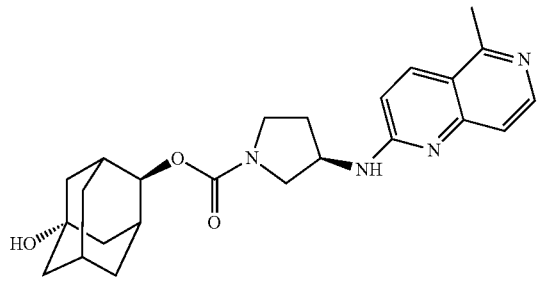 [SMILES: Cc1nccc2nc(N[C@@H]3CCN(C(=O)O[C@H]4C5CC6CC4C[C@](O)(C6)C5)C3)ccc12]

The title compound was prepared by the procedure of Example 80 using 2-chloro-5-methyl-1,6-naphthyridine. LC-MS Method 1 $t_R$=1.12 min, m/z=423; $^1$H NMR (CD$_3$OD) 1.40-2.40 (15H), 2.93 (s, 3H), 3.40-3.95 (4H), 4.78 (br s, 1H), 7.07 (d, 1H), 7.64 (d, 1H), 8.23 (d, 1H), 8.28 (d, 1H)

Example 89

(R)-(trans-1-hydroxy-4-adamantyl) 3-(3-(dimethyl-carbamoyl)pyridin-2-ylamino)prrolidine-1-carboxylate

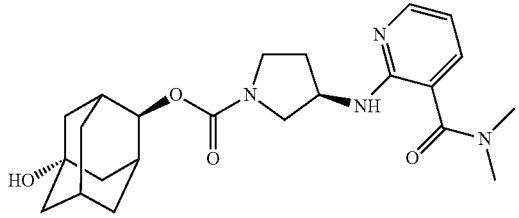 [SMILES: CN(C)C(=O)c1cccnc1N[C@@H]1CCN(C(=O)O[C@H]2C3CC4CC2C[C@](O)(C4)C3)C1]

The title compound was prepared by the procedure of Example 80 using 2-fluoro-N,N-dimethylnicotinamide. LC-MS Method 1 $t_R$=1.03 min, m/z=429; $^1$H NMR (CDCl$_3$) 1.35-2.35 (16H), 3.05 (s, 6H), 3.29 (m, 1H), 3.50 (m, 1H), 3.58 (m, 1H), 3.84 (m, 1H), 4.62 (m, 1H), 4.83 (s, 1H), 6.15 (m, 1H), 6.58 (m, 1H), 7.35 (m, 1H), 8.17 (m, 1H)

Example 90

(R)-(trans-1-hydroxy-4-adamantyl) 3-(6-cyanoquinolin-2-ylamino)pyrrolidine-1-carboxylate

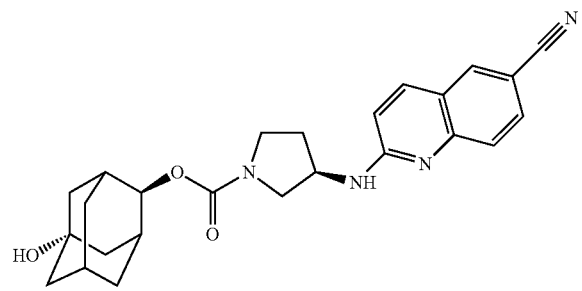 [SMILES: N#Cc1ccc2nc(N[C@@H]3CCN(C(=O)O[C@H]4C5CC6CC4C[C@](O)(C6)C5)C3)ccc2c1]

The title compound was prepared by the procedure of Example 80 using 2-chloro-6-cyanoquinoline. LC-MS Method 1 $t_R$=1.18 min, m/z=433; $^1$H NMR (CD$_3$OD) [selected resonances] 7.17 (br s, 1H), 7.96 (d, 1H), 8.03 (d, 1H), 8.28 (d, 1H), 8.32 (s, 1H)

Example 91

(R)-(trans-1-hydroxy-4-adamantyl) 3-(6-cyanoquinoxalin-2-ylamino)pyrrolidine-1-carboxylate

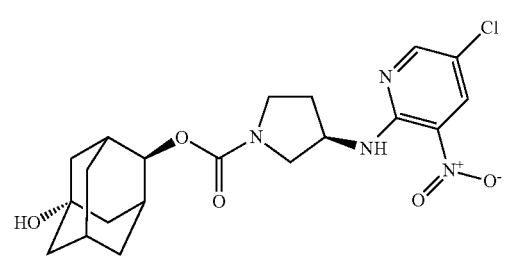 [SMILES: O=C(O[C@H]1C2CC3CC1C[C@](O)(C3)C2)N1CC[C@@H](Nc2ncc(Cl)cc2[N+](=O)[O-])C1]

The title compound was prepared by the procedure of Example 80 using 2-chloroquinoxaline-6-carbonitrile. LC-MS Method 1 $t_R$=1.52 min, m/z=434; $^1$H NMR (CD$_3$OD) 1.30-2.40 (15H), 3.5-3.9 (4H), 4.66 (br s, 1H), 4.78 (br s, 1H), 7.58 (d, 1H), 7.91 (d, 1H), 8.00 (s, 1H), 8.37 (s, 1H).

Example 92

(R)-(trans-1-hydroxy-4-adamantyl) 3-(5-carbamoyl-3-chloropyridin-2-ylamino)pyrrolidine-1-carboxylate The title compound was prepared by the procedure of Example 80 using 5,6-dichloronicotinamide. LC-MS Method 1 $t_R$=1.23 min, m/z=437, 435; $^1$H NMR (CD$_3$OD) 1.40-2.40 (15H), 3.40-3.90 (4H), 4.72 (1H), 4.78 (1H), 8.04 (s, 1H), 8.56 (s, 1H).

Example 93

(R)-(trans-1-hydroxy-4-adamantyl) 3-(5-chloro-3-nitropyridin-2-ylamino)pyrrolidine-1-carboxylate The title compound was prepared by the procedure of Example 80 using 2,5-dichloro-3-nitropyridine and heating at 120° C. for 2 h. LC-MS Method 1 $t_R$=1.77 min, m/z=439, 437; $^1$H NMR (CDCl$_3$) 1.44 (m, 2H), 1.70-2.25 (13H), 2.38 (m, 1H), 3.38 (m, 1H), 3.63 (m, 2H), 3.90 (m, 1H), 4.79 (m, 1H), 4.86 (s, 1H), 8.19 (br s, 1H), 8.39 (s, 1H), 8.42 (s, 1H), Example 94

(R)-(trans-1-hydroxy-4-adamantyl) 3-(6-cyanobenzo[d]thiazol-2-ylamino)pyrrolidine-1-carboxylate

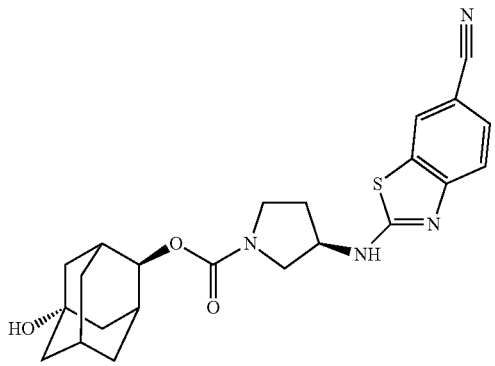 [SMILES: N#Cc1ccc2nc(N[C@@H]3CCN(C(=O)O[C@H]4C5CC6CC4C[C@](O)(C6)C5)C3)sc2c1]

The title compound was prepared by the procedure of Example 80 using 2-chlorobenzo[d]thiazole-6-carbonitrile heating in an oil bath a 115° C. for 16 h. $^1$H NMR (CD$_3$OD) 1.35-2.40 (15H), 3.5-3.8 (4H), 4.55 (br s, 1H), 4.78 (s, 1H), 7.54 (d, 1H), 7.62 (d, 1H), 8.05 (s, 1H).

Example 95

(R)-(trans-1-hydroxy-4-adamantyl) 3-(6-chloro-quinolin-2-ylamino)pyrrolidine-1-carboxylate

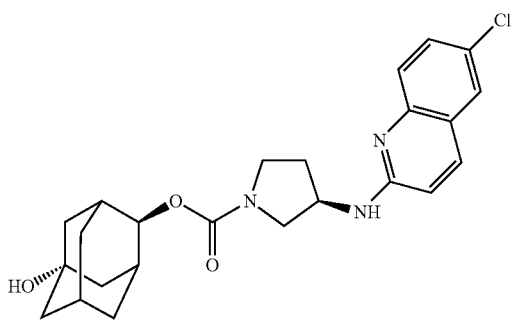 [SMILES: O=C(O[C@H]1C2CC3CC1C[C@](O)(C3)C2)N1CC[C@@H](Nc2ccc3cc(Cl)ccc3n2)C1]

The title compound was prepared by the procedure of Example 80 using 2,6-dichloroquinoline. LC-MS Method 1 $t_R$=1.23 min, m/z=444, 442.

Example 96

(R)-(trans-1-hydroxy-4-adamantyl) 3-(6-chloroquinoxalin-2-ylamino)pyrrolidine-1-carboxyate

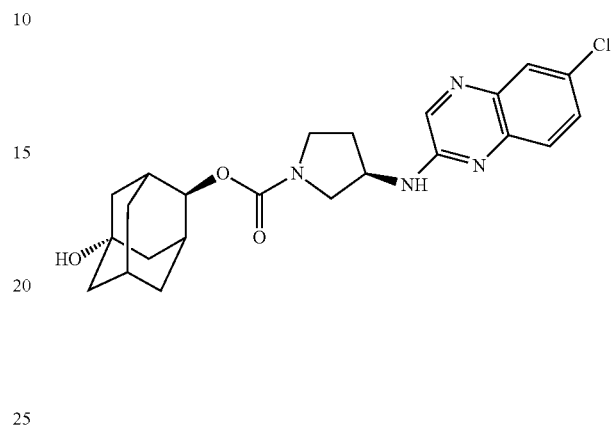

The title compound was prepared by the procedure of Example 80 using 2,6-dichloroquinoxaline. LC-MS Method $t_R$=min, m/z=; $^1$H NMR (CD$_3$OD) 1.35-2.40 (15H) 3.40-3.90 (4H), 4.62 (br s, 1H), 4.77 (s, 1H), 7.58 (d, 1H), 7.64 (d, 1H), 7.80 (s, 1H), 8.29 (s, 1H).

Example 97

(R)-(trans-1-hydroxy-4-adamantyl) 3-(6-chlorobenzo[d]thiazol-2-ylamino)pyrrolidine-1-carboxylate

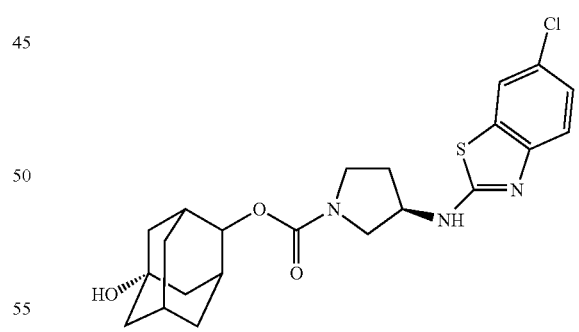

The title compound was prepared by the procedure of Example 80 using 2,6-dichlorobenzo[d]thiazole. LC-MS Method 1 $t_R$=1.73 min, m/z=450, 448; $^1$H NMR (CDCl$_3$) 1.42 (d, 2H), 1.70-2.25 (12H), 2.37 (m, 1H), 3.50-4.05 (4H), 4.84 (s, 2H), 7.42 (d, 1H), 7.52 (d, 1H), 7.63 (s, 1H).

Example 98

(R)-(trans-1-hydroxy-4-adamantyl) 3-(5-chloro-3-(methylcarbamoyl)pyridin-2-ylamino)pyrrolidine-1-carboxylate

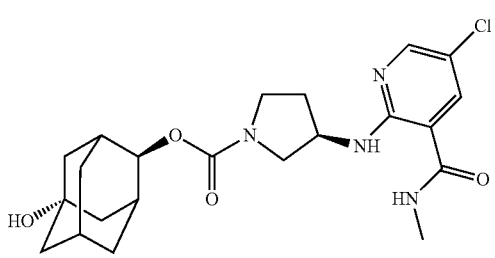 [SMILES: CNC(=O)c1cc(Cl)cnc1N[C@@H]1CCN(C(=O)O[C@H]2C3CC4CC2C[C@](O)(C4)C3)C1]

The title compound was prepared by the procedure of Example 80 using 2,5-dichloro-N-methylnicotinamide. LC-MS Method 1 $t_R$=1.53 min, m/z=449; $^1$H NMR (CD$_3$OD) 1.45 (m, 2H), 1.70-2.20 (12H), 2.27 (m, 1H), 2.83 (s, 3H), 3.35-3.80 (4H), 4.57 (m, 1H), 4.77 (s, 1H), 7.87 (s, 1H), 8.14 (s, 1H)

Example 99

(trans-1-hydroxy-4-adamantyl) 3-(5-(tert-butyl(methyl)carbamoyl)pyridin-2-ylamino)pyrrolidine-1-carboxylate

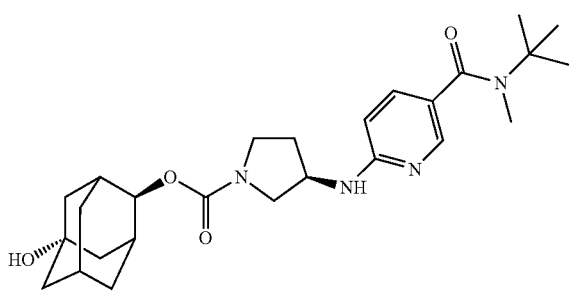 [SMILES: CN(C(=O)c1ccc(N[C@@H]2CCN(C(=O)O[C@H]3C4CC5CC3C[C@](O)(C5)C4)C2)nc1)C(C)(C)C]

The title compound was prepared by the procedure of Example 80 using N-tert-butyl-6-fluoro-N-methylnicotinamide. LC-MS Method 1 $t_R$=1.18 min, m/z=471; $^1$H NMR (CD$_3$OD) 1.40-1.60 (11H), 1.70-2.20 (12H), 2.38 (m, 1H), 2.97 (s, 3H), 3.40-3.90 (4H), 4.40 (m, 1H), 4.78 (s, 1H), 7.04 (m, 1H), 7.92 (d, 1H), 8.00 (s, 1H)

Example 100

(trans-1-hydroxy-4-adamantyl) 3-(3-(tert-butyl(methyl)carbamoyl)pyridin-2-ylamino)pyrrolidine-1-carboxylate

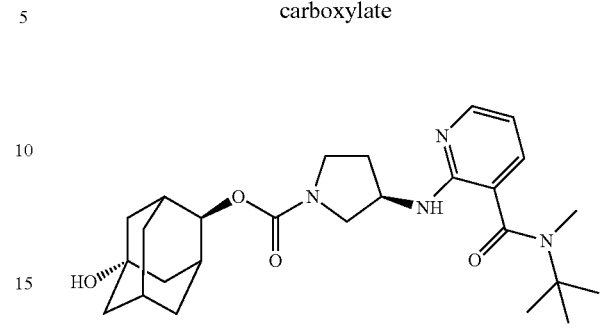

The title compound was prepared by the procedure of Example 80 using N-tert-butyl-2-fluoro-N-methylnicotinamide. LC-MS Method 1 $t_R$=1.33 min, m/z=471; $^1$H NMR (CD$_3$OD) 1.40-1.60 (11H), 1.7-2.4 (13H), 2.94 (s, 3H), 3.40-3.90 (4H), 4.45 (m, 1H), 4.78 (s, 1H), 6.98 (m, 1H), 7.97 (m, 1H), 8.02 (m, 1H)

Example 101

(R)-(trans-1-hydroxy-4-adamantyl) 3-(5-chloro-3-(cyclopropylcarbamoyl)pyridin-2-ylamino)pyrrolidine-1-carboxylate

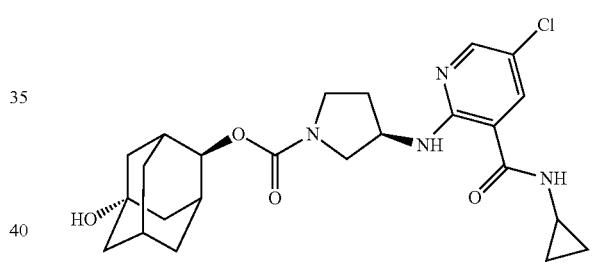

The title compound was prepared by the procedure of Example 80 using 2,5-dichloro-N-cyclopropylnicotinamide. LC-MS Method 1 $t_R$=1.65 min, m/z=475; $^1$H NMR (CD$_3$OD) 0.60 (m, 2H), 0.78 (m, 2H), 2.77 (m, 1H), 7.87 (m, 1H), 8.13 (m, 1H)

Example 102

(R)-(trans-1-hydroxy-4-adamantyl) 3-(3-(tert-butylcarbamoyl)-5-chloropyridin-2-ylamino)pyrrolidine-1-carboxylate

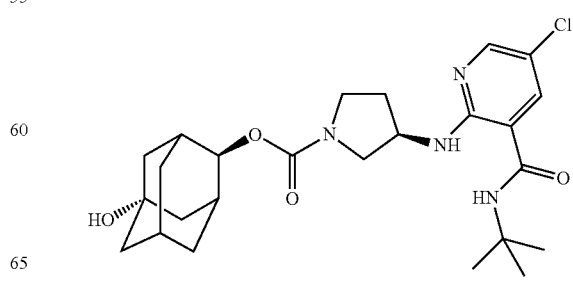

The title compound was prepared by the procedure of Example 80 using N-tert-butyl-2,5-dichloronicotinamide. LC-MS Method 1 $t_R$=1.88 min, m/z=493, 491; $^1$H NMR (CD$_3$OD) 1.41 (s, 9H), 1.46 (m, 2H), 1.70-2.20 (12H), 2.28 (m, 1H), 3.35-3.80 (4H), 4.54 (m, 1H), 4.76 (s, 1H), 7.85 (s, 1H), 8.10 (s, 1H).

Example 103

(R)-(trans-1-hydroxy-4-adamantyl) 3-(6-(cyclopropylcarbamoyl)benzo[d]thiazol-2-ylamino)pyrrolidine-1-carboxylate

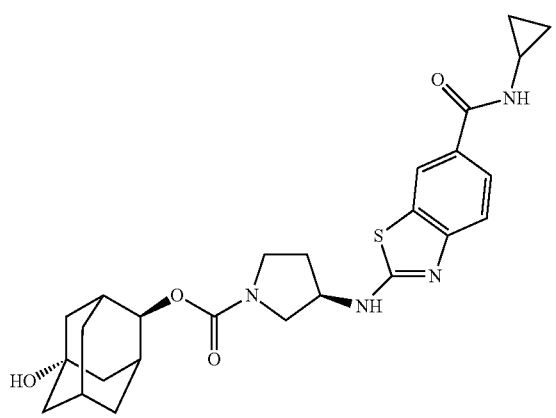 [SMILES: O=C(NC1CC1)c1ccc2nc(N[C@@H]3CCN(C(=O)O[C@H]4C5CC6CC4C[C@](O)(C6)C5)C3)sc2c1]

The title compound was prepared by the procedure of Example 80 using 2-chloro-N-cyclopropylbenzo[d]thiazole-6-carboxamide. LC-MS Method 1 $t_R$=1.32 min, m/z=497; $^1$H NMR (CD$_3$OD) 0.63 (m, 2H), 0.81 (m, 2H), 1.45 (m, 2H), 1.70-2.20 (12H), 2.35 (m, 1H), 2.84 (m, 1H), 3.50-3.85 (4H), 4.52 (br s, 1H), 4.78 (br s, 1H), 7.51 (d, 1H), 7.79 (d, 1H), 8.13 (s, 1H).

2-chloro-N-cyclopropylbenzo[d]thiazole-6-carboxamide was prepared by EDC coupling of 2-chlorobenzo[d]thiazole-6-carboxylic acid and cyclopropylamine.

Example 104

3-((R)-3-(5-cyanopyridin-2-ylamino)pyrrolidine-1-carboxamido)-8-azabicyclo[3.2.1]octane-8-carboxamide

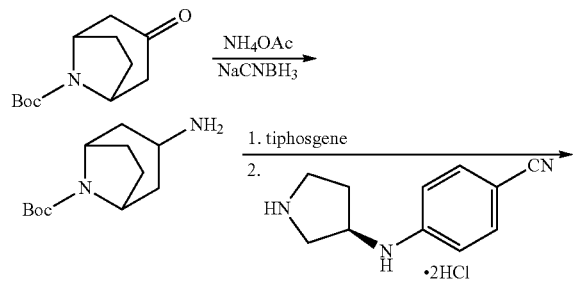

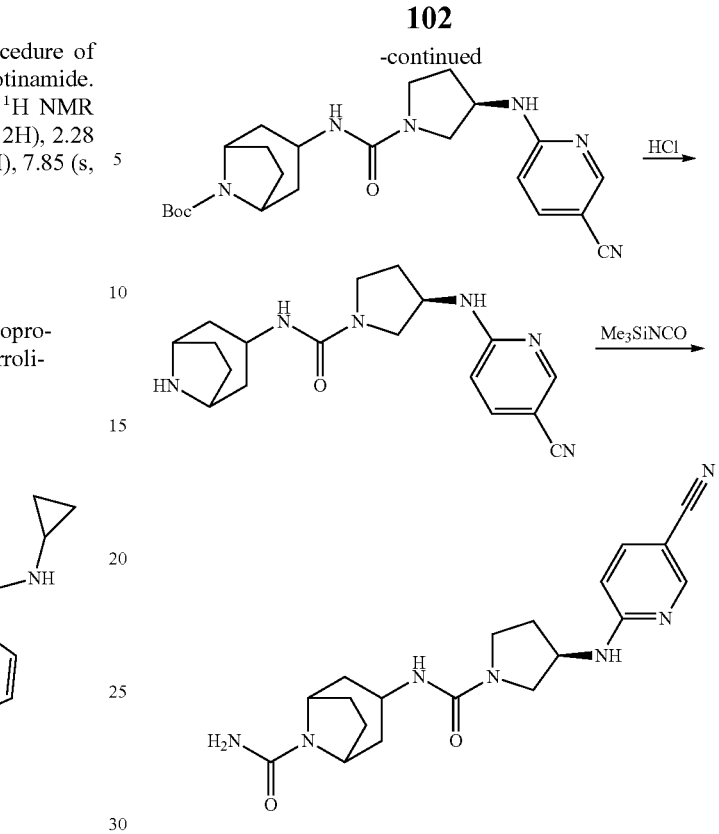

Step 1

A stirred mixture of Boc-nortropinone (287 mg, 1.3 mmol), NH$_4$OAc (1.96 g, 25.5 mmol), NaCNBH$_3$ (800 mg, 12.7 mmol) and MeOH (20 mL) was heated at reflux for 2 h. The mixture was concentrated, the residue was diluted with 0.5 M aq NaOH (30 mL) and extracted with CH$_2$Cl$_2$ (2×50 mL). The combined organic phase was washed with brine (20 mL), dried over Na$_2$SO$_4$ and concentrated to afford tert-butyl 3-amino-8-azabicyclo[3.2.1]octane-8-carboxylate (291 mg, quant) as a mixture of isomers. LC-MS Method 1 $t_R$=0.88 min, m/z=227.

Step 2

To a stirred, ice-cold mixture of tert-butyl 3-amino-8-azabicyclo[3.2.1]octane-8-carboxylate (149 mg, 0.66 mmol), CH$_2$Cl$_2$ (4 mL) and satd aq NaHCO$_3$ (2 mL) was added solid triphosgene (65 mg, 0.22 mmol). The mixture was stirred in the ice bath for 30 min and diluted with CH$_2$Cl$_2$ (6 mL) and brine (8 mL). The organic layer was separated and added to a stirred solution of (R)-4-(pyrrolidin-3-ylamino)benzonitrile dihydrochloride (165 mg, 0.66 mmol) in CH$_2$Cl$_2$ (2 mL) and dry pyridine (0.5 mL). The mixture was stirred overnight at rt, diluted with EtOAc (90 mL), washed with 5% aq HCl (20 mL), satd aq NaHCO$_3$ (20 mL) and brine (20 mL), and dried over Na$_2$SO$_4$. Removal of the solvent left an oil (246 mg) which was purified by prep HPLC to afford tert-butyl 3-((R)-3-(5-cyanopyridin-2-ylamino)pyrrolidine-1-carboxamido)-8-azabicyclo[3.2.1]octane-8-carboxylate (49 mg, 18%). LC-MS Method 1 $t_R$=1.52 min, m/z=441, 385.

Step 3 tert-butyl 3-((R)-3-(5-cyanopyridin-2-ylamino)pyrrolidine-1-carboxamido)-8-azabicyclo[3.2.1]octane-8-carboxylate (49 mg, 0.11 mmol) was dissolved in CH$_2$Cl$_2$ (2.5 mL) and 4 M HCl in dioxane (0.8 mL, 3.2 mmol) was added. The mixture was stirred at rt for 1 h and concentrated to give (3R)—N-(8-azabicyclo[3.2.1]octan-3-yl)-3-(5-cyanopyridin-2-ylamino)pyrrolidine-1-carboxamide dihydrochloride (46 mg, quant).

Step 4

To a stirred solution of (3R)—N-(8-azabicyclo[3.2.1]octan-3-yl)-3-(5-cyanopyridin-2-ylamino)pyrrolidine-1-carboxamide dihydrochloride salt (17.5 mg, 0.042 mmol) and i-Pr$_2$NEt (0.032 mL, 0.18 mmol) in CH$_2$Cl$_2$ (1 mL) was added Me$_3$SiNCO (0.008 mL, 0.06 mmol). The mixture was stirred at overnight and concentrated. The residue was purified by prep HPLC to give two isomeric products.

Isomer 1: LC-MS Method 1 t$_R$=0.95 min, m/z=384; $^1$H NMR (CD$_3$OD) [selected resonances] 2.25 (m, 1H), 3.45 (m, 2H), 3.66 (m, 1H), 4.20-4.30 (3H), 4.48 (m, 1H), 6.71 (d, 1H), 7.68 (dd, 1H), 7.38 (d, 1H).

Isomer 2: LC-MS Method 1 t$_R$=1 min, m/z=384; $^1$H NMR (CD$_3$OD) [selected resonances] 2.17 (m, 2H), 2.26 (m, 1H), 3.35 (m, 1H), 3.50 (m, 2H), 3.71 (m, 1H), 3.84 (m, 1H), 4.22 (br s, 2H), 4.51 (m, 1H), 6.68 (d, 1H), 7.67 (dd, 1H), 8.37 (d, 1H).

Example 105

(3R)-8-carbamoyl-8-azabicyclo[3.2.1]octan-3-yl 3-(5-cyanopyridin-2-ylamino)pyrrolidine-1-carboxylate

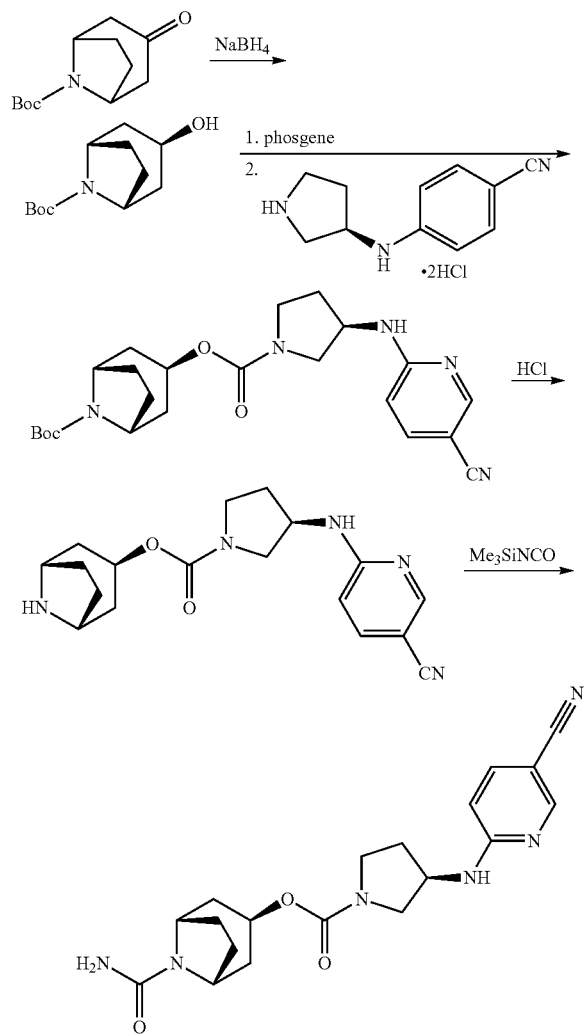

Step 1

A stirred solution of Boc-nortropinone (930 mg, 4.1 mmol) in MeOH (40 mL) was cooled in an ice bath and a NaBH$_4$ caplet (1 g, 26.7 mmol) was added. The ice bath was allowed to melt and stirring was continued overnight at rt. The mixture was concentrated to leave a white solid which was partitioned between EtOAc (100 mL), brine (10 mL) and water (10 mL). The organic layer was separated, dried over Na$_2$SO$_4$ and concentrated to leave an oil (966 mg). Chromatography on a 40-g silica gel cartridge eluted with a 0-100% EtOAc in hexanes gradient afforded two isomeric alcohols. The less polar alcohol, (1R,3r,5S)-tert-butyl 3-hydroxy-8-azabicyclo[3.2.1]octane-8-carboxylate, was isolated (462 mg, 45%).

Step 2

A stirred solution of (1R,3r,5S)-tert-butyl 3-hydroxy-8-azabicyclo[3.2.1]octane-8-carboxylate (126 mg, 0.55 mmol) in CH$_2$Cl$_2$ (3 mL) was cooled in an ice bath and 20% COCl$_2$ in PhMe (0.31 mL, 0.58 mmol) was added, followed by i-Pr$_2$NEt (0.11 mL, 0.61 mmol). The mixture was allowed to warm to rt and stirred overnight. Solid (R)-4-(pyrrolidin-3-ylamino)benzonitrile dihydrochloride (144 mg, 0.55 mmol) and i-Pr$_2$NEt (0.5 mL) were added. The mixture was stirred at rt for 1 day, diluted with EtOAc (90 mL), washed with 5% aq HCl (20 mL), satd aq NaHCO$_3$ (20 mL) and brine (20 mL), and dried over Na$_2$SO$_4$. Removal of the solvent left an oil (164 mg) which was purified by chromatography on a 12-g silica gel cartridge eluted with a 0-100% EtOAc in hexanes gradient to afford (1R,3r,5S)-tert-butyl 3-((R)-3-(5-cyanopyridin-2-ylamino)pyrrolidine-1-carbonyloxy)-8-azabicyclo[3.2.1]octane-8-carboxylate (64 mg, 26%). LC-MS Method 1 t$_R$=1.75 min, m/z=442, 386.

Step 3

A procedure analogous to Example 104 Step 3 was employed.

Step 4

The title compound was prepared employing a procedure analogous to Example 104 Step 4. LC-MS Method 1 t$_R$=1.15 min, m/z=385; $^1$H NMR (CD$_3$OD) [selected resonances] 4.22 (m, 2H), 4.50 (m, 1H), 6.65 (dd, 1H), 7.66 (dd, 1H), 8.35 (d, 1H)

Example 106

(3R)-3-(5-cyanopyridin-2-ylamino)-N-(8-(methylsulfonyl)-8-azabicyclo[3.2.1]octan-3-yl)pyrrolidine-1-carboxamide

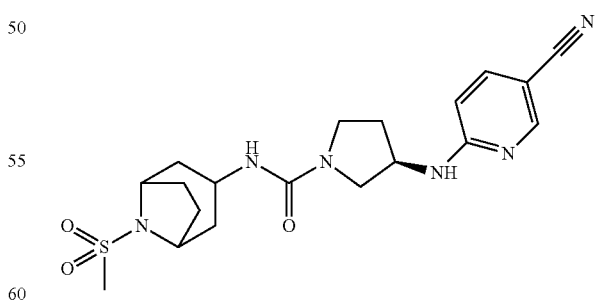

To a stirred solution of (3R)—N-(8-azabicyclo[3.2.1]octan-3-yl)-3-(5-cyanopyridin-2-ylamino)pyrrolidine-1-carboxamide (18 mg, 0.053 mmol) and i-Pr$_2$NEt (0.075 mL, 0.4 mmol) in CH$_2$Cl$_2$ (1 mL) was added methanesulfonyl chloride (0.008 mL, 0.10 mmol). The mixture was stirred overnight at rt, diluted with HOAc (0.1 mL) and MeOH (0.9 mL)

and purified by prep HPLC to afford the title compound (13 mg, 58%). LC-MS Method 1 $t_R$=1.1 min, m/z=419; $^1$H NMR (CD$_3$OD) [selected resonances] 2.93 (s, 3H), 4.47 (m, 1H), 6.78 (d, 1H), 7.77 (d, 1H), 8.40 (s, 1H)

Example 107

Methyl 2-((R)-1-((trans-1-hydroxy-4-adamantyloxy) carbonyl)pyrrolidin-3-ylamino)pyrimidine-5-carboxylate

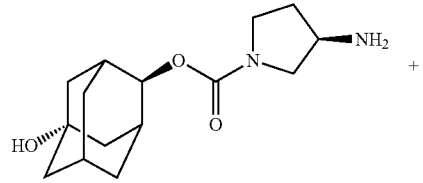

+

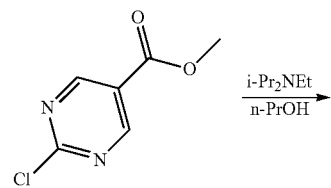

i-Pr$_2$NEt / n-PrOH →

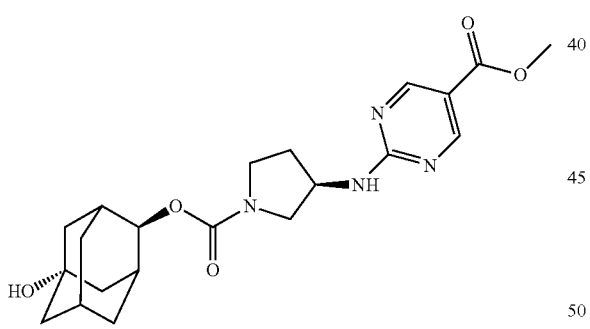

A solution of (R)-(trans-1-hydroxy-4-adamantyl) 3-aminopyrrolidine-1-carboxylate (159 mg, 0.57 mmol), methyl 2-chloropyrimidine-5-carboxylate (115 mg, 0.67 mmol), i-Pr2NEt (0.2 mL, 1.13 mmol) and n-PrOH (4 mL) was stirred at rt for 2 days. The mixture was concentrated and the residue was chromatographed on a 12-g silica cartridge eluted with a 0-100% EtOAc in hexanes gradient to afford the title compound (124 mg, 52%) as a white solid. LC-MS Method 1 $t_R$=1.37 min, m/z=417; $^1$H NMR (CDCl$_3$) 1.42 (m, 2H), 1.65-2.40 (13H), 3.39 (m, 1H), 3.58 (m, 2H), 3.83 (m, 1H), 3.88 (s, 3H), 4.64 (m, 1H), 4.83 (s, 1H), 5.90 (1H), 8.83 (br s, 2H)

Example 108

2-((R)-1-((trans-1-hydroxy-4-adamantyloxy)carbonyl)pyrrolidin-3-ylamino)pyrimidine-5-carboxylic acid

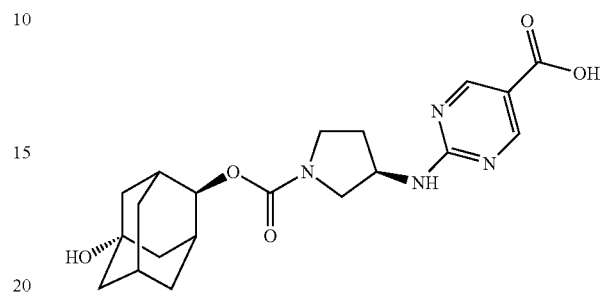

To a stirred solution of methyl 2-((R)-1-((trans-1-hydroxy-4-adamantyloxy)carbonyl)pyrrolidin-3-ylamino)pyrimidine-5-carboxylate (124 mg, 0.3 mmol) in THF (2 mL), MeOH (4 mL) and water (2 mL) was added LiOH.H$_2$O (25 mg, 0.6 mmol). The mixture was stirred overnight at rt and purified by prep HPLC to afford the title compound (81 mg, 68%) as a white solid. LC-MS Method 1 $t_R$=1.15 min, m/z=403; $^1$H NMR (CD$_3$OD) 1.43 (m, 2H), 1.70-2.20 (12H), 2.26 (m, 1H), 3.30-3.80 (4H), 4.57 (m, 1H), 4.78 (s, 1H), 8.80 (br s, 2H).

Example 109

(R)-(trans-1-hydroxy-4-adamantyl) 3-(5-carbamoylpyrimidin-2-ylamino)pyrrolidine-1-carboxylate

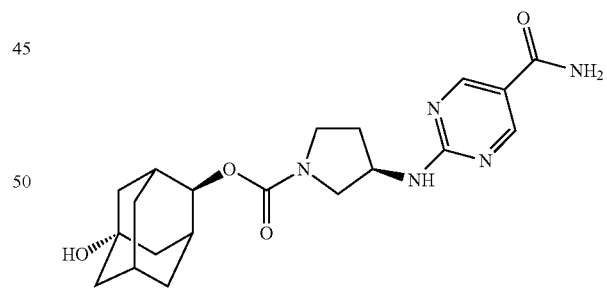

To a stirred solution of 2-((R)-1-((trans-1-hydroxy-4-adamantyloxy)carbonyl)pyrrolidin-3-ylamino)pyrimidine-5-carboxylic acid 9.0 mg, 0.022 mmol) and i-Pr2NEt (0.04 mL, 0.22 mmol) in CH$_2$Cl$_2$ (1 mL) was added 0.5 M NH3 in dioxane (0.22 mL, 0.11 mmol) followed by solid HATU (45 mg, 0.11 mmol). The mixture was stirred at rt overnight and evaporated to dryness. The residue was purified by prep HPLC to afford the title compound (5.3 mg, 59%). LC-MS Method 1 $t_R$=1.07 min, m/z=402; $^1$H NMR (CD$_3$OD) 1.44 (m, 2H), 1.70-2.20 (12H), 2.26 (m, 1H), 3.35-3.85 (4H), 4.57 (m, 1H), 4.77 (s, 1H), 8.79 (br s, 2H).

Example 110

(R)-(trans-1-hydroxy-4-adamantyl) 3-(5-(methylcarbamoyl)pyrimidin-2-ylamino)pyrrolidine-1-carboxylate

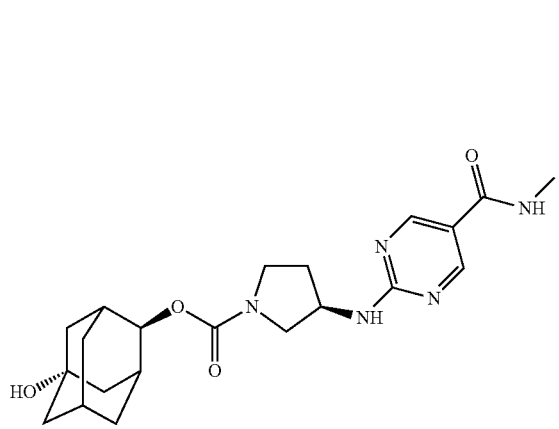 [SMILES: CNC(=O)c1cnc(N[C@@H]2CCN(C(=O)O[C@H]3C4CC5CC3C[C@](O)(C5)C4)C2)nc1]

The title compound was prepared following the procedure of Example 109 using MeNH₂. LC-MS Method 1 $t_R$=1.1 min, m/z=416; ¹H NMR (CD₃OD) 1.44 (m, 2H), 1.70-2.20 (12H), 2.26 (m, 1H), 2.88 (s, 3H), 3.35-3.80 (4H), 4.57 (m, 1H), 4.77 (s, 1H), 8.72 (br s, 2H).

Example 111

(R)-(trans-1-hydroxy-4-adamantyl) 3-(5-(dimethylcarbamoyl)pyrimidin-2-ylamino)pyrrolidine-1-carboxylate

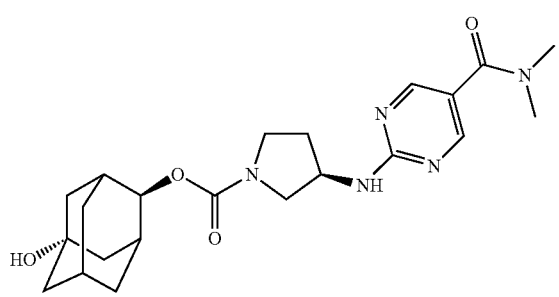 [SMILES: CN(C)C(=O)c1cnc(N[C@@H]2CCN(C(=O)O[C@H]3C4CC5CC3C[C@](O)(C5)C4)C2)nc1]

The title compound was prepared following the procedure of Example 109 using Me₂NH. LC-MS Method 1 $t_R$=1.15 min, m/z=430; ¹H NMR (CD₃OD) 1.47 (m, 2H), 1.70-2.20 (12H), 2.28 (m, 1H), 3.10 (br s, 6H), 3.40-3.90 (4H), 4.60 (m, 1H), 4.78 (s, 1H), 8.60 (br s, 2H).

Example 112

(R)-(trans-1-hydroxy-4-adamantyl) 3-(5-(cyclopropylcarbamoyl)pyrimidin-2-ylamino)pyrrolidine-1-carboxylate

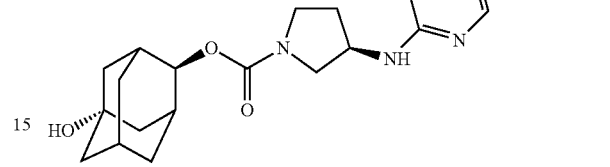

The title compound was prepared following the procedure of Example 109 using cyclopropylamine. LC-MS Method 1 $t_R$=1.2 min, m/z=442; ¹H NMR (CD₃OD) 0.61 (m, 2H), 0.79 (m, 2H), 1.46 (m, 2H), 1.70-2.20 (12H), 2.29 (m, 1H), 2.82 (m, 1H), 3.35-3.85 (4H), 4.58 (m, 1H), 4.77 (s, 1H), 8.78 (br s, 2H).

Example 113

(trans-1-carbamoyl-4-adamantyl) 3-(tert-butoxycarbonylamino)-3-(trifluoromethyl)pyrrolidine-1-carboxylate

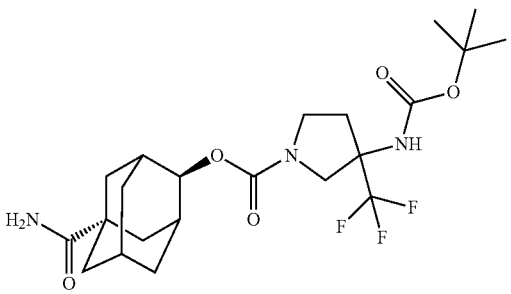 [SMILES: CC(C)(C)OC(=O)NC1(C(F)(F)F)CCN(C(=O)O[C@H]2C3CC4CC2C[C@](C(N)=O)(C4)C3)C1]

The title compound was prepared from tert-butyl 3-(trifluoromethyl)pyrrolidin-3-ylcarbamate analogous to those in Examples 14 and 16. LC-MS Method 1 $t_R$=1.63 min, m/z=476; ¹H NMR (CD₃OD) [selected resonances] 1.42 (s, 9H), 1.58 (m, 2H), 4.78 (s, 1H)

Example 114

(R)-(1-(methylcarbamoyl)-4-adamantyl) 3-(5-cyanopyridin-2-ylamino)pyrrolidine-1-carboxylate

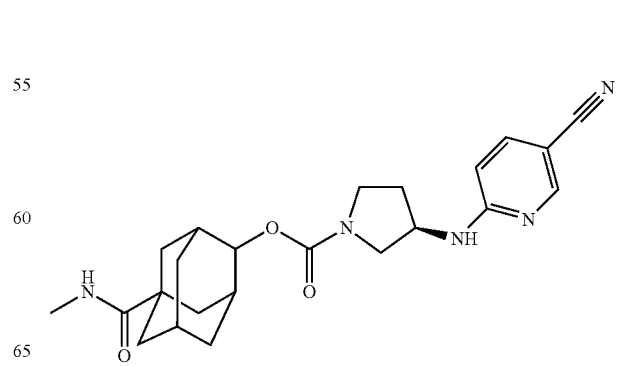

The title compound was prepared from (R)-4-(3-(tert-butoxycarbonylamino)pyrrolidine-1-carbonyloxy)adamantane-1-carboxylic acid and methylamine using the procedure of Example 109. Two isomers were isolated.

Isomer 1: (R)-(cis-1-(methylcarbamoyl)-4-adamantyl) 3-(5-cyanopyridin-2-ylamino)pyrrolidine-1-carboxylate. LC-MS Method 1 $t_R$=1.32 min, m/z=424; $^1$H NMR (CD$_3$OD) 1.60-2.20 (14H), 2.28 (m, 1H), 2.68 (3H), 3.35-3.80 (4H), 4.47 (m, 1H), 4.77 (s, 1H), 6.77 (d, 1H), 7.75 (d, 1H), 8.40 (s, 1H).

Isomer 2: (R)-(trans-1-(methylcarbamoyl)-4-adamantyl) 3-(5-cyanopyridin-2-ylamino)pyrrolidine-1-carboxylate. LC-MS Method 1 $t_R$=1.36 min, m/z=424; $^1$H NMR (CD$_3$OD) 1.56 (m, 2H), 1.80-2.20 (12H), 2.29 (m, 1H), 2.68 (s, 3H), 3.35-3.80 (4H), 4.58 (m, 1H), 4.79 (s, 1H), 6.74 (m, 1H), 7.72 (m, 1H), 8.38 (s, 1H).

Example 115

(R)-(1-hydroxy-4-adamantyl) 3-(5-fluoropyridin-2-ylamino)pyrrolidine-1-carboxylate

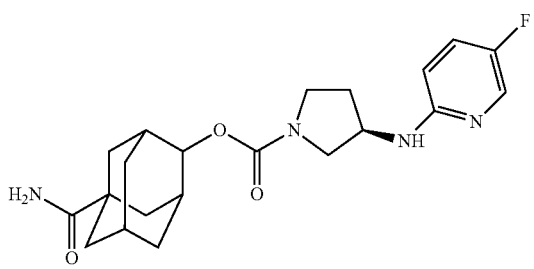 [SMILES: NC(=O)C12CC3CC(C1)C(OC(=O)N1CC[C@@H](Nc4ccc(F)cn4)C1)C(C3)C2]

The title compound was prepared from (R)-5-fluoro-N-(pyrrolidin-3-yl)pyridin-2-amine following procedures analogous to those in Examples 14 and 16 and was isolated as a mixture of cis and trans isomers. LC-MS Method 1 $t_R$=1.03, 1.15 min, m/z=403; $^1$H NMR (CD$_3$OD) [selected resonances] 6.98 (m, 1H), 7.82 (m, 1H), 7.96 (m, 1H)

Example 116

(R)-(trans-1-carbamoyl-4-adamantyl) 3-(6-cyanopyridazin-3-ylamino)pyrrolidine-1-carboxylate

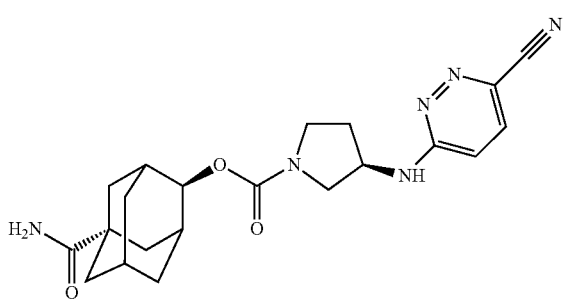 [SMILES: N#Cc1ccc(N[C@@H]2CCN(C(=O)O[C@H]3C4CC5CC3C[C@](C(N)=O)(C5)C4)C2)nn1]

The title compound was prepared from 6-chloropyridazine-3-carbonitrile following a procedure analogous to Example 33 Step 2. LC-MS Method 1 $t_R$=1.22 min, m/z=411; $^1$H NMR (CD$_3$OD) [selected resonances] 1.39 (m, 2H), 4.65 (m, 1H), 4.80 (s, 1H), 6.97 (d, 1H), 7.62 (d, 1H).

Example 117

(R)-(1-(cyclohexylcarbamoyl)-4-adamantyl) 3-(5-cyanopyridin-2-ylamino)pyrrolidine-1-carboxylate

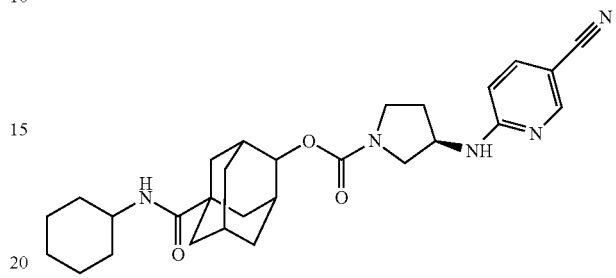

The title compound was prepared from (R)-4-(3-(tert-butoxycarbonylamino)pyrrolidine-1-carbonyloxy)adamantane-1-carboxylic acid and cyclohexylamine using the procedure of Example 109. Two isomers were isolated.

Isomer 1: (R)-(cis-1-(cyclohexylcarbamoyl)-4-adamantyl) 3-(5-cyanopyridin-2-ylamino)pyrrolidine-1-carboxylate. LC-MS Method 1 $t_R$=1.75 min, m/z=492.

Isomer 2: (R)-(trans-1-(cyclohexylcarbamoyl)-4-adamantyl) 3-(5-cyanopyridin-2-ylamino)pyrrolidine-1-carboxylate. LC-MS Method 1 $t_R$=1.80 min, m/z=492.

Example 118

(R)-(1-(cyclopropylcarbamoyl)-4-adamantyl) 3-(5-cyanopyridin-2-ylamino)pyrrolidine-1-carboxylate

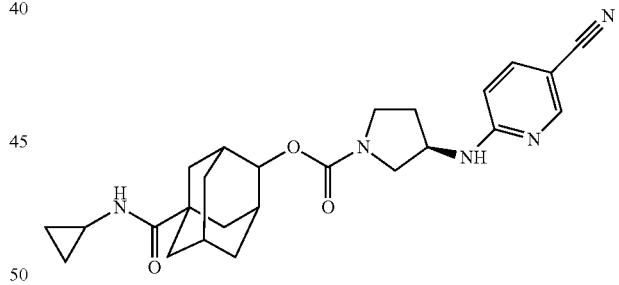

The title compound was prepared from (R)-4-(3-(tert-butoxycarbonylamino)pyrrolidine-1-carbonyloxy)adamantane-1-carboxylic acid and cyclopropylamine using the procedure of Example 109. Two isomers were isolated.

Isomer 1: (R)-(cis-1-(cyclopropylcarbamoyl)-4-adamantyl) 3-(5-cyanopyridin-2-ylamino)pyrrolidine-1-carboxylate. LC-MS Method 1 $t_R$=1.43 min, m/z=450.

Isomer 2: (R)-(trans-1-(cyclopropylcarbamoyl)-4-adamantyl) 3-(5-cyanopyridin-2-ylamino)pyrrolidine-1-carboxylate. LC-MS Method 1 $t_R$=1.50 min, m/z=450.

Biological Test Example 1

The inhibition of purified 11β-HSD1 by compounds of Formula I is measured using a Scintillation Proximity Assay. All reactions are carried out at room temperature in 96 well flexible Microbeta reaction plates. First, 1 μL of a 0.1 mM solution of a compound of Formula I is mixed in DMSO diluted in half-log increments (8 points) starting at 1 μM final concentration. To this dot is added 50 μL of substrate solution (50 mM HEPES, pH 7.4, 100 mM KCl, 5 mM NaCl, 2 mM MgCl$_2$ containing 20 μM $^3$H cortisone, 1 mM NADPH). After a 10 minute incubation, 50 μL of enzyme solution containing 20 nM recombinant 11β-HSD1 (expressed in E. coli, and affinity purified) is added. The reaction is then incubated for 90 minutes, and stopped by adding 50 pP of SPA bead mix (18-β-glycyrrhetinic acid, 10 μM final, 5 mg/ml protein A coated YSi SPA beads, and 1 ug/ml α-cortisol antibody (East Coast Biologics)). The plate is shaken for 120 minutes, and the radioactivity corresponding to $^3$H cortisol is measured on a Wallac Microbeta.

Biological Test Example 2

The inhibition of a microsomal preparation of 11β-HSD1 by compounds of the invention is measured essentially as previously described (K. Solly, et al., High-Throughput Screening of 11-Beta-Hydroxysteroid Dehydrogenase Type 1 in Scintillation Proximity Assay Format, Assay Drug Dev Technol 3 (2005) 377-384). All reactions are carried out at room temperature in 96 well clear flexible PET Microbeta plates (PerkinElmer). First, 49 μl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) is mixed in 1 μL of a test compound in DMSO diluted in half-log increments (8 points) starting at 0.1 mM. After a 10 minute pre-incubation, 50 μL of enzyme solution containing microsomes isolated from CHO cells overexpressing human 11β-HSD1 (10-20 μg/ml of total protein) is added, and the plates are then incubated for 90 minutes at room temperature. The reaction is stopped by adding 50 μl of the SPA beads suspension containing 10 μM 18β-glycyrrhetinic acid, 5 mg/ml protein A coated YSi SPA beads (GE Healthcare) and 3.3 μg/ml of anti-cortisol antibody (East Coast Biologics) in Superblock buffer (Bio-Rad). The plates are then shaken for 120 minutes at room temperature, and the SPA signal corresponding to [$^3$H]cortisol is measured on a Microbeta plate reader.

Biological Test Example 3

The inhibition of 11β-HSD1 by compounds of this invention is measured in whole cells as follows. Cells for the assay can be obtained from two sources: fully differentiated human omental adipocytes from Zen-Bio, Inc.; and human omental pre-adipocytes from Lonza Group Ltd. Pre-differentiated omental adipocytes from Zen-Bio Inc. are purchased in 96-well plates and used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-γ agonist). The cells are maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% $CO_2$.

Pre-adipocytes (purchased from Lonza Group Ltd.) are placed in culture in Preadipocyte Growth Medium-2 supplemented with fetal bovine serum, penicillin, and streptomycin (supplied by Lonza) at 37° C., 5% $CO_2$. Pre-adipocytes are differentiated by the addition of insulin, dexamethasone, indomethacin and isobutyl-methylxanthine (supplied by Lonza) to the Preadipocyte Growth Medium-2. Cells are then exposed to the differentiating factors for 7 days, at which point the cells are differentiated and ready for the assay. One day before running the assay, the differentiated omental adipocytes are transferred into serum- and phenol-red-free medium for overnight incubation. The assay is performed in a total volume of 200 μL. The cells are pre-incubated with serum-free, phenol-red-free medium containing 0.1% (v/v) of DMSO and various concentrations of the test compounds at least 1 h before [$^3$H] cortisone in ethanol (50 Ci/mmol, ARC, Inc.) is added to achieve a final concentration of cortisone of 100 nM. The cells are then incubated for 3-4 hrs at 37° C., 5% $CO_2$. Negative controls are incubated without radioactive substrate and receive the same amount of [$^3$H] cortisone at the end of the incubation. Formation of [$^3$H] cortisol is monitored by analyzing 25 μL of each supernatant in a scintillation proximity assay (SPA). (Solly, K., et al., Assay Drug Dev. Technol. 2005, 3, 377-384).

The inhibition of 11β-HSD1 by compounds of Formulae I, Ia, Ib, Ic, Id, Ie, If, Ig, Ih, or Ii, in whole cells is measured as follows. Omental adipocytes cultured in 96-well plates (purchased from Zen-Bio, Inc.) are used at least two weeks after differentiation from precursor preadipocytes started in medium supplemented with adipogenic and lipogenic hormones (human insulin, dexamethasone, isobutylmethylxanthine and PPARγ agonist). The cells are maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% $CO_2$ and then transferred into serum-free, phenol red free medium for overnight incubation. The assay is performed in a total volume of 200 μL. The cells are pre-incubated with serum-free, phenol red free medium containing 0.1% (v/v) of DMSO and various concentrations of compounds of Formulae I, Ia, Ib, Ic, Id, Ie, If, Ig, Ih, or Ii, for at least 1 h before [$^3$H] cortisone in ethanol (50 Ci/mmol, ARC, Inc.) is added to achieve final concentration of cortisone of 100 nM. The cells are then incubated for 3-4 h at 37° C., 5% $CO_2$. Negative controls are incubated without radioactive substrate and receive the same amount of [$^3$H] cortisone at the end of the incubation. Formation of [$^3$H] cortisol is monitored by analyzing 25 μL of each supernatant in scintillation proximity assay (SPA). (Solly, K.; et al., Assay Drug Dev. Technol. 2005, 3, 377-384).

| Compound | Biological Test Example 1 IC$_{50}$ Range$^a$ | Biological Test Example 2 | | |
|---|---|---|---|---|
| | | IC$_{50}$ Range$^a$ | Average % inhibition at 100 nm | Average % inhibition at 111 nm |
| Example 1 | ++ | | | |
| Example 2 | ++ | ++ | | 95.2 |
| Example 3 | | ++ | | |
| Example 4 | | ++ | | |

-continued

| Compound | Biological Test Example 1 IC$_{50}$ Range$^a$ | Biological Test Example 2 | | |
|---|---|---|---|---|
| | | IC$_{50}$ Range$^a$ | Average % inhibition at 100 nm | Average % inhibition at 111 nm |
| Example 5 | | ++ | | |
| Example 6 | | ++ | | |
| Example 7 | | ++ | | |
| Example 8 | ++ | | | |
| Example 9 | ++ | | | |
| Example 9 Isomer 1 | | ++ | | 83.6 |
| Example 10 | ++ | | 90.9 | |
| Example 11 | ++ | | | |
| Example 12 | | ++ | | 58.8 |
| Example 13 | | ++ | 87.7 | |
| Example 14 | + | + | | |
| Example 15 Isomer 1 | + | ++ | | |
| Example 15 Isomer 2 | ++ | ++ | 88.6 | |
| Example 16 Isomer 1 | ++ | ++ | | 67.9 |
| Example 16 Isomer 2 | ++ | ++ | 93.6 | 95.1 |
| Example 17 Isomer 1 | | # | 22.1 | |
| Example 17 Isomer 2 | | ++ | 92.8 | |
| Example 18 Isomer 1 | | # | 22.6 | |
| Example 18 Isomer 2 | | ++ | 95.0 | |
| Example 19 | | ++ | 87.7 | |
| Example 20 Isomer 1 | | + | 46.6 | 45.2 |
| Example 20.2 | | ++ | 83.9 | 79.8 |
| Example 21 Isomer 1 | | # | 6.9 | |
| Example 21 Isomer 2 | | ++ | 89.0 | |
| Example 22 Isomer 1 | | # | 15.7 | |
| Example 22 Isomer 2 | | ++ | 95.5 | |
| Example 22 Isomer 2.1 | | ++ | 88.5 | |
| Example 22 Isomer 2.2 | | ++ | 82.7 | |
| Example 23 Isomer 1 | | # | 35.4 | |
| Example 23 Isomer 2 | | ++ | 94.4 | |
| Example 24 Isomer 1 | | # | 2.0 | |
| Example 24 Isomer 2 | | ++ | 87.4 | |
| Example 25 Isomer 1 | | # | 45.6 | |
| Example 25 Isomer 2 | | ++ | 91.3 | |
| Example 26 Isomer 1 | | ++ | 78.3 | |
| Example 26 Isomer 2 | | ++ | 91.9 | |
| Example 27 Isomer 1 | | # | 27.7 | |
| Example 27 Isomer 2 | | ++ | 55.8 | |
| Example 28 | | ++ | 86.1 | |
| Example 29 Isomer 1 | | # | 41.2 | |
| Example 29 Isomer 2 | | ++ | 90.8 | |
| Example 29 Isomer 2.1 | | ++ | 96.9 | |
| Example 29 Isomer 2.2 | | ++ | 89.3 | |
| Example 30 Isomer 1 | | # | 15.9 | |
| Example 30 Isomer 2 | | ++ | 91.3 | |
| Example 31 Isomer 1 | | # | 35.9 | |
| Example 31 Isomer 2 | | ++ | 91.5 | |
| Example 32 | | ++ | 95.1 | |
| Example 33 | | ++ | 78.6 | |
| Example 34 | | ++ | 94.6 | |
| Example 34 | | ++ | 99.6 | |
| Example 35 | | ++ | 101.1 | |
| Example 36 | | ++ | 95.1 | |
| Example 37 | | ++ | 96.9 | |
| Example 38 | | ++ | 98.0 | |
| Example 39 | | ++ | 95.5 | |
| Example 40 | | ++ | 96.0 | |
| Example 41 | | ++ | 94.8 | |
| Example 42 | | ++ | 79.3 | |
| Example 43 | | ++ | 102.0 | |
| Example 44 | | ++ | 97.2 | |
| Example 45 | | ++ | 97.7 | |
| Example 46 | ++ | | | |
| Example 47 | + | | | |
| Example 48 | + | | | |
| Example 49 | | ++ | | 74.6 |
| Example 50 | | ++ | | 92.9 |
| Example 51 | ++ | | | |
| Example 52 | ++ | | | |
| Example 53 | + | | | |
| Example 54 | ++ | | | |
| Example 55 | ++ | | | |
| Example 56 | ++ | | | |
| Example 57 | ++ | | | |

-continued

|  | Biological Test Example 1 IC$_{50}$ Range$^a$ | Biological Test Example 2 | | |
|---|---|---|---|---|
| Compound |  | IC$_{50}$ Range$^a$ | Average % inhibition at 100 nm | Average % inhibition at 111 nm |
| Example 58 |  | ++ |  | 94.3 |
| Example 59 |  | + |  | 47.5 |
| Example 60 |  | ++ |  | 83.3 |
| Example 61 |  | ++ | 97.6 |  |
| Example 62 Isomer 1 |  | ++ | 40.8 |  |
| Example 62 Isomer 2 |  | ++ | 78.7 |  |
| Example 63 |  | ++ | 98.4 |  |
| Example 64 |  | ++ | 83.6 |  |
| Example 65 |  | ++ | 97.1 |  |
| Example 66 |  | ++ | 95.5 |  |
| Example 67 |  | ++ | 97.0 |  |
| Example 68 |  | ++ | 90.7 |  |
| Example 69 |  | ++ | 98.7 |  |
| Example 70 |  | ++ | 78.4 |  |
| Example 71 |  | ++ | 84.2 | 82.6 |
| Example 72 |  | ++ | 97.3 | 97.3 |
| Example 73 |  | ++ | 94.6 |  |
| Example 74 |  | ++ | 97.8 | 96.5 |
| Example 75 |  | ++ | 98.8 | 97.7 |
| Example 76 |  | ++ | 97.9 | 101.1 |
| Example 77 Isomer 1 |  | # | 45.6 |  |
| Example 77 Isomer 2 |  | ++ | 88.7 |  |
| Example 78 |  | ++ | 80.1 |  |
| Example 79 Isomer 1 |  | ++ | 4.2 |  |
| Example 79 Isomer 2 |  | ++ | 91.9 |  |
| Example 80 |  | ++ | 90.2 |  |
| Example 81 |  | ++ | 54.4 |  |
| Example 82 |  | ++ | 86.6 |  |
| Example 83 |  | ++ | 98.5 |  |
| Example 84 |  | ++ | 71.6 |  |
| Example 85 |  | ++ | 64.0 |  |
| Example 86 |  | ++ | 101.1 |  |
| Example 87 |  | ++ | 100.4 |  |
| Example 88 |  | ++ | 69.4 |  |
| Example 89 |  | # | 39.1 |  |
| Example 90 |  | ++ | 95.6 |  |
| Example 91 |  | ++ | 63.6 |  |
| Example 92 |  | ++ | 60.2 |  |
| Example 93 |  | ++ | 94.4 |  |
| Example 94 |  | ++ | 90.8 |  |
| Example 95 |  | ++ | 90.6 |  |
| Example 96 |  | ++ | 101.2 |  |
| Example 97 |  | ++ | 91.1 |  |
| Example 98 |  | ++ | 91.1 |  |
| Example 99 |  | # | 21.8 |  |
| Example 100 |  | ++ | 46.8 |  |
| Example 101 |  | ++ | 82.6 |  |
| Example 102 |  | ++ | 78.7 |  |
| Example 103 |  | ++ | 88.8 |  |
| Example 104 Isomer 1 |  | − |  | −6.2 |
| Example 104 Isomer 2 |  | − |  | −6.1 |
| Example 105 |  | # | 14.8 |  |
| Example 106 |  | # | 3.9 |  |
| Example 107 |  | ++ | 53.6 |  |
| Example 108 |  | # | 14.2 |  |
| Example 109 |  | ++ | 50.1 |  |
| Example 110 |  | # | 32.2 |  |
| Example 111 |  | # | 33.5 |  |
| Example 112 |  | # | 33.3 |  |
| Example 113 |  | ++ | 92.0 |  |
| Example 114 Isomer 1 |  | # | 11.8 |  |
| Example 114 Isomer 2 |  | ++ | 58.4 |  |
| Example 115 |  | ++ | 95.2 |  |
| Example 116 |  | ++ | 71.4 |  |
| Example 117 Isomer 1 |  | # | 17.85 |  |
| Example 117 Isomer 2 |  | ++ | 63.1 |  |
| Example 118 Isomer 1 |  | # | 9.1 |  |
| Example 118 Isomer 2 |  | # | 7.15 |  |

$^a$++ means IC$_{50}$ <100 nM, + means IC$_{50}$ = 100 nM to 1000 nM, # means >100 nM, − means >1000 nM.

Prophetic Examples
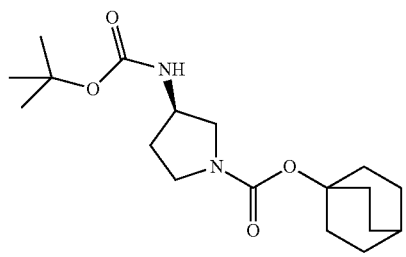
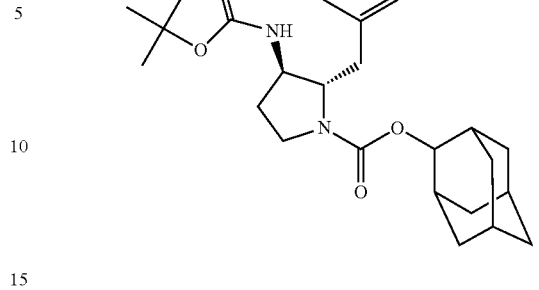
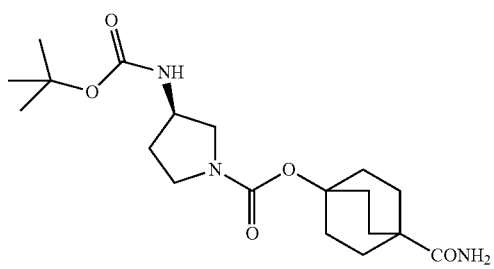
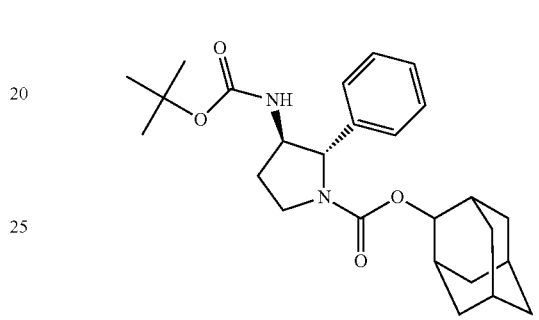
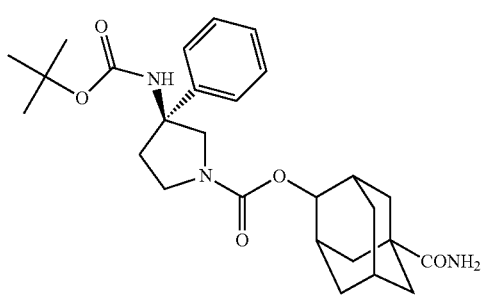
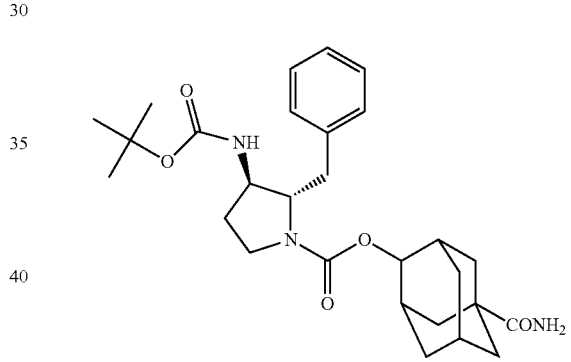
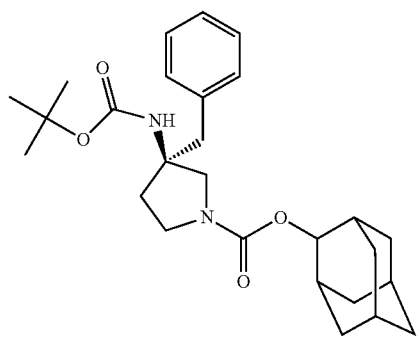
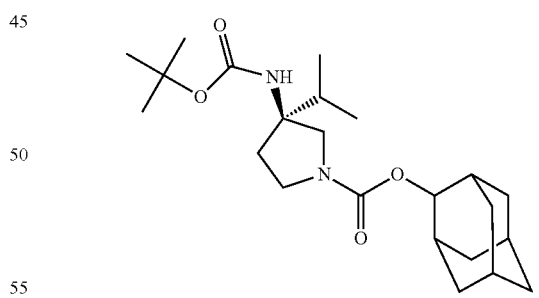
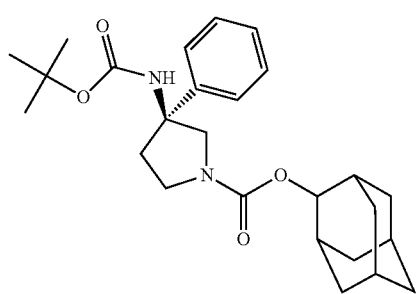
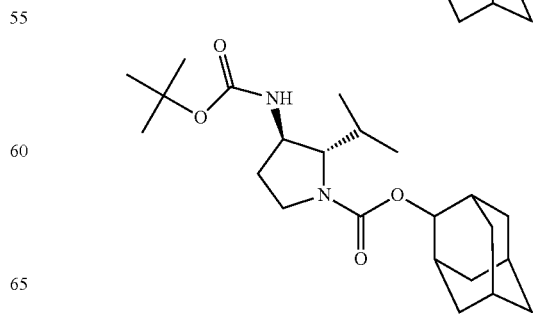

119
-continued
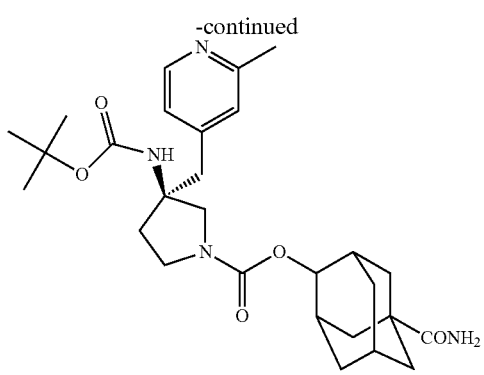
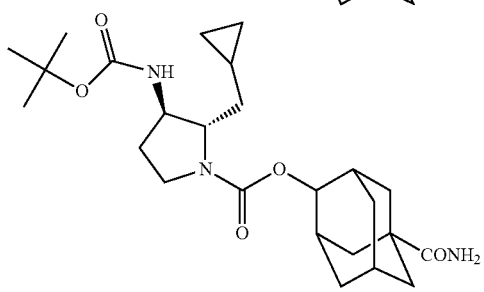
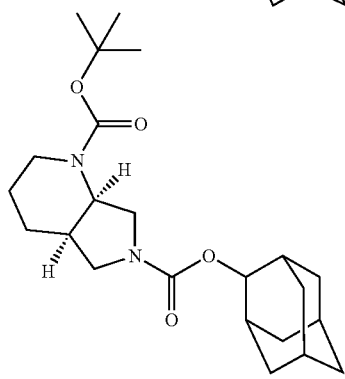
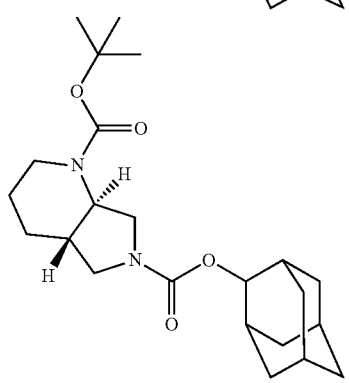
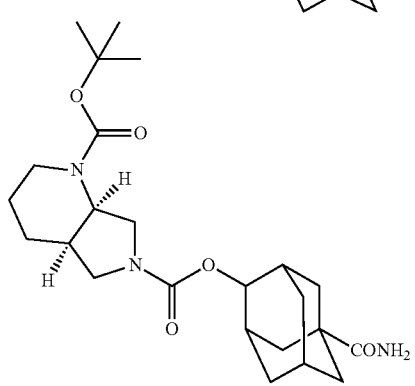
120
-continued
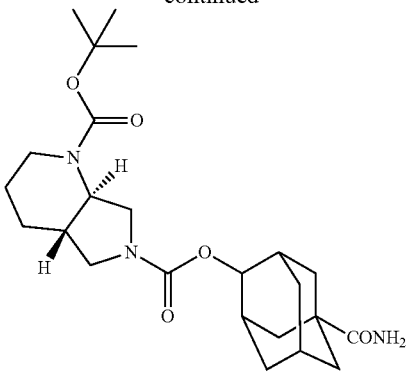
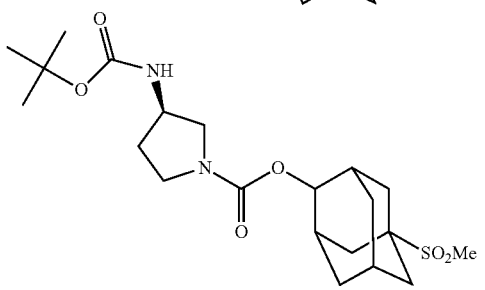
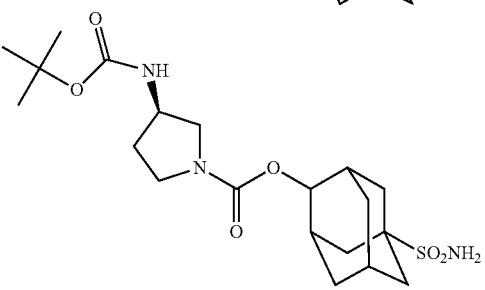
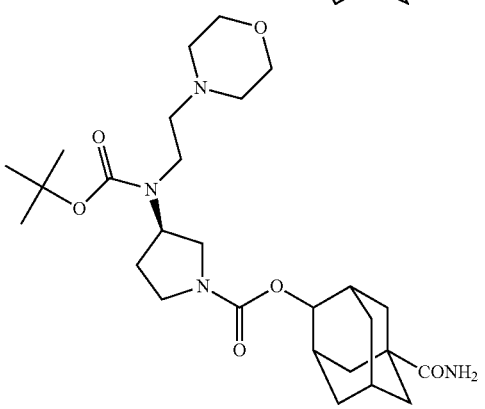
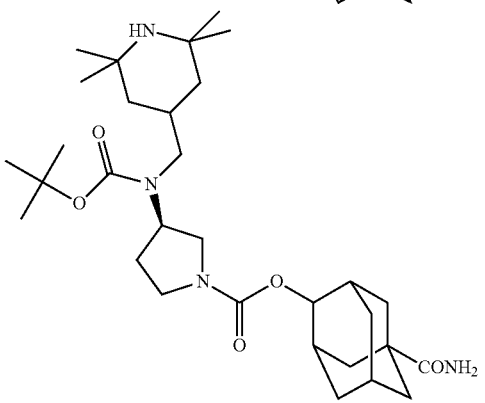

121
-continued
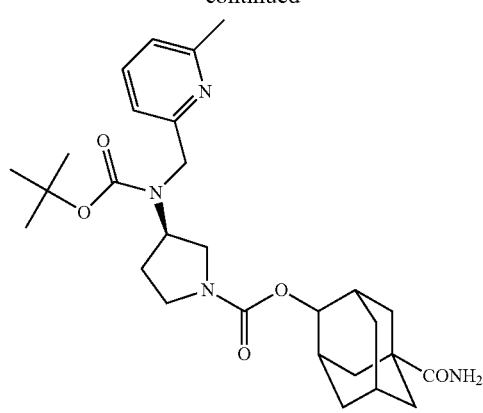
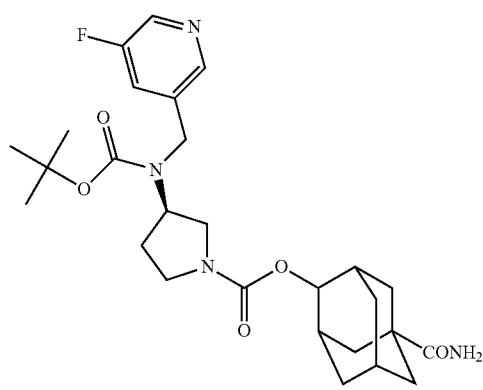
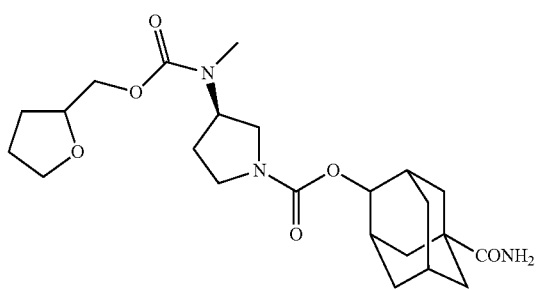
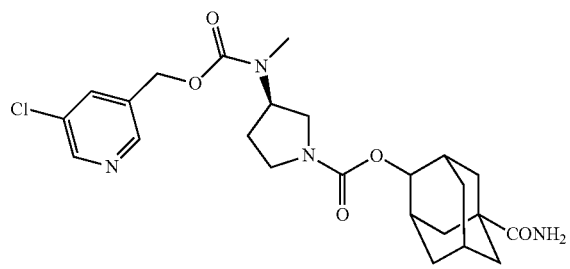
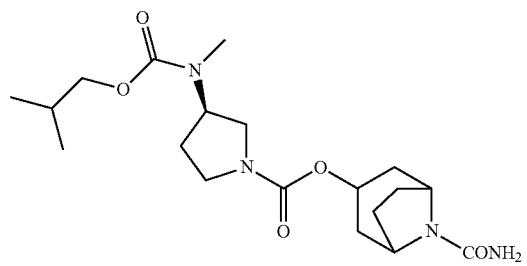
122
-continued
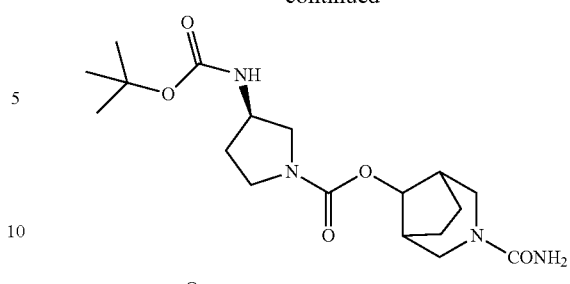
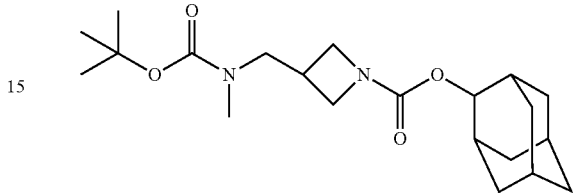
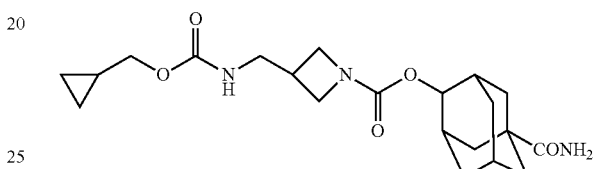
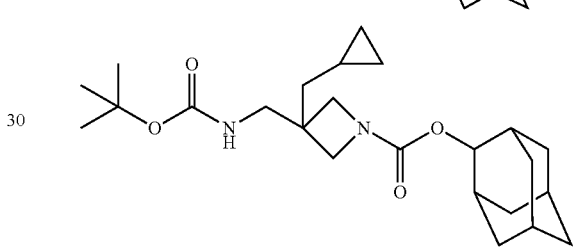
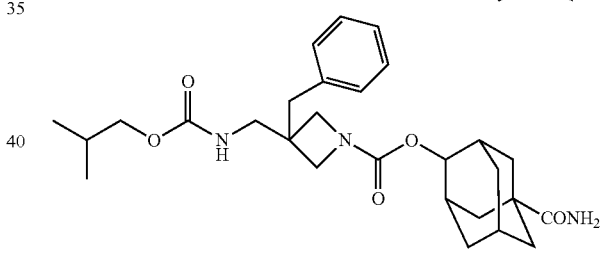
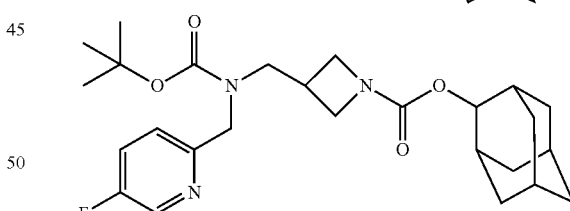
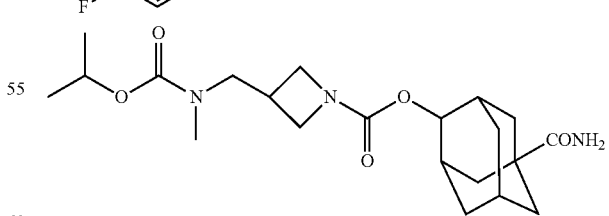
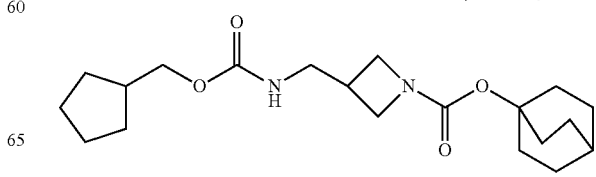

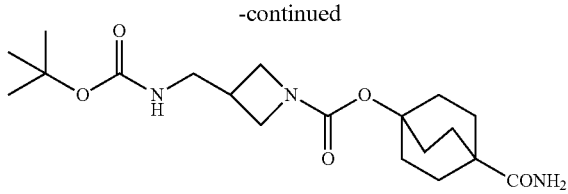

The compounds of the invention are useful for ameliorating or treating disorders or diseases in which decreasing the level of cortisol is effective in treating a disease state. Thus, the compounds of the invention can be used in the treatment or prevention of diabetes mellitus, obesity, symptoms of metabolic syndrome, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypretriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X.

The disclosed compounds can be used alone (i.e. as a monotherapy) or in combination with another therapeutic agent effective for treating any of the above indications. Alternatively, a pharmaceutical composition of the invention may comprise a compound of Formula I, II, III, IIIa, IIIb, IV, IVa, IVb, IVc, IVd, IVe, V, Va, Vb, VI, VIa, VIb, VII, VIIa, VIIb, VIII, VIIIa, VIIIb, IX, IXa, X, and Xa or a pharmaceutical salt thereof as the only pharmaceutically active agent in the pharmaceutical composition. The disclosed 11β-HSD1 inhibitors can be used alone or in a combination therapy with one or more additional agents for the treatment of diabetes, dyslipidemia, cardiovascular disease, hypertension, obesity, cancer or glaucoma.

A pharmaceutical composition of the invention may, alternatively or in addition to a compound of Formula I, II, III, IIIa, IIIb, IV, IVa, IVb, IVc, IVd, IVe, V, Va, Vb, VI, VIa, VIb, VII, VIIa, VIIb, VIII, VIIIa, VIIIb, IX, IXa, X, and Xa comprise a pharmaceutically acceptable salt of a compound of Formula I, II, III, IIIa, IIIb, IV, IVa, IVb, IVc, IVd, IVe, V, Va, Vb, VI, VIa, VIb, VII, VIIa, VIIb, VIII, VIIIa, VIIIb, IX, IXa, X, and Xa or a prodrug or pharmaceutically active metabolite of such a compound or salt and one or more pharmaceutically acceptable carriers therefore. Alternatively, a pharmaceutical composition of the invention may comprise a compound of Formula I, II, III, IIIa, IIIb, IV, IVa, IVb, IVc, IVd, IVe, V, Va, Vb, VI, VIa, VIb, VII, VIIa, VIIb, VIII, VIIIa, VIIIb, IX, IXa, X, and Xa or a pharmaceutical salt thereof as the only pharmaceutically active agent in the pharmaceutical composition.

The invention includes a therapeutic method for treating or ameliorating an 11β-HSD1 mediated disorder in a subject in need thereof comprising administering to a subject in need thereof an effective amount of a compound of Formula I, Ia or Ib, or an enantiomer, diastereomer, or pharmaceutically acceptable salt thereof of composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compound of Formula I, II, III, IIIa, IIIb, IV, IVa, IVb, IVc, IVd, IVe, V, Va, Vb, VI, VIa, VIb, VII, VIIa, VIIb, VIII, VIIIa, VIIIb, IX, IXa, X, and Xa or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors, such as Januvia™ (sitagliptin, Merck); PTB-1B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitor, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of Formula I, II, III, IIIa, IIIb, IV, IVa, IVb, IVc, IVd, IVe, V, Va, Vb, VI, VIa, VIb, VII, VIIa, VIIb, VIII, VIIIa, VIIIb, IX, IXa, X, and Xa or composition thereof in a combination therapy with one or more other 11β-HSD1 inhibitors (whether such inhibitors are also compounds of Formula I, II, III, IIIa, IIIb, IV, IVa, IVb, IVc, IVd, IVe, V, Va, Vb, VI, VIa, VIb, VII, VIIa, VIIb, VIII, VIIIa, VIIIb, IX, IXa, X, and Xa or are compounds of a different class/genus), or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

What is claimed is:

1. A compound of Formula (I):

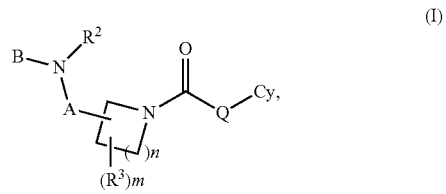

wherein

Cy is $(C_7\text{-}C_{12})$bicycloalkyl or $(C_9\text{-}C_{12})$tricycloalkyl, in which 1-2 carbon atoms are optionally replaced with heteroatoms independently selected from N and O, and which is optionally substituted with 1-3 groups independently selected from halogen, nitro, $(CH_2)_xCN$, $(C_1\text{-}C_3)$alkyl, halo$(C_1\text{-}C_3)$alkyl, hydroxy$(C_1\text{-}C_3)$alkyl, $(CH_2)_xOR^4$, halo$(C_1\text{-}C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$;

B is (a) —C(O)OR$^1$; or (b) aryl or heteroaryl, each optionally substituted with 1-4 groups represented by $R^6$;

$R^1$ is $(C_1\text{-}C_8)$alkyl, $(C_2\text{-}C_8)$alkenyl, $(C_2\text{-}C_8)$alkynyl, $(C_3\text{-}C_8)$cycloalkyl, heterocyclyl, $(C_3\text{-}C_8)$cycloalkyl$(C_1\text{-}C_3)$alkyl, heterocyclyl$(C_1\text{-}C_3)$alkyl, aryl, aryl$(C_1\text{-}C_3)$alkyl or heteroaryl$(C_1\text{-}C_3)$alkyl each optionally substituted by 1-4 groups independently selected from halogen, nitro, $(CH_2)_xCN$, $(C_1\text{-}C_3)$alkyl, halo$(C_1\text{-}C_3)$alkyl, hydroxy$(C_1\text{-}C_3)$alkyl, $(CH_2)_xOR^4$, halo$(C_1\text{-}C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, $(C_3-C_8)$cycloalkyl$(C_1-C_3)$alkyl, heterocyclyl$(C_1-C_3)$alkyl, alkyl portion of aryl $(C_1-C_3)$alkyl, heteroaryl and heteroaryl$(C_1-C_3)$alkyl are further optionally substituted with oxo;

$R^2$ and $R^3$ are independently (a) hydrogen; or (b) $(C_1-C_8)$alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl, heteroaryl and heteroaryl$(C_1-C_3)$alkyl are further optionally substituted with oxo;

each $R^4$ is independently (a) hydrogen; or (b) $(C_1-C_{10})$alkyl, $(C_3-C_8)$cycloalkyl, aryl or aryl$(C_1-C_3)$alkyl, each optionally substituted with halogen, $(C_1-C_3)$alkoxy, $(C_1-C_3)$alkyl, halo$(C_1-C_3)$alkyl, halo$(C_1-C_3)$alkoxy, cyano, or nitro;

$R^5$ is hydrogen or $(C_1-C_6)$alkyl;

each $R^6$ is independently selected from halogen, nitro, $(CH_2)_xCN$, $(C_1-C_3)$alkyl, halo$(C_1-C_3)$alkyl, hydroxy$(C_1-C_3)$alkyl, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein when B is heteroaryl, $R^6$ can also be oxo;

each $R^7$ is independently selected from halogen, nitro, cyano, $(C_1-C_3)$alkyl, halo$(C_1-C_3)$alkyl, $(C_1-C_3)$alkoxy, halo$(C_1-C_3)$alkoxy, $N(R^4)_2$, and $CON(R^4)_2$, provided that $R^7$ also includes oxo when $HetAr_1$, $HetCy_1$ and $Cy_1$ are substituted with $R^7$;

x is 0, 1, 2 or 3;

A is a bond or $CH_2$;

m is 0, 1, 2, 3 or 4;

n is 2; and

Q is O or $NR^5$;

or a pharmaceutically acceptable salt thereof.

2. The compound of claim 1, wherein the compound is of Formula (II):

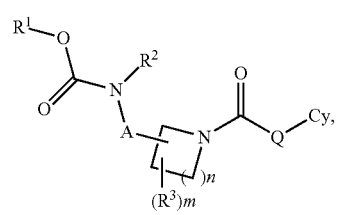

or a pharmaceutically acceptable salt thereof.

3. The compound of claim 2, wherein the compound is of Formula (IV):

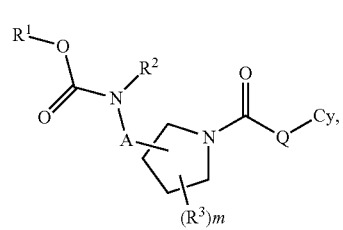

wherein $R^2$ and $R^3$ are independently (a) hydrogen; or (b) $(C_1-C_8)$alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo;

or a pharmaceutically acceptable salt thereof.

4. The compound of claim 3, wherein the compound is of Formula (IVa):

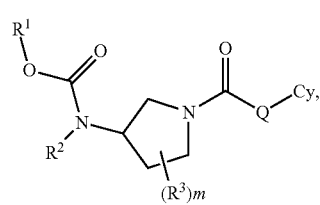

or a pharmaceutically acceptable salt thereof.

5. The compound of claim 3, wherein the compound is of Formula (IVb):

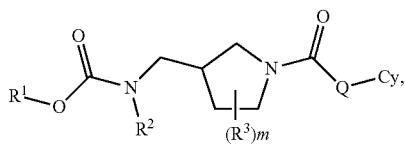
(IVb)

or a pharmaceutically acceptable salt thereof.

6. The compound of claim 3, wherein
Cy is $(C_7-C_{12})$bicycloalkyl or $(C_9-C_{12})$tricycloalkyl which is optionally substituted with 1-3 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$;
$R^1$ is $(C_1-C_8)$alkyl, $(C_3-C_8)$cycloalkyl, $(C_3-C_8)$cycloalkyl$(C_1-C_3)$alkyl, aryl or aryl$(C_1-C_3)$alkyl, each optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$, wherein the $(C_1-C_8)$alkyl, $(C_3-C_8)$cycloalkyl, $(C_3-C_8)$cycloalkyl$(C_1-C_3)$alkyl and the alkyl portion of aryl$(C_1-C_3)$alkyl are further optionally substituted with oxo;
$R^2$ is (a) hydrogen; or (b) $(C_1-C_8)$alkyl, $(C_2-C_8)$alkenyl, aryl, aryl$(C_1-C_3)$alkyl, heteroaryl or heteroaryl$(C_1-C_3)$alkyl, each optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$, wherein the $(C_1-C_8)$alkyl, $(C_2-C_8)$alkenyl, the alkyl portion of aryl$(C_1-C_3)$alkyl, heteroaryl or heteroaryl$(C_1-C_3)$alkyl are further optionally substituted with oxo;
$R^3$ is (a) hydrogen; or (b) $(C_1-C_8)$alkyl, aryl, aryl$(C_1-C_3)$alkyl or $CO_2R^4$, each optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$, wherein the $(C_1-C_8)$alkyl and the alkyl portion of aryl$(C_1-C_3)$alkyl are further optionally substituted with oxo; and
$R^4$ is independently hydrogen or $(C_1-C_3)$alkyl.

7. The compound of claim 3, wherein:
Cy is adamantyl, optionally substituted with 1-3 groups independently selected from halogen, cyano, hydroxy, hydroxy$(C_1-C_3)$alkyl, $N(R^4)_2$, $CO_2R^4$; $CON(R^4)_2$, $CH_2CON(R^4)_2$, $SO_2N(R^4)_2$, $SO_2R^4$, $NR^4COR^4$ and $OC(=O)N(R^4)_2$, wherein each $R^4$ is independently hydrogen or $(C_1-C_3)$alkyl;
$R^1$ is $(C_1-C_8)$alkyl or benzyl, each optionally substituted halogen, nitro, cyano, $(C_1-C_3)$alkyl, halo$(C_1-C_3)$alkyl, $(C_1-C_3)$alkoxy, halo$(C_1-C_3)$alkoxy, $N(R^4)_2$ or $CON(R^4)_2$;
$R^2$ is (a) hydrogen; or (b) benzyl, $(C_1-C_3)$alkyl, allyl or hydroxy$(C_1-C_3)$alkyl, each optionally substituted with halogen, cyano, $(C_1-C_3)$alkyl, halo$(C_1-C_3)$alkyl, $(C_1-C_3)$alkoxy, halo$(C_1-C_3)$alkoxy, $N(R^4)_2$ or $CON(R^4)_2$; and
$R^3$ is (a) hydrogen; or (b) $CO_2R^4$, phenyl, $(C_1-C_3)$alkyl or benzyl, each optionally substituted with halogen, nitro, cyano, $(C_1-C_3)$alkyl, halo$(C_1-C_3)$alkyl, $(C_1-C_3)$alkoxy, halo$(C_1-C_3)$alkoxy, $N(R^4)_2$ or $CON(R^4)_2$.

8. The compound of claim 1, wherein B is heteroaryl, optionally substituted with 1-4 groups represented by $R^6$; wherein each $R^6$ is independently selected from halogen, $(CH_2)_xCN$, $(C_1-C_3)$alkyl, halo$(C_1-C_3)$alkyl, hydroxy$(C_1-C_3)$alkyl, oxo, $(CH_2)_xOR^4$, halo$(C_1-C_3)$alkoxy, $(CH_2)_xN(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xNR^4CON(R^4)_2$ and $(CH_2)_xOC(=O)N(R^4)_2$.

9. The compound of claim 8, wherein the compound is of Formula (VI):

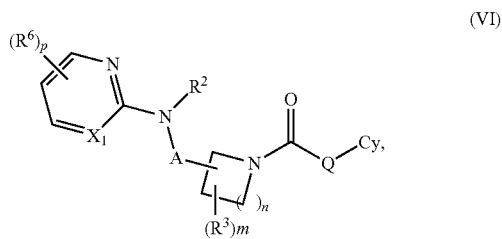
(VI)

wherein
$X_1$ is N or $CR^6$;
each $R^6$ is independently selected from halogen, nitro, $(CH_2)_xCN$, $(C_1-C_3)$alkyl, halo$(C_1-C_3)$alkyl, hydroxy$(C_1-C_3)$alkyl, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$; and
p is 0, 1, 2 or 3;
or a pharmaceutically acceptable salt thereof.

10. The compound of claim 9, wherein the compound is of Formula (VIa):

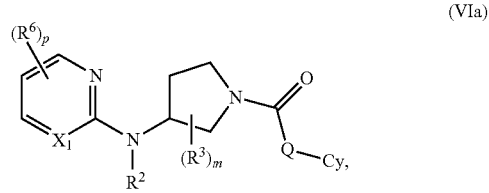
(VIa)

$R^2$ and $R^3$ are independently (a) hydrogen; or (b) $(C_1-C_8)$alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo;

or a pharmaceutically acceptable salt thereof.

11. The compound of claim 8, wherein the compound is of Formula (VIII):

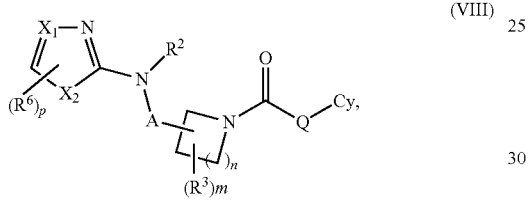

(VIII)

wherein $X_1$ is N or $CR^6$ and $X_2$ is $NR^5$, S or O;

each $R^6$ is independently selected from halogen, nitro, $(CH_2)_xCN$, $(C_1-C_3)$alkyl, halo$(C_1-C_3)$alkyl, hydroxy$(C_1-C_3)$alkyl, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$; and p is 0 or 1;

or a pharmaceutically acceptable salt thereof.

12. The compound of claim 11, wherein the compound is of Formula (VIIIa):

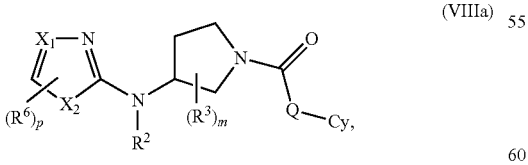

(VIIIa)

$R^2$ and $R^3$ are independently (a) hydrogen; or (b) $(C_1-C_8)$alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl $(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo;

or a pharmaceutically acceptable salt thereof.

13. The compound of claim 8, wherein the compound is of Formula (IX):

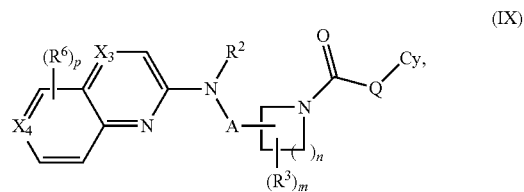

(IX)

wherein $X_3$ is N or $CR^6$;

$X_4$ is N or $CR^6$;

each $R^6$ is independently selected from halogen, nitro, $(CH_2)_xCN$, $(C_1-C_3)$alkyl, halo$(C_1-C_3)$alkyl, hydroxy$(C_1-C_3)$alkyl, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$; and p is 0, 1, 2 or 3;

or a pharmaceutically acceptable salt thereof.

14. The compound of claim 13, wherein the compound is of Formula (IXa):

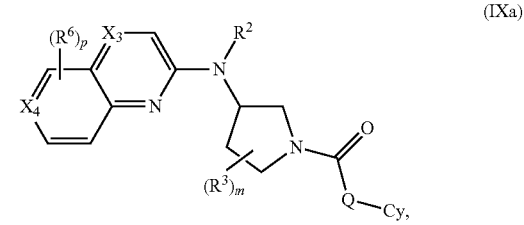

(IXa)

wherein $R^2$ and $R^3$ are independently (a) hydrogen; or (b) $(C_1-C_8)$alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$ alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo;

or a pharmaceutically acceptable salt thereof.

15. The compound of claim 8, wherein the compound is of Formula (X):

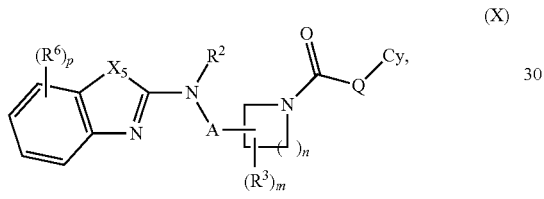

wherein
$X_5$ is S or O;
each $R^6$ is independently selected from halogen, nitro, $(CH_2)_xCN$, $(C_1-C_3)$alkyl, halo$(C_1-C_3)$alkyl, hydroxy$(C_1-C_3)$alkyl, $(CH_2)_xOR^4$, halo$(C_1-C_3)$alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$; and
p is 0, 1, 2 or 3;
or a pharmaceutically acceptable salt thereof.

16. The compound of claim 15, wherein the compound is of Formula (Xa):

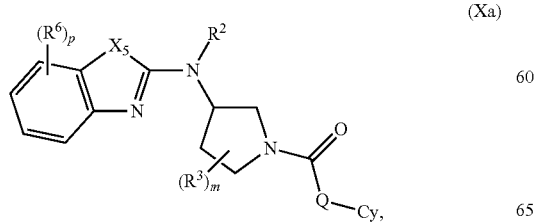

wherein
$R^2$ and $R^3$ are independently (a) hydrogen; or (b) $(C_1-C_8)$alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl$(C_1-C_3)$alkyl, heterocyclyl$(C_1-C_3)$alkyl, aryl$(C_1-C_3)$alkyl, heteroaryl$(C_1-C_3)$alkyl or $(CH_2)_xCO_2R^4$, each optionally substituted by 1-4 groups independently selected from halogen, nitro, $(CH_2)_xCN$, $(C_1-C_3)$alkyl, halo$(C_1-C_3)$alkyl, halo$(C_1-C_3)$alkoxy, hydroxy$(C_1-C_3)$ alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl$(C_1-C_3)$alkyl, heterocyclyl$(C_1-C_3)$alkyl, alkyl portion of aryl$(C_1-C_3)$alkyl and heteroaryl$(C_1-C_3)$alkyl are further optionally substituted with oxo;

or a pharmaceutically acceptable salt thereof.

17. The compound of claim 8, wherein

Cy is $(C_7-C_{12})$bicycloalkyl or $(C_9-C_{12})$tricycloalkyl which is optionally substituted with 1-3 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$;

$R^2$ is (a) hydrogen; or (b) $(C_1-C_8)$alkyl, $(C_2-C_8)$alkenyl, aryl, aryl$(C_1-C_3)$alkyl, heteroaryl or heteroaryl$(C_1-C_3)$alkyl, each optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$, wherein the $(C_1-C_8)$alkyl, $(C_2-C_8)$alkenyl, alkyl portion of aryl$(C_1-C_3)$alkyl, heteroaryl or heteroaryl$(C_1-C_3)$alkyl are further optionally substituted with oxo;

$R^3$ is (a) hydrogen; or (b) $(C_1-C_8)$alkyl, aryl, aryl$(C_1-C_3)$alkyl or $CO_2R^4$, each optionally substituted by 1-4 groups independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$, wherein the $(C_1-C_8)$alkyl and alkyl portion of aryl$(C_1-C_3)$alkyl are further optionally substituted with oxo;

$R^4$ is independently hydrogen, $(C_1-C_3)$alkyl or $(C_3-C_6)$cycloalkyl; and each $R^6$ is independently selected from halogen, cyano, $(C_1-C_3)$alkyl, halo$(C_1-C_3)$alkyl, hydroxy$(C_1-C_3)$alkyl, $OR^4$, $N(R^4)_2$, $CO_2R^4$, $CH_2CO_2R^4$; $CON(R^4)_2$, $CH_2CON(R^4)_2$, $SO_2N(R^4)_2$, $SO_2R^4$, $NR^4COR^4$, $NR^4CO_2R^4$, $NR^4SO_2R^4$, $NR^4CON(R^4)_2$ and $OC(=O)N(R^4)_2$.

18. The compound of claim 17, wherein $R^4$ is independently hydrogen or $(C_1-C_3)$alkyl;

Cy is adamantyl, optionally substituted with 1-3 groups independently selected from halogen, cyano, hydroxy, hydroxy($C_1-C_3$)alkyl, $N(R^4)_2$, $CO_2R^4$; $CON(R^4)_2$, $CH_2CON(R^4)_2$, $SO_2N(R^4)_2$, $SO_2R^4$, $NR^4COR^4$ and $OC(=O)N(R^4)_2$, wherein each $R^4$ is independently hydrogen or $(C_1-C_3)$alkyl;

$R^2$ is (a) hydrogen; or (b) benzyl, $(C_1-C_3)$alkyl, allyl or hydroxy($C_1-C_3$)alkyl, each optionally substituted with halogen, cyano, $(C_1-C_3)$alkyl, halo($C_1-C_3$)alkyl, $(C_1-C_3)$alkoxy, halo($C_1-C_3$)alkoxy, $N(R^4)_2$ or $CON(R^4)_2$.

19. The compound of claim 1, wherein the compound is of Formula (VII):

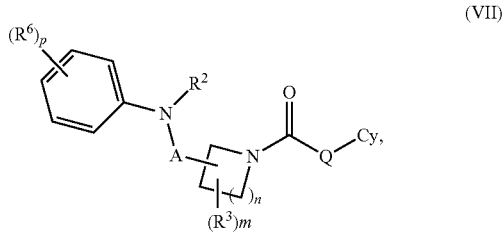

(VII)

wherein
each $R^6$ is independently selected from halogen, nitro, $(CH_2)_xCN$, $(C_1-C_3)$alkyl, halo($C_1-C_3$)alkyl, hydroxy$(C_1-C_3)$alkyl, $(CH_2)_xOR^4$, halo($C_1-C_3$)alkoxy, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$; and
p is 0, 1, 2 or 3;
or a pharmaceutically acceptable salt thereof.

20. The compound of claim 19, wherein the compound is of Formula (VIIa):

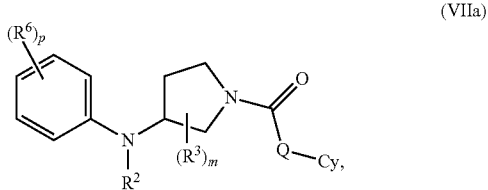

(VIIa)

$R^2$ and $R^3$ are independently (a) hydrogen; or (b) $(C_1-C_8)$alkyl, $(C_2-C_8)$alkenyl, $(C_2-C_8)$alkynyl, $(C_3-C_8)$cycloalkyl, heterocyclyl, aryl, heteroaryl, $(C_3-C_8)$cycloalkyl($C_1-C_3$)alkyl, heterocyclyl($C_1-C_3$)alkyl, aryl($C_1-C_3$)alkyl, heteroaryl($C_1-C_3$)alkyl or $(CH_2)_xCO_2R^4$, each optionally substituted by 1-4 groups independently selected from halogen, nitro, $(CH_2)_xCN$, $(C_1-C_3)$alkyl, halo($C_1-C_3$)alkyl, halo($C_1-C_3$)alkoxy, hydroxy($C_1-C_3$)alkyl, $(CH_2)_xOR^4$, $(CH_2)_xN(R^4)_2$, $(CH_2)_xC(=NOH)NH_2$, $(CH_2)_xNR^4CON(R^4)_2$, $(CH_2)_xCON(R^4)_2$, $(CH_2)_xCO_2R^4$, $(CH_2)_xSO_2N(R^4)_2$, $(CH_2)_xSO_2R^4$, $(CH_2)_xNR^4COR^4$, $(CH_2)_xNR^4CO_2R^4$, $(CH_2)_xNR^4SO_2R^4$, $(CH_2)_xOC(=O)N(R^4)_2$, optionally substituted aryl represented by $Ar_1$, optionally substituted heteroaryl represented by $HetAr_1$, optionally substituted heterocyclyl represented by $HetCy_1$ and optionally substituted cycloalkyl represented by $Cy_1$, wherein $Ar_1$, $HetAr_1$, $HetCy_1$ and $Cy_1$ are optionally substituted with one to three groups represented by $R^7$, wherein the $(C_1-C_8)$alkyl, $(C_2-C_8)$alkenyl, $(C_2-C_8)$alkynyl, $(C_3-C_8)$cycloalkyl, heterocyclyl, heteroaryl, $(C_3-C_8)$cycloalkyl($C_1-C_3$)alkyl, heterocyclyl($C_1-C_3$)alkyl, alkyl portion of aryl($C_1-C_3$)alkyl and heteroaryl($C_1-C_3$)alkyl are further optionally substituted with oxo;
or a pharmaceutically acceptable salt thereof.

21. A pharmaceutical composition comprising: i) a pharmaceutically acceptable carrier or diluent; and ii) the compound in claim 1; or a pharmaceutically acceptable salt thereof.

22. A method of inhibiting 11β-HSD1 activity comprising the step of administering to a mammal in need of such treatment an effective amount of a compound of claim 1.

23. A compound selected from:
(3R)-(2-adamantyl)3-(tert-butoxycarbonylamino)pyrrolidine-1-carboxylate;
(R)-(2-adamantyl)3-(ethoxycarbonylamino)pyrrolidine-1-carboxylate;
(R)-(2-adamantyl)3-(isopropoxycarbonylamino)pyrrolidine-1-carboxylate;
(R)-(2-adamantyl)3-(propoxycarbonylamino)pyrrolidine-1-carboxylate;
(R)-(2-adamantyl)3-(isobutoxycarbonylamino)pyrrolidine-1-carboxylate;
2-adamantyl 3-(tert-butoxycarbonyl(methyl)amino)pyrrolidine-1-carboxylate;
(3R)-(2-adamantyl)3-(benzyloxycarbonylamino)pyrrolidine-1-carboxylate;
(R)-(2-adamantyl)3-(benzyl(tert-butoxycarbonyl)amino)pyrrolidine-1-carboxylate;
(2-adamantyl)3-(tert-butoxycarbonylamino)-3-phenylpyrrolidine-1-carboxylate;
(R)-(1-(methoxycarbonyl)-4-adamantyl)3-(tert-butoxycarbonylamino)pyrrolidine-1-carboxylate;
(3R)-(1-(hydroxymethyl)-4-adamantyl)3-(tert-butoxycarbonylamino)pyrrolidine-1-carboxylate;
(3R)-(1-carbamoyl-4-adamantyl)3-(tert-butoxycarbonylamino)pyrrolidine-1-carboxylate;
(1-carbamoyl-4-adamantyl)(3R-(isobutoxycarbonylamino)pyrrolidine-1-carboxylate);
(R)-(1-cyano-4-adamantyl)3-(tert-butoxycarbonylamino)pyrrolidine-1-carboxylate;
(R)-1-acetamido-4-adamantyl 3-(tert-butoxycarbonylamino)pyrrolidine-1-carboxylate;
(R)-(1-carbamoyl-4-adamantyl)3-(tert-butoxycarbonyl(methyl)amino)pyrrolidine-1-carboxylate;
1-carbamoyl-4-adamantyl 3-(tert-butoxycarbonylamino)-3-methylpyrrolidine-1-carboxylate;
(R)-(1-carbamoyl-4-adamantyl)3-(isopropoxycarbonylamino)pyrrolidine-1-carboxylate;
(R)-(1-carbamoyl-4-adamantyl)3-(benzyloxycarbonylamino)pyrrolidine-1-carboxylate;
(R)-(1-carbamoyl-4-adamantyl)3-(allyl(tert-butoxycarbonyl)amino)pyrrolidine-1-carboxylate;
(R)-(1-(2-hydroxy-2-propyl)-4-adamantyl)3-(tert-butoxycarbonylamino)pyrrolidine-1-carboxylate;
(R)-(1-carbamoyl-4-adamantyl)3-(tert-butoxycarbonyl(2-hydroxyethyl)amino)pyrrolidine-1-carboxylate;

(1-carbamoyl-4-adamantyl)3-benzyl-3-(tert-butoxycarbonylamino)pyrrolidine-1-carboxylate;
(R)-(1-carbamoyl-4-adamantyl)3-(4-(trifluoromethyl)pyrimidin-2-ylamino)pyrrolidine-1-carboxylate;
(R)-(trans-1-carbamoyl-4-adamantyl)3-(5-(trifluoromethyl)pyridin-2-ylamino)pyrrolidine-1-carboxylate;
(R)-(trans-1-carbamoyl-4-adamantyl)3-(2,6-dimethylpyrimidin-4-ylamino)pyrrolidine-1-carboxylate;
(R)-(trans-1-carbamoyl-4-adamantyl)3-(3-cyanopyridin-2-ylamino)pyrrolidine-1-carboxylate;
(R)-(trans-1-carbamoyl-4-adamantyl)3-(5-cyanopyridin-2-ylamino)pyrrolidine-1-carboxylate;
(S)-(trans-1-carbamoyl-4-adamantyl)3-(5-(trifluoromethyl)pyridin-2-ylamino)pyrrolidine-1-carboxylate;
(R)-(trans-1-carbamoyl-4-adamantyl)3-(3-(trifluoromethyl)pyridin-2-ylamino)pyrrolidine-1-carboxylate;
(R)-(trans-1-carbamoyl-4-adamantyl)3-(6-(trifluoromethyl)pyridin-2-ylamino)pyrrolidine-1-carboxylate;
(R)-(trans-1-carbamoyl-4-adamantyl)3-(4-(trifluoromethyl)pyridin-2-ylamino)pyrrolidine-1-carboxylate;
(S)-(trans-1-carbamoyl-4-adamantyl)3-(3-(trifluoromethyl)pyridin-2-ylamino)pyrrolidine-1-carboxylate;
(R)-(trans-1-carbamoyl-4-adamantyl)3-(2-(trifluoromethyl)pyrimidin-4-ylamino)pyrrolidine-1-carboxylate;
(R)-(trans-1-carbamoyl-4-adamantyl)3-(5-(trifluoromethyl)-1,3,4-thiadiazol-2-ylamino)pyrrolidine-1-carboxylate;
(trans-1-carbamoyl-4-adamantyl)3-(methyl(5-(trifluoromethyl)pyridin-2-yl)amino)pyrrolidine-1-carboxylate;
(trans-1-carbamoyl-4-adamantyl)3-(methyl(3-(trifluoromethyl)pyridin-2-yl)amino)pyrrolidine-1-carboxylate;
(trans-1-carbamoyl-4-adamantyl)3-(methyl(6-(trifluoromethyl)pyridin-2-yl)amino)pyrrolidine-1-carboxylate;
(R)-tert-butyl 1-(2-adamantylcarbamoyl)pyrrolidin-3-ylcarbamate;
(S)-tert-butyl 1-(2-adamantylcarbamoyl)pyrrolidin-3-ylcarbamate;
(R)-methyl 1-(2-adamantylcarbamoyl)pyrrolidin-3-ylcarbamate;
(R)-isopropyl 1-((2-adamantyl)carbamoyl)pyrrolidin-3-ylcarbamate;
(R)-isobutyl 1-((2-adamantyl)carbamoyl)pyrrolidin-3-ylcarbamate;
(S)-tert-butyl (1-(2-adamantylcarbamoyl)pyrrolidin-3-yl)methylcarbamate;
tert-butyl 1-(2-adamantylcarbamoyl)pyrrolidin-3-yl(methyl)carbamate;
tert-butyl 1-(2-adamantylcarbamoyl)-3-phenylpyrrolidin-3-ylcarbamate;
(R)-3-(5-cyanopyridin-2-ylamino)-N-(2-adamantyl)pyrrolidine-1-carboxamide;
(R)-(1-carbamoyl-4-adamantyl)3-(pyrimidin-2-ylamino)pyrrolidine-1-carboxylate;
(R)-(trans-1-carbamoyl-4-adamantyl)3-(3-fluoropyridin-2-ylamino)pyrrolidine-1-carboxylate;
(trans-1-carbamoyl-4-adamantyl)3-(tert-butoxycarbonylamino)pyrrolidine-1-carboxylate;
(S)-(trans-1-carbamoyl-4-adamantyl)3-(5-cyanopyridin-2-ylamino)pyrrolidine-1-carboxylate;
(S)-(trans-1-carbamoyl-4-adamantyl)3-(3-cyanopyridin-2-ylamino)pyrrolidine-1-carboxylate;
(trans-1-carbamoyl-4-adamantyl)3-(3-cyanopyridin-2-ylamino)-3-methylpyrrolidine-1-carboxylate;
(trans-1-carbamoyl-4-adamantyl)3-(5-cyanopyridin-2-ylamino)-3-methylpyrrolidine-1-carboxylate;
(R)-(1-(methoxycarbonyl)-4-adamantyl)3-(3-cyanopyridin-2-ylamino)pyrrolidine-1-carboxylate;
(3R)-3-carbamoylbicyclo[3.3.1]nonan-9-yl 3-(5-(trifluoromethyl)pyridin-2-ylamino)pyrrolidine-1-carboxylate;
(3R)(1-carbamoyl-4-adamantyl)3-(5-cyanothiazol-2-ylamino)pyrrolidine-1-carboxylate;
(3R)(trans-1-cyano-4-adamantyl)3-(3-cyanopyridin-2-ylamino)pyrrolidine-1-carboxylate;
(trans-1-carbamoyl-4-adamantyl)3-((5-cyanopyridin-2-yl)(methyl)amino)pyrrolidine-1-carboxylate;
(R)-(1-hydroxy-4-adamantyl)3-(tert-butoxycarbonylamino)pyrrolidine-1-carboxylate;
(R)-(trans-1-hydroxy-4-adamantyl)3-(4-cyanophenylamino)pyrrolidine-1-carboxylate;
(R)-(1-hydroxy-4-adamantyl)3-(5-cyanopyridin-2-ylamino)pyrrolidine-1-carboxylate;
(R)-(trans-1-hydroxy-4-adamantyl)3-(3-cyanopyridin-2-ylamino)pyrrolidine-1-carboxylate;
(R)-(trans-1-hydroxy-4-adamantyl)3-(6-cyanopyrazin-2-ylamino)pyrrolidine-1-carboxylate;
(R)-(trans-1-hydroxy-4-adamantyl)3-(5-cyanothiazol-2-ylamino)pyrrolidine-1-carboxylate;
(R)-(trans-1-hydroxy-4-adamantyl)3-(3-cyano-6-methylpyridin-2-ylamino)pyrrolidine-1-carboxylate;
(R)-(trans-1-hydroxy-4-adamantyl)3-(5-cyano-6-methylpyridin-2-ylamino)pyrrolidine-1-carboxylate;
(R)-(trans-1-hydroxy-4-adamantyl)3-(quinazolin-4-ylamino)pyrrolidine-1-carboxylate;
(R)-(trans-1-hydroxy-4-adamantyl)3-(5-chloro-3-cyanopyridin-2-ylamino)pyrrolidine-1-carboxylate;
(R)-(trans-1-hydroxy-4-adamantyl)3-(3-chloro-5-cyanopyridin-2-ylamino)pyrrolidine-1-carboxylate;
(R)-(trans-1-hydroxy-4-adamantyl)3-(5-methyl-1,6-naphthyridin-2-ylamino)pyrrolidine-1-carboxylate;
(R)-(trans-1-hydroxy-4-adamantyl)3-(3-(dimethylcarbamoyl)pyridin-2-ylamino)pyrrolidine-1-carboxylate;
(R)-(trans-1-hydroxy-4-adamantyl)3-(6-cyanoquinolin-2-ylamino)pyrrolidine-1-carboxylate;
(R)-(trans-1-hydroxy-4-adamantyl)3-(6-cyanoquinoxalin-2-ylamino)pyrrolidine-1-carboxylate;
(R)-(trans-1-hydroxy-4-adamantyl)3-(5-carbamoyl-3-chloropyridin-2-ylamino)pyrrolidine-1-carboxylate;
(R)-(trans-1-hydroxy-4-adamantyl)3-(5-chloro-3-nitropyridin-2-ylamino)pyrrolidine-1-carboxylate;
(R)-(trans-1-hydroxy-4-adamantyl)3-(6-cyanobenzo[d]thiazol-2-ylamino)pyrrolidine-1-carboxylate;
(R)-(trans-1-hydroxy-4-adamantyl)3-(6-chloroquinolin-2-ylamino)pyrrolidine-1-carboxylate;
(R)-(trans-1-hydroxy-4-adamantyl)3-(6-chloroquinoxalin-2-ylamino)pyrrolidine-1-carboxylate;
(R)-(trans-1-hydroxy-4-adamantyl)3-(6-chlorobenzo[d]thiazol-2-ylamino)pyrrolidine-1-carboxylate;
(R)-(trans-1-hydroxy-4-adamantyl)3-(5-chloro-3-(methylcarbamoyl)pyridin-2-ylamino)pyrrolidine-1-carboxylate;
(trans-1-hydroxy-4-adamantyl)3-(5-(tert-butyl(methyl)carbamoyl)pyridin-2-ylamino)pyrrolidine-1-carboxylate;
(trans-1-hydroxy-4-adamantyl)3-(3-(tert-butyl(methyl)carbamoyl)pyridin-2-ylamino)pyrrolidine-1-carboxylate;
(R)-(trans-1-hydroxy-4-adamantyl)3-(5-chloro-3-(cyclopropylcarbamoyl)pyridin-2-ylamino)pyrrolidine-1-carboxylate;

(R)-(trans-1-hydroxy-4-adamantyl)3-(3-(tert-butylcarbamoyl)-5-chloropyridin-2-ylamino)pyrrolidine-1-carboxylate;
(R)-(trans-1-hydroxy-4-adamantyl)3-(6-(cyclopropylcarbamoyl)benzo[d]thiazol-2-ylamino)pyrrolidine-1-carboxylate;
3-((R)-3-(5-cyanopyridin-2-ylamino)pyrrolidine-1-carboxamido)-8-azabicyclo[3.2.1]octane-8-carboxamide;
(3R)-8-carbamoyl-8-azabicyclo[3.2.1]octan-3-yl 3-(5-cyanopyridin-2-ylamino)pyrrolidine-1-carboxylate;
(3R)-3-(5-cyanopyridin-2-ylamino)-N-(8-(methylsulfonyl)-8-azabicyclo[3.2.1]octan-3-yl)pyrrolidine-1-carboxamide;
Methyl 2-((R)-1-((trans-1-hydroxy-4-adamantyloxy)carbonyl)pyrrolidin-3-ylamino)pyrimidine-5-carboxylate;
2-((R)-1-((trans-1-hydroxy-4-adamantyloxy)carbonyl)pyrrolidin-3-ylamino)pyrimidine-5-carboxylic acid;
(R)-(trans-1-hydroxy-4-adamantyl)3-(5-carbamoylpyrimidin-2-ylamino)pyrrolidine-1-carboxylate;
(R)-(trans-1-hydroxy-4-adamantyl)3-(5-(methylcarbamoyl)pyrimidin-2-ylamino)pyrrolidine-1-carboxylate;
(R)-(trans-1-hydroxy-4-adamantyl)3-(5-(dimethylcarbamoyl)pyrimidin-2-ylamino)pyrrolidine-1-carboxylate;
(R)-(trans-1-hydroxy-4-adamantyl)3-(5-(cyclopropylcarbamoyl)pyrimidin-2-ylamino)pyrrolidine-1-carboxylate;
(trans-1-carbamoyl-4-adamantyl)3-(tert-butoxycarbonylamino)-3-(trifluoromethyl)pyrrolidine-1-carboxylate;
(R)-(1-(methylcarbamoyl)-4-adamantyl)3-(5-cyanopyridin-2-ylamino)pyrrolidine-1-carboxylate;
(R)-(1-hydroxy-4-adamantyl)3-(5-fluoropyridin-2-ylamino)pyrrolidine-1-carboxylate;
(R)-(trans-1-carbamoyl-4-adamantyl)3-(6-cyanopyridazin-3-ylamino)pyrrolidine-1-carboxylate;
(R)-(1-(cyclohexylcarbamoyl)-4-adamantyl)3-(5-cyanopyridin-2-ylamino)pyrrolidine-1-carboxylate; and
(R)-(1-(cyclopropylcarbamoyl)-4-adamantyl)3-(5-cyanopyridin-2-ylamino)pyrrolidine-1-carboxylate;
or a pharmaceutically acceptable salt thereof.

24. A compound of claim 23, wherein the compound is (R)-(trans-1-carbamoyl-4-adamantyl)3-(3-cyanopyridin-2-ylamino)pyrrolidine-1-carboxylate, or (R)-(trans-1-carbamoyl-4-adamantyl)3-(5-cyanopyridin-2-ylamino)pyrrolidine-1-carboxylate; or a pharmaceutically acceptable salt thereof.

\* \* \* \* \*